(12) United States Patent
Akiyama et al.

(10) Patent No.: US 11,433,141 B2
(45) Date of Patent: Sep. 6, 2022

(54) ANTI-B7-H4 ANTIBODY

(71) Applicant: SHIZUOKA PREFECTURE, Shizuoka (JP)

(72) Inventors: Yasuto Akiyama, Shizuoka (JP); Akira Iizuka, Shizuoka (JP)

(73) Assignee: SHIZUOKA PREFECTURE, Shizuoka (JP)

( * ) Notice: Subject to any disclaimer, the term of this patent is extended or adjusted under 35 U.S.C. 154(b) by 654 days.

(21) Appl. No.: 16/320,587

(22) PCT Filed: Jul. 25, 2017

(86) PCT No.: PCT/JP2017/026847
§ 371 (c)(1),
(2) Date: Jul. 26, 2019

(87) PCT Pub. No.: WO2018/021301
PCT Pub. Date: Feb. 1, 2018

(65) Prior Publication Data
US 2019/0343964 A1    Nov. 14, 2019

(30) Foreign Application Priority Data
Jul. 26, 2016   (JP) .............................. JP2016-145902

(51) Int. Cl.
| | | |
|---|---|---|
| *A61K 47/69* | (2017.01) | |
| *A61K 47/68* | (2017.01) | |
| *A61P 35/00* | (2006.01) | |
| *A61K 39/395* | (2006.01) | |
| *C07K 16/28* | (2006.01) | |
| *C07K 16/46* | (2006.01) | |
| *A61K 39/00* | (2006.01) | |

(52) U.S. Cl.
CPC ...... *A61K 47/6901* (2017.08); *A61K 39/3955* (2013.01); *A61K 47/6849* (2017.08); *A61P 35/00* (2018.01); *C07K 16/2809* (2013.01); *C07K 16/2827* (2013.01); *C07K 16/468* (2013.01); *A61K 2039/505* (2013.01); *C07K 2317/31* (2013.01); *C07K 2317/55* (2013.01); *C07K 2317/565* (2013.01); *C07K 2317/622* (2013.01); *C07K 2317/732* (2013.01); *C07K 2317/92* (2013.01)

(58) Field of Classification Search
CPC ............ C07K 16/2809; C07K 16/2827; C07K 16/468; C07K 2317/31
USPC ........................................... 424/133.1, 135.1
See application file for complete search history.

(56) References Cited

U.S. PATENT DOCUMENTS

| | | |
|---|---|---|
| 2011/0085970 A1 | 4/2011 | Terrett et al. |
| 2015/0315275 A1 | 11/2015 | Langermann et al. |

FOREIGN PATENT DOCUMENTS

| | | |
|---|---|---|
| JP | 2011-505372 | 2/2011 |
| JP | 2016-509582 | 3/2016 |
| WO | WO 2014/159835 | 10/2014 |

OTHER PUBLICATIONS

Iizaka et al. (Clin Cancer Res 25:2925-2934 (Published OnlineFirst Feb. 8, 2019)).*

(Continued)

*Primary Examiner* — Lynn A Bristol
(74) *Attorney, Agent, or Firm* — Norton Rose Fulbright US LLP

(57) ABSTRACT

An object is to produce a new anti-B7-H4 antibody having high specificity and affinity and provide a composition for treating cancer making use thereof. A monoclonal antibody that specifically binds to an extracellular domain protein of a human B7-H4 protein is newly produced and an "anti-B7-H4 antibody-effector cell complex" in which the monoclonal antibody and an effector cell are bound in order to enhance the antibody-dependent cellular cytotoxicity of the monoclonal antibody or a bispecific antibody comprising an antigen recognition region of the monoclonal antibody and an effector cell antigen recognition region is further produced and used as a composition for treating cancer.

20 Claims, 35 Drawing Sheets

Specification includes a Sequence Listing.

(56) References Cited

OTHER PUBLICATIONS

Anolik et al., "The Relationship of FcγRIIIa Genotype to Degree of B Cell Depletion by Rituximab in the Treatment of Systemic Lupus Erythematosus" *Arthritis & Rheumatism*, 2003, 48(2):455-459.

Cartron et al., "Therapeutic activity of humanized anti-CD20 monoclonal antibody and polymorphism in IgG Fc receptor FcγRIIIa gene" *Blood*, 2002, 99:754-758.

Dall'Ozzo et al., "Rituximab-Dependent Cytotoxicity by Natural Killer Cells: Influence of FCGR3A Polymorphism on the Concentration-Effect Relationship" *Cancer Research*, 2004, 64:4664-4669.

Gennari et al., "Pilot Study of the Mechanism of Action of Preoperative Trastuzumab in Patients with Primary Operable Breast Tumors Overexpressing HER2" *Clinical Cancer Research*, 2004, 10:5650-5655.

Iizuka et al., "Unstable B7-H4 cell surface expression and T-cell redirection as a means of cancer therapy" *Oncology Reports*, 2016, 36:2625-2632.

International Search Report and Written Opinion issued in International Patent Application No. PCT/JP2017/026847, dated Oct. 24, 2017. (English Translation).

Sica et al., "B7-H4, a Molecule of the B7 Family, Negatively Regulates T Cell Immunity" *Immunity*, 2003, 18:849-861.

Smith et al., "B7-H4 as a potential target for immunotherapy for gynecologic cancers: A closer look" *Gynecol Oncol.*, 2014, 134(1):181-189.

Weng & Levy, "Two Immunoglobulin G Fragment C Receptor Polymorphisms Independently Predict Response to Rituximab in Patients With Follicular Lymphoma" *J. Clin. Oncol.*, 2003, 21:3940-3947.

\* cited by examiner

[Figure 1]
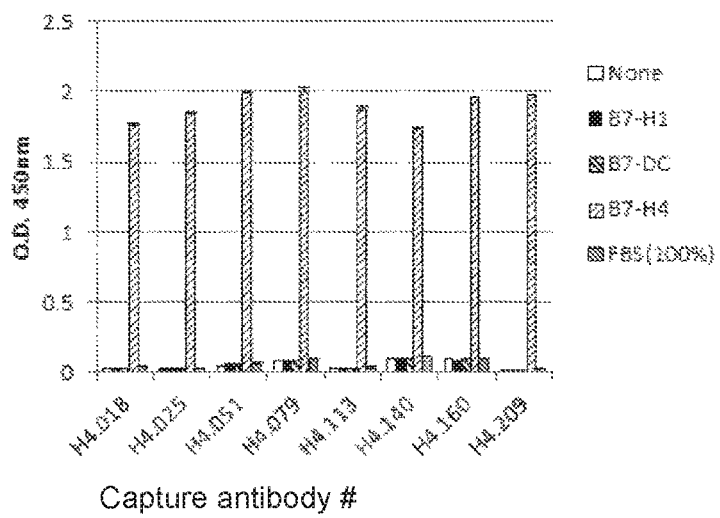
[Figure 2]
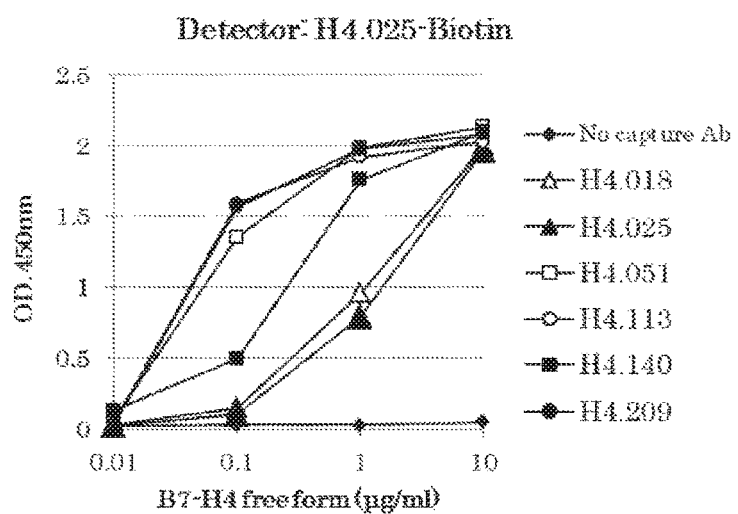

[Figure 3]
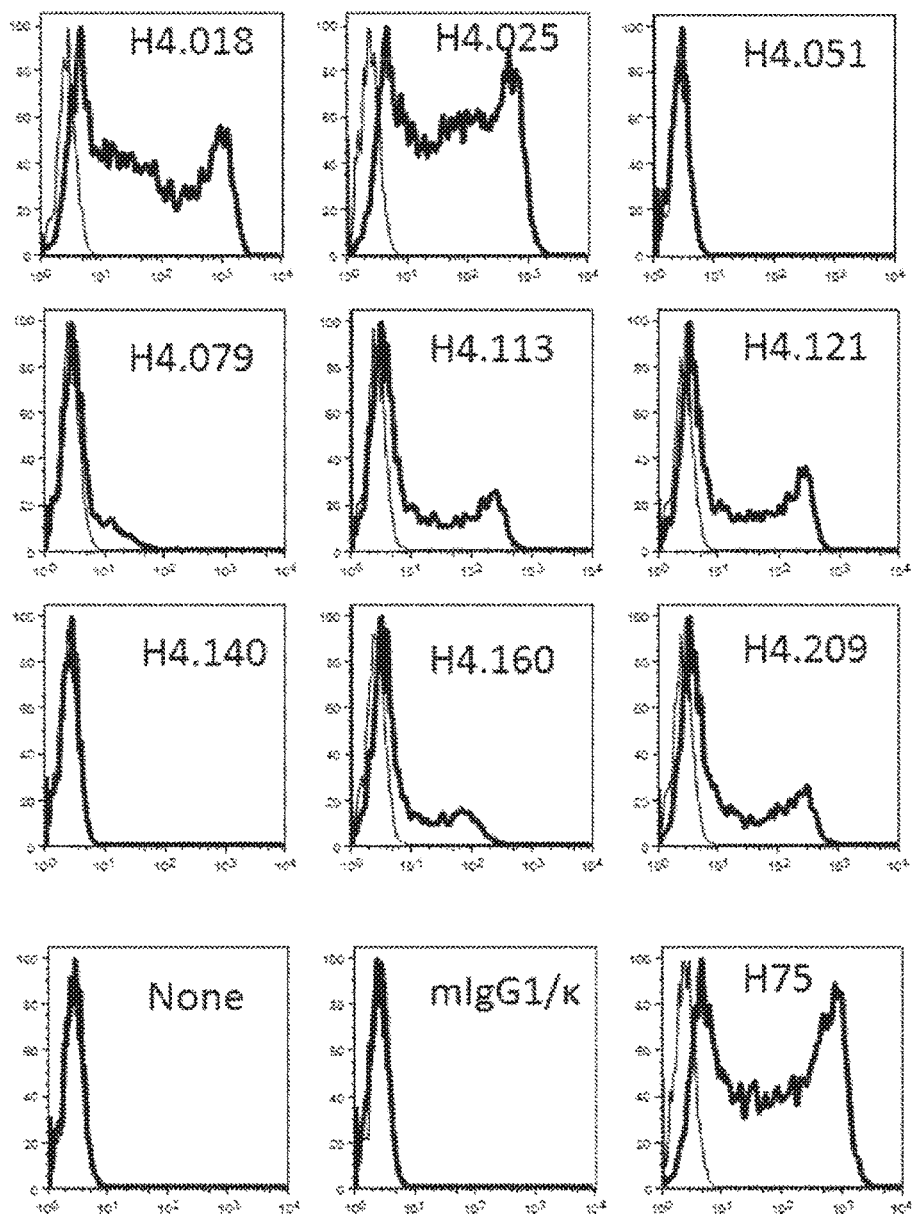

[Figure 4]
Staining of cell surface B7-H4 in carcinoma cell lines
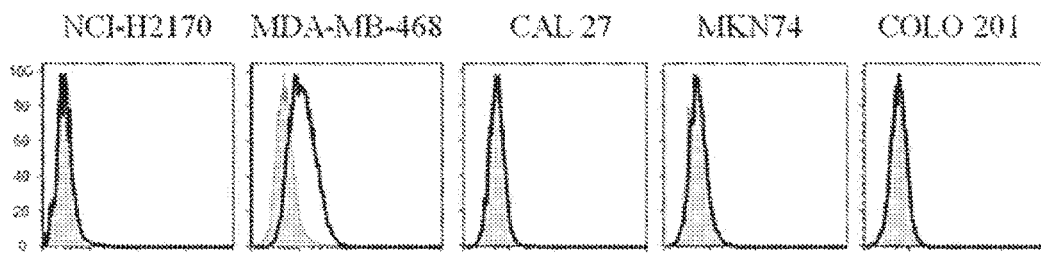
[Figure 5]
(MDA-MB-468, B7-H4 staining)
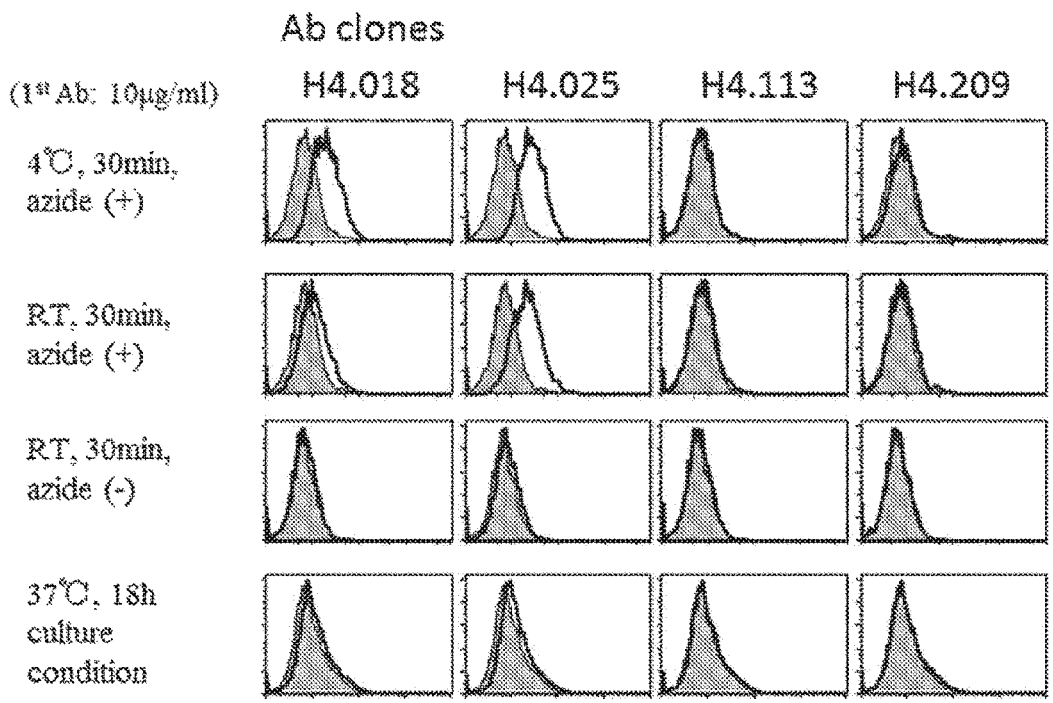

[Figure 6]

Detection of tumor killing activity by indirect ADCC

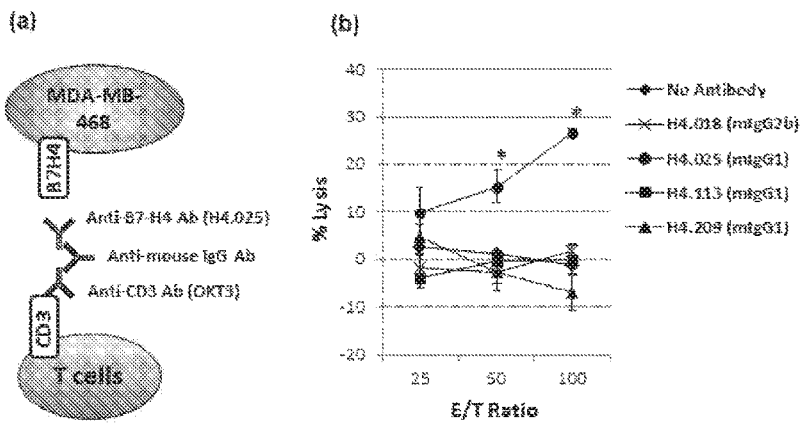

[Figure 7]

```
>H4.018_IGHV
   1   GAA GTG AAG CTG GTG GAG TCT GGG GGA GGC TTA GTG AAG CCT GGA    45
   1   Glu Val Lys Leu Val Glu Ser Gly Gly Gly Leu Val Lys Pro Gly    15

46   GGG TCC CTG AAA CTC TCC TGT GCA GTC TCT GGA TTC ACT TTC AGT    90
  16   Gly Ser Leu Lys Leu Ser Cys Ala Val Ser Gly Phe Thr Phe Ser    30

91   AGC TAT GCC ATG TCT TGG GTT CGC CAG ACT CCG GAG AAG AGG CTG   135
  31   Ser Tyr Ala Met Ser Trp Val Arg Gln Thr Pro Glu Lys Arg Leu    45

136   GAG TGG GTC GCA ACC ATT AGT AGT GGT GGT AAT TAC ACC TAC TAT   180
  46   Glu Trp Val Ala Thr Ile Ser Ser Gly Gly Asn Tyr Thr Tyr Tyr    60

181   CCA GAC AGT GTG AAG GGT CGA TTC ACC ATC TCC AGA GAC AAT GCC   225
  61   Pro Asp Ser Val Lys Gly Arg Phe Thr Ile Ser Arg Asp Asn Ala    75

226   AAG AAC ACC CTG TAC CTG CAA ATG AGC AGT CTG AGG TCT GAG GAC   270
  76   Lys Asn Thr Leu Tyr Leu Gln Met Ser Ser Leu Arg Ser Glu Asp    90

271   ACG GCC ATG TAT TAC TGT GCA AGA CAT CGG TAC GAT AAT AAC TAC   315
  91   Thr Ala Met Tyr Tyr Cys Ala Arg His Arg Tyr Asp Asn Asn Tyr   105

316   GAT TAC TAT GCT ATG GAC TAC TGG GGT   342
 106   Asp Tyr Tyr Ala Met Asp Tyr Trp Gly   114
```

[Figure 8]

>H4.025_IGHV

```
1     GAG TTC CAG CTG CAG CAG TCT GGA CCT GAG CTG GTA AAG CCT GGG      45
1     Glu Phe Gln Leu Gln Gln Ser Gly Pro Glu Leu Val Lys Pro Gly      15

46    GCT TCA GTG AAG ATG TCC TGC AAG GCT TCT GGA TAC ATA TTC ACC      90
16    Ala Ser Val Lys Met Ser Cys Lys Ala Ser Gly Tyr Ile Phe Thr      30

91    AGC TAT GTT GTG CAC TGG GTG AAG CAG AAG CCT GGG CAG GGC CTT      135
31    Ser Tyr Val Val His Trp Val Lys Gln Lys Pro Gly Gln Gly Leu      45

136   GAG TGG ATT GGA TAT ATT AAT CCT TAC AAT GAT GGA ACT AAG TAC      180
46    Glu Trp Ile Gly Tyr Ile Asn Pro Tyr Asn Asp Gly Thr Lys Tyr      60

181   AGT GAA AAG TTC AAA GGC AAG GCC ACA CTG ACC TCA GAC AAA TCC      225
61    Ser Glu Lys Phe Lys Gly Lys Ala Thr Leu Thr Ser Asp Lys Ser      75

226   TCC AGC ACA GCC TAC ATG GAG CTC AGC AGT CTG ACC TCT GAT GAC      270
76    Ser Ser Thr Ala Tyr Met Glu Leu Ser Ser Leu Thr Ser Asp Asp      90

271   TCT GCG GTC TAT TAT TGT GCA AGA GAT GGT GTC TAC GGG TAC CAT      315
91    Ser Ala Val Tyr Tyr Cys Ala Arg Asp Gly Val Tyr Gly Tyr His      105

316   GCT ATG GAC TGC TGG GGT     333
106   Ala Met Asp Cys Trp Gly     111
```

[Figure 9]

>H4.025_IGKV

```
  1    AAC ATT ATG ATG ACA CAG TCG CCA TCA TCT CTG GCT GTG TCT GCA    45
  1    Asn Ile Met Met Thr Gln Ser Pro Ser Ser Leu Ala Val Ser Ala    15

46    GGA GAA AAG GTC ACT ATG AGC TGT AAG TCC AGT CAT GCT GTT TTA    90
 16    Gly Glu Lys Val Thr Met Ser Cys Lys Ser Ser His Ala Val Leu    30

91    TAC AGT TCA AAT CAG AAG AAC TAC TTG GCC TGG TAC CAG CAG AAA    135
 31    Tyr Ser Ser Asn Gln Lys Asn Tyr Leu Ala Trp Tyr Gln Gln Lys    45

136    CCA GGG CAG TCT CCT AAA CTA CTG ATA TAC TGG GCA TCC ACT AGG    180
 46    Pro Gly Gln Ser Pro Lys Leu Leu Ile Tyr Trp Ala Ser Thr Arg    60

181    GAT TCT GGT GTC CCT GAT CGC TTC ACA GGC GGT GGA TCT GGG ACA    225
 61    Asp Ser Gly Val Pro Asp Arg Phe Thr Gly Gly Gly Ser Gly Thr    75

226    GAT TTT ACT CTT ACC ATC ACC AAT ATT CAA CCT GAA GAC CTG GCA    270
 76    Asp Phe Thr Leu Thr Ile Thr Asn Ile Gln Pro Glu Asp Leu Ala    90

271    GTT TAT TAC TGT CAT CAA TAC CTC TCC TCG TGG ACG TTC GGT        312
 91    Val Tyr Tyr Cys His Gln Tyr Leu Ser Ser Trp Thr Phe Gly        104
```

[Figure 10]

>H4.025_IGLV

```
1    CAG GCT GTT GTG ACT CAG GAA TCT GCA CTC ACC ACA TCA CCT GCT    45
1    Gln Ala Val Val Thr Gln Glu Ser Ala Leu Thr Thr Ser Pro Gly    15

46   GAA ACA GTC ACA CTC ACT TGT CGC TCA AGT ACT GGG GCT GTT ACA    90
16   Glu Thr Val Thr Leu Thr Cys Arg Ser Ser Thr Gly Ala Val Thr    30

91   ACT AGT AAC TAT GCC AAC TGG GTC CAA GAG AAA CCA GAT CAT TTA    135
31   Thr Ser Asn Tyr Ala Asn Trp Val Gln Glu Lys Pro Asp His Leu    45

136  TTC ACT GGT CTA ATA GGT GGT ACC AAC GAC CGA GCT CCA GGT GTT    180
46   Phe Thr Gly Leu Ile Gly Gly Thr Asn Asp Arg Ala Pro Gly Val    60

181  CCT GCC AGA TTC TCA GGC TCC CTG ATT GGA GAC AAG GCT GCC CTC    225
61   Pro Ala Arg Phe Ser Gly Ser Leu Ile Gly Asp Lys Ala Ala Leu    75

226  ACC ATC ACA GGG GCA CAG ACT GAG GAT GAG GCA ATA TAT TTC TGT    270
76   Thr Ile Thr Gly Ala Gln Thr Glu Asp Glu Ala Ile Tyr Phe Cys    90

271  GCT CTA TGG TAC AGC AAC CAT TTC CAC AAT GAC ATG TGT AGA TGG    315
91   Ala Leu Trp Tyr Ser Asn His Phe His Asn Asp Met Cys Arg Trp    105

316  GGA    318
106  Gly    106
```

[Figure 11]

```
>H4.051_IGHV

1    GAG GTT CAG CTG CAG CAG TCT GGG GCA GAG CTT GTG AGG TCA GGG    45
  1    Glu Val Gln Leu Gln Gln Ser Gly Ala Glu Leu Val Arg Ser Gly    15

46    GCC TCA GTC AAG TTG TCC TGC ACA GCT TCT GGC TTC AAC ATT AAA    90
 16    Ala Ser Val Lys Leu Ser Cys Thr Ala Ser Gly Phe Asn Ile Lys    30

91    GAC TTC TAT GTA CAC TGG GTG AAG CAG AGG CCT GAA CAG GGC CTG    135
 31    Asp Phe Tyr Val His Trp Val Lys Gln Arg Pro Glu Gln Gly Leu    45

136    GAG TGG ATT GGA TGG ATT GAT CCT GCG CAT GTT GAT ACT GAA TAT    180
 46    Glu Trp Ile Gly Trp Ile Asp Pro Ala His Val Asp Thr Glu Tyr    60

181    GCC CCT AAG TTT CAG GGC AAG ACC ACT ATG ACT GCA GAC ACA TCC    225
 61    Ala Pro Lys Phe Gln Gly Lys Thr Thr Met Thr Ala Asp Thr Ser    75

226    TCC AAC ACA GCC TAC CTG CAG CTC AGC AGC CTG ACA TCT GAA GAC    270
 76    Ser Asn Thr Ala Tyr Leu Gln Leu Ser Ser Leu Thr Ser Glu Asp    90

271    TCT GCC GTC TAT TAC TGT AAT GCC CTC CTA CCA CGG ACT ATG GAC    315
 91    Ser Ala Val Tyr Tyr Cys Asn Ala Leu Leu Pro Arg Thr Met Asp    105

316    TAC TGG GGT    324
106    Tyr Trp Gly    108
```

[Figure 12]

>H4.051_IGKV

| | | | | | | | | | | | | | | | |
|---|---|---|---|---|---|---|---|---|---|---|---|---|---|---|---|
| 1 | GAT | GTT | GTT | CTG | ACC | CAA | ACT | CCA | CTC | TCT | CTG | CCT | GTC | AAT | GTT | 45 |
| 1 | Asp | Val | Val | Leu | Thr | Gln | Thr | Pro | Leu | Ser | Leu | Pro | Val | Asn | Val | 15 |

| 46 | GGA | GAT | CAA | GCC | TCT | ATC | TCC | TGC | AAG | TCT | ACT | AAG | AGT | CTT | CTG | 90 |
| 16 | Gly | Asp | Gln | Ala | Ser | Ile | Ser | Cys | Lys | Ser | Thr | Lys | Ser | Leu | Leu | 30 |

| 91 | AAT | AGT | GAT | GGA | TTC | ACT | TAT | TTG | GAC | TGG | TAT | TTG | CAG | AAG | CCA | 135 |
| 31 | Asn | Ser | Asp | Gly | Phe | Thr | Tyr | Leu | Asp | Trp | Tyr | Leu | Gln | Lys | Pro | 45 |

| 136 | GGC | CAG | TCT | CCA | CAG | CTC | CTA | ATA | TAT | TTG | GTT | TCT | AAT | CGA | TTT | 180 |
| 46 | Gly | Gln | Ser | Pro | Gln | Leu | Leu | Ile | Tyr | Leu | Val | Ser | Asn | Arg | Phe | 60 |

| 181 | TCT | GGA | GTT | CCA | GAC | AGG | TTC | AGT | GGC | AGT | GGG | TCA | GGA | ACA | GAT | 225 |
| 61 | Ser | Gly | Val | Pro | Asp | Arg | Phe | Ser | Gly | Ser | Gly | Ser | Gly | Thr | Asp | 75 |

| 226 | TTC | ACA | CTC | AAG | ATC | AGC | AGA | GTG | GAG | GCT | GAG | GAT | TTG | GGA | GTT | 270 |
| 76 | Phe | Thr | Leu | Lys | Ile | Ser | Arg | Val | Glu | Ala | Glu | Asp | Leu | Gly | Val | 90 |

| 271 | TAT | TAT | TGC | TTC | CAG | AGT | AAC | TAT | CTT | CCG | TAC | ACG | TTC | GGA | | 312 |
| 91 | Tyr | Tyr | Cys | Phe | Gln | Ser | Asn | Tyr | Leu | Pro | Tyr | Thr | Phe | Gly | | 104 |

[Figure 13]

>R4.113_IGHV

```
  1    CAG GTG CAG CTG AAG GAG TCA GGA CCT GGC CTG GTG GCG CCC TCA    45
  1    Gln Val Gln Leu Lys Glu Ser Gly Pro Gly Leu Val Ala Pro Ser    15

46    CAG AGC CTG TCC ATC ACA TGC ACC GTC TCA GGG TTC TCA TTA ACT    90
 16    Gln Ser Leu Ser Ile Thr Cys Thr Val Ser Gly Phe Ser Leu Thr    30

91    AGC TAT GGT GTA CAC TGG GTT CGC CAG CCT CCA GGA AAG GGT CTG    135
 31    Ser Tyr Gly Val His Trp Val Arg Gln Pro Pro Gly Lys Gly Leu    45

136    GAG TGG CTG GTA GTG ATA TGG AGT GAT GGA AGC ACA ACC TAT AAT    180
 46    Glu Trp Leu Val Val Ile Trp Ser Asp Gly Ser Thr Thr Tyr Asn    60

181    TCA GCT CTC AAA TCC AGA CTG AGC ATC AGC AAG GAC AAC TCC AAG    225
 61    Ser Ala Leu Lys Ser Arg Leu Ser Ile Ser Lys Asp Asn Ser Lys    75

226    AGC CAA GTT TTC TTA AAA ATG AAC AGT CTC CAA ACT GAT GAC ACA    270
 76    Ser Gln Val Phe Leu Lys Met Asn Ser Leu Gln Thr Asp Asp Thr    90

271    GCC ATG TAC TAC TGT GCC AGA GAG CCT CCC ACG ACG TAC GTT TGC    315
 91    Ala Met Tyr Tyr Cys Ala Arg Glu Pro Pro Thr Thr Tyr Val Cys    105

316    TTA CTG GGG    324
106    Leu Leu Gly    108
```

[Figure 14]

>H4.113_IGKV

```
  1    GAC ATT GTG ATG TCA CAG TCT CCA TCC TCC CTG GCT GTG TCA GTA    45
  1    Asp Ile Val Met Ser Gln Ser Pro Ser Ser Leu Ala Val Ser Val    15

46    GGA GAG AAG GTC ACC ATG AGC TGC AAA TCC AGT CAG AGT CTG CTC    90
 16    Gly Glu Lys Val Thr Met Ser Cys Lys Ser Ser Gln Ser Leu Leu    30

91    AAC AGT AGA ACC CGA AAG AGC TAT TTG GCT TGG TAC CAG CAG AAA   135
 31    Asn Ser Arg Thr Arg Lys Ser Tyr Leu Ala Trp Tyr Gln Gln Lys    45

136    CCA GGG CAG TCT CCT AAA CTG CTG ATC TAC TGG GCA TCC ACT AGG   180
 46    Pro Gly Gln Ser Pro Lys Leu Leu Ile Tyr Trp Ala Ser Thr Arg    60

181    GAA TCT GGG GTC CCT GAT CGC TTC ACA GGC AGT GGA TCT GGG ACA   225
 61    Glu Ser Gly Val Pro Asp Arg Phe Thr Gly Ser Gly Ser Gly Thr    75

226    GAT TTC ACT CTC ACC ATC AGC AGT GTG CAG GCT GAA GAC CTG GCA   270
 76    Asp Phe Thr Leu Thr Ile Ser Ser Val Gln Ala Glu Asp Leu Ala    90

271    GTT TAT TAC TGC AAG CAA TCT TAT AAT CTG CTC ACG TTC GGT       312
 91    Val Tyr Tyr Cys Lys Gln Ser Tyr Asn Leu Leu Thr Phe Gly      104
```

[Figure 15]

```
>H4.113_IGLV

1       CAG GCT GTT GTG ACT CAG GAA TCT GCA CTC ACC ACA TCA CCT GGT    45
1       Gln Ala Val Val Thr Gln Glu Ser Ala Leu Thr Thr Ser Pro Gly    15

46      GAA ACA GTC ACA CTC ACT TGT CGC TCA ACT ACT GGG GCT GTT ACA    90
16      Glu Thr Val Thr Leu Thr Cys Arg Ser Ser Thr Gly Ala Val Thr    30

91      ACT AGT AAC TAT GCC AAC TGG GTC CAA GAG AAA CCA GAT CAT TTA    135
31      Thr Ser Asn Tyr Ala Asn Trp Val Gln Glu Lys Pro Asp His Leu    45

136     TTC ACT GGT CTA ATA GGT GGT ACC AAC GAC CGA GCT CCA GGT GTT    180
46      Phe Thr Gly Leu Ile Gly Gly Thr Asn Asp Arg Ala Pro Gly Val    60

181     CCT GCC AGA TTC TCA GGC TCC CTG ATT GGA GAC AAG GCT GCC CTC    225
61      Pro Ala Arg Phe Ser Gly Ser Leu Ile Gly Asp Lys Ala Ala Leu    75

226     ACC ATC ACA GGG GCA CAG ACT GAG GAT GAG GCA ATA TAT TTC TGT    270
76      Thr Ile Thr Gly Ala Gln Thr Glu Asp Glu Ala Ile Tyr Phe Cys    90

271     GCT CTA TGG TAC AGC AAC CAT TTC CAC AAT GAC ATG TGT AGA TGG    315
91      Ala Leu Trp Tyr Ser Asn His Phe His Asn Asp Met Cys Arg Trp    105

316     GGA    318
106     Gly    106
```

[Figure 16]

>H4.121_IGHV

```
1    CAG GTT CAG CTG CAG CAG TCT GGA GCT GAA CTG ATG AAA CCT GGG   45
1    Gln Val Gln Leu Gln Gln Ser Gly Ala Glu Leu Met Lys Pro Gly   15

46   GCC TCA GTG AAG ATA TCC TGC AAG GCT ACT GGC TAC ACA TTC AGT   90
16   Ala Ser Val Lys Ile Ser Cys Lys Ala Thr Gly Tyr Thr Phe Ser   30

91   AGC TAC TGG ATA GAG TGG GTA AAG CAG AGG CCT GGA CAT GGC CTT   135
31   Ser Tyr Trp Ile Glu Trp Val Lys Gln Arg Pro Gly His Gly Leu   45

136  GAG TGG ATT GGA GAG ATT TTA CAT GGA AGT GAT AGT ACT AAC TAC   180
46   Glu Trp Ile Gly Glu Ile Leu His Gly Ser Asp Ser Thr Asn Tyr   60

181  AAT GAG AAT TTC AAG GGC AAG GCC ACA TTC ACT GCA GAT ACA TCC   225
61   Asn Glu Asn Phe Lys Gly Lys Ala Thr Phe Thr Ala Asp Thr Ser   75

226  TCC AAC ACA GCC TAC ATG CGA CTC AGC AGC CTG ACA TCT GAG GAC   270
76   Ser Asn Thr Ala Tyr Met Arg Leu Ser Ser Leu Thr Ser Glu Asp   90

271  TCT GCG GTC TAT TAC TGT GCA AGC CAT TAC TAC GGT AGT AGC CCC   315
91   Ser Ala Val Tyr Tyr Cys Ala Ser His Tyr Tyr Gly Ser Ser Pro   105

316  TTT GCT TAC TGG GGC   330
106  Phe Ala Tyr Trp Gly   110
```

[Figure 17]

>H4.121_IGKV

```
1    GAC ATT GTG ATG TCA CAG TCT CCA TCC TCC CTA GCT GTG TCA GTT   45
1    Asp Ile Val Met Ser Gln Ser Pro Ser Ser Leu Ala Val Ser Val   15

46   GGA GAG AAG GTT ACT ATG AGC TGC AAG TCC AGT CAG AGC CTT TTA   90
16   Gly Glu Lys Val Thr Met Ser Cys Lys Ser Ser Gln Ser Leu Leu   30

91   TAT AGT AGT AAT CAA AAG AAT TAC TTG GCC TGG TAC CAG CAG AAA   135
31   Tyr Ser Ser Asn Gln Lys Asn Tyr Leu Ala Trp Tyr Gln Gln Lys   45

136  CCA GGG CAG TCT CCT AAA CTG CTG ATT TAC TGG GCA TCC ACT AGG   180
46   Pro Gly Gln Ser Pro Lys Leu Leu Ile Tyr Trp Ala Ser Thr Arg   60

181  GAA TCT GGG GTC CCT GAT CGC TTC ACA GGC AGT GGA TCT GGG ACA   225
61   Glu Ser Gly Val Pro Asp Arg Phe Thr Gly Ser Gly Ser Gly Thr   75

226  GAT TTC ACT CTC ACC ATC AGC AGT GTG AAG GCT GAA GAC CTG GCA   270
76   Asp Phe Thr Leu Thr Ile Ser Ser Val Lys Ala Glu Asp Leu Ala   90

271  GTT TAT TAC TGT CAG CAA TAT TAT AGC TAT CCG CTC ACG TTC GGT   315
91   Val Tyr Tyr Cys Gln Gln Tyr Tyr Ser Tyr Pro Leu Thr Phe Gly   105
```

[Figure 18]

>H4.140_IGHV

```
1    GAG GTG CAG CTG GTG GAG TCA GGG GGA GAC TTA GTG AAG CCT GGA    45
1    Glu Val Gln Leu Val Glu Ser Gly Gly Asp Leu Val Lys Pro Gly    15

46   GGG TCC CTG AAA CTC TCC TGT GCA GCC TCT GGA TTC ACT TTC AGT    90
16   Gly Ser Leu Lys Leu Ser Cys Ala Ala Ser Gly Phe Thr Phe Ser    30

91   ACC TAT GGC ATG TCT TGG GTT CGC CAG ACT CCA GAC AAG AGG CTG    135
31   Thr Tyr Gly Met Ser Trp Val Arg Gln Thr Pro Asp Lys Arg Leu    45

136  GAG TGG GTC GCA ACC ATT AGT AGT GGT GGT AAT TAC ACC TAC TAT    180
46   Glu Trp Val Ala Thr Ile Ser Ser Gly Gly Asn Tyr Thr Tyr Tyr    60

181  CCA GAC AGT GTG AAG GGG CGA TTC ACC ATC TCC AGA GAC AAT GCC    225
61   Pro Asp Ser Val Lys Gly Arg Phe Thr Ile Ser Arg Asp Asn Ala    75

226  AAG AAC ACC CTG TAC CTG CAA ATG AGC AGT CTG AAG TCT GAG GAC    270
76   Lys Asn Thr Leu Tyr Leu Gln Met Ser Ser Leu Lys Ser Glu Asp    90

271  ACA GCC ATG TAT TAC TGT GCA AGA CCG TAT GGT AAC CAC TTT GAC    315
91   Thr Ala Met Tyr Tyr Cys Ala Arg Pro Tyr Gly Asn His Phe Asp    105

316  TAC TGG GGC    324
106  Tyr Trp Gly    108
```

[Figure 19]

>84.140_IGKV

| | | |
|---|---|---|
| 1 | GAC ATC CAG ATG ACT CAG TCT CCA GCC TCC CTG GCT GCA TCT GTG | 45 |
| 1 | Asp Ile Gln Met Thr Gln Ser Pro Ala Ser Leu Ala Ala Ser Val | 15 |
| 46 | GGA GAA ACT GTC ACC ATC ACA TGT CGA GCA AGT GAG AAC ATT TAC | 90 |
| 16 | Gly Glu Thr Val Thr Ile Thr Cys Arg Ala Ser Glu Asn Ile Tyr | 30 |
| 91 | TAC AGT TTA GCA TGG TAT CAG CAG AAG CAA GGG AAA TCT CCT CAG | 135 |
| 31 | Tyr Ser Leu Ala Trp Tyr Gln Gln Lys Gln Gly Lys Ser Pro Gln | 45 |
| 136 | CTC CTG ATC TAT AAT GCA AAC AGC TTG GAA GAT GGT GTC CCA TCG | 180 |
| 46 | Leu Leu Ile Tyr Asn Ala Asn Ser Leu Glu Asp Gly Val Pro Ser | 60 |
| 181 | AGG TTC AGT GGC AGT GGA TCT GGG ACA CAG TAT TCT ATG AAG ATC | 225 |
| 61 | Arg Phe Ser Gly Ser Gly Ser Gly Thr Gln Tyr Ser Met Lys Ile | 75 |
| 226 | AAC AGC ATG CAG CCT GAA GAT ACC GCA ACT TAT TTC TGT AAA CAG | 270 |
| 76 | Asn Ser Met Gln Pro Glu Asp Thr Ala Thr Tyr Phe Cys Lys Gln | 90 |
| 271 | GCT TAT GAC GTT CCG TAC ACG TTC GGA 297 | |
| 91 | Ala Tyr Asp Val Pro Tyr Thr Phe Gly 99 | |

[Figure 20]

>H4.209_IGHV

```
  1   GAA GTG AAG CTG GTG GAG TCT GGG GGA GGC TTA GTG AAG CCT GGA   45
  1   Glu Val Lys Leu Val Glu Ser Gly Gly Gly Leu Val Lys Pro Gly   15

46   GGG TCC CTG AAA CTC TCC TGT GCA GCC TCT GGA TTC ACT TTC AGT   90
 16   Gly Ser Leu Lys Leu Ser Cys Ala Ala Ser Gly Phe Thr Phe Ser   30

91   AAC TAT GCC TTG TCT TGG GTT CGC CAG ACT CCA GAA AAG AGG CTG   135
 31   Asn Tyr Ala Leu Ser Trp Val Arg Gln Thr Pro Glu Lys Arg Leu   45

136   GAG TGG GTC GCA TCC ATT AGT GGT GGT GGT AGC ACT TAC TAT CCA   180
 46   Glu Trp Val Ala Ser Ile Ser Gly Gly Gly Ser Thr Tyr Tyr Pro   60

181   GAC AGT GTG AAG GGC CGA TTC ATT ATC TCC AGA GAT AAT GCC AGG   225
 61   Asp Ser Val Lys Gly Arg Phe Ile Ile Ser Arg Asp Asn Ala Arg   75

226   AAC ATC CTG TAC CTG CAA ATG AGC AGT CTG AGG TCT GAG GAC ACG   270
 76   Asn Ile Leu Tyr Leu Gln Met Ser Ser Leu Arg Ser Glu Asp Thr   90

271   GCC ATG TAT TAC TGT GCA AGA GGC CCC TCC TAT GAT GAT TAC TAC   315
 91   Ala Met Tyr Tyr Cys Ala Arg Gly Pro Ser Tyr Asp Asp Tyr Tyr   105

316   TTC GAT GTC TGG GGC   330
106   Phe Asp Val Trp Gly   110
```

[Figure 21]

>H4.209_IGKV

```
1    GAT GTT GTG ATG ACC CAG ACT CCA CTC ACT TTG TCG GTT ACC ATT    45
1    Asp Val Val Met Thr Gln Thr Pro Leu Thr Leu Ser Val Thr Ile    15

46   GGA CAA CCA GCC TCC ATC TCT TGC AAG TCA AGT CAG AGC CTC TTA    90
16   Gly Gln Pro Ala Ser Ile Ser Cys Lys Ser Ser Gln Ser Leu Leu    30

91   GAT AGT GCT GGA AAG ACA TAT TTG AAT TGG TTG TTA CAG AGG CCA    135
31   Asp Ser Ala Gly Lys Thr Tyr Leu Asn Trp Leu Leu Gln Arg Pro    45

136  GGC CAG TCT CCA AAG CGC CTA ATT TAC CTG GTG TCT AAA CTG GAC    180
46   Gly Gln Ser Pro Lys Arg Leu Ile Tyr Leu Val Ser Lys Leu Asp    60

181  TCT GGA GTC CCT GAC AGG TTC ACT GGC AGT GGA TCA GGG ACA GAT    225
61   Ser Gly Val Pro Asp Arg Phe Thr Gly Ser Gly Ser Gly Thr Asp    75

226  TTC ACT CTG AAA ATC AGC AGT CTG CAG GCT GAG GAT TTG GGA ATT    270
76   Phe Thr Leu Lys Ile Ser Ser Leu Gln Ala Glu Asp Leu Gly Ile    90

271  TAT TAT TGC TGG CAA GGT ACA CAT TTT CCT CTC ACG TTC GGT        312
91   Tyr Tyr Cys Trp Gln Gly Thr His Phe Pro Leu Thr Phe Gly        104
```

[Figure 22]

Structure of Bispecific antibody

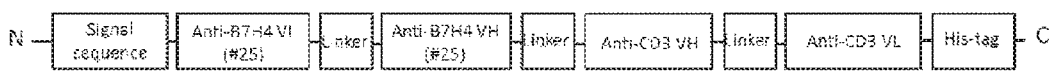

[Figure 23-1]

```
  1    ATG GAA GCC CCA GCT CAG CTT CTC TTC CTC CTG CTA CTC TGG CTC    45
  1    Met Glu Ala Pro Ala Gln Leu Leu Phe Leu Leu Leu Leu Trp Leu    15

46    CCA GAT ACC ACC GGA AAC ATT ATG ATG ACA CAG TCG CCA TCA TCT    90
 16    Pro Asp Thr Thr Gly Asn Ile Met Met Thr Gln Ser Pro Ser Ser    30

91    CTG GCT GTG TCT GCA GGA GAA AAG GTC ACT ATG AGC TGT AAG TCC   135
 31    Leu Ala Val Ser Ala Gly Glu Lys Val Thr Met Ser Cys Lys Ser    45

136    AGT CAT GCT GTT TTA TAC AGT TCA AAT CAG AAG AAC TAC TTG GCC   180
 46    Ser His Ala Val Leu Tyr Ser Ser Asn Gln Lys Asn Tyr Leu Ala    60

181    TGG TAC CAG CAG AAA CCA GGG CAG TCT CCT AAA CTA CTG ATA TAC   225
 61    Trp Tyr Gln Gln Lys Pro Gly Gln Ser Pro Lys Leu Leu Ile Tyr    75

226    TGG GCA TCC ACT AGG GAT TCT GGT GTC CCT GAT CGC TTC ACA GGC   270
 76    Trp Ala Ser Thr Arg Asp Ser Gly Val Pro Asp Arg Phe Thr Gly    90

271    GGT GGA TCT GGG ACA GAT TTT ACT CTT ACC ATC ACC AAT ATT CAA   315
 91    Gly Gly Ser Gly Thr Asp Phe Thr Leu Thr Ile Thr Asn Ile Gln   105

316    CCT GAA GAC CTG GCA GTT TAT TAC TGT CAT CAA TAC CTC TCC TCG   360
106    Pro Glu Asp Leu Ala Val Tyr Tyr Cys His Gln Tyr Leu Ser Ser   120

361    TGG ACG TTC GGA GGC GGT GGG TCA GGC GGT GGA GGG TCT GGT GGA   405
121    Trp Thr Phe Gly Gly Gly Gly Ser Gly Gly Gly Gly Ser Gly Gly   135

406    GGC GGT TCG GAG TTC CAG CTG CAG CAG TCT GGA CCT GAG CTG GTA   450
136    Gly Gly Ser Glu Phe Gln Leu Gln Gln Ser Gly Pro Glu Leu Val   150

451    AAG CCT GGG GCT TCA GTG AAG ATG TCC TGC AAG GCT TCT GGA TAC   495
151    Lys Pro Gly Ala Ser Val Lys Met Ser Cys Lys Ala Ser Gly Tyr   165
```

[Figure 23-2]

```
496  ATA TTC ACC AGC TAT GTT GTG CAC TGG GTG AAG CAG AAG CCT GGG  540
166  Ile Phe Thr Ser Tyr Val Val His Trp Val Lys Gln Lys Pro Gly  180

541  CAG GGC CTT GAG TGG ATT GGA TAT ATT AAT CCT TAC AAT GAT GGA  585
181  Gln Gly Leu Glu Trp Ile Gly Tyr Ile Asn Pro Tyr Asn Asp Gly  195

586  ACT AAG TAC AGT GAA AAG TTC AAA GGC AAG GCC ACA CTG ACC TCA  630
196  Thr Lys Tyr Ser Glu Lys Phe Lys Gly Lys Ala Thr Leu Thr Ser  210

631  GAC AAA TCC TCC AGC ACA GCC TAC ATG GAG CTC AGC AGT CTG ACC  675
211  Asp Lys Ser Ser Ser Thr Ala Tyr Met Glu Leu Ser Ser Leu Thr  225

676  TCT GAT GAC TCT GCG GTC TAT TAT TGT GCA AGA GAT GGT GTC TAC  720
226  Ser Asp Asp Ser Ala Val Tyr Tyr Cys Ala Arg Asp Gly Val Tyr  240

721  GGG TAC CAT GCT ATG GAC TGC TGG GGT CAA GGA GAG CCC AAA TCT  765
241  Gly Tyr His Ala Met Asp Cys Trp Gly Gln Gly Glu Pro Lys Ser  255

766  TCA GAC AAA ACT CAC ACA TCA CCA CCG TCA CCA GCT CAG GTC CAG  810
256  Ser Asp Lys Thr His Thr Ser Pro Pro Ser Pro Ala Gln Val Gln  270

811  CTG CAG CAG TCT GGG GCT GAA CTG GCA AGA CCT GGG GCC TCA GTG  855
271  Leu Gln Gln Ser Gly Ala Glu Leu Ala Arg Pro Gly Ala Ser Val  285

856  AAG ATG TCC TGC AAG GCT TCT GGC TAC ACC TTT ACT AGG TAC ACG  900
286  Lys Met Ser Cys Lys Ala Ser Gly Tyr Thr Phe Thr Arg Tyr Thr  300

901  ATG CAC TGG GTA AAA CAG AGG CCT GGA CAG GGT CTG GAA TGG ATT  945
301  Met His Trp Val Lys Gln Arg Pro Gly Gln Gly Leu Glu Trp Ile  315

946  GGA TAC ATT AAT CCT AGC CGT GGT TAT ACT AAT TAC AAT CAG AAG  990
316  Gly Tyr Ile Asn Pro Ser Arg Gly Tyr Thr Asn Tyr Asn Gln Lys  330

991  TTC AAG GAC AAG GCC ACA TTG ACT ACA GAC AAA TCC TCC AGC ACA  1035
331  Phe Lys Asp Lys Ala Thr Leu Thr Thr Asp Lys Ser Ser Ser Thr  345
```

[Figure 23-3]

```
1036  GCC TAC ATG CAA CTG AGC AGC CTG ACA TCT GAG GAC TCT GCA GTC  1080
346   Ala Tyr Met Gln Leu Ser Ser Leu Thr Ser Glu Asp Ser Ala Val  360

1081  TAT TAC TGT GCA AGA TAT TAT GAT GAT CAT TAC TGC CTT GAC TAC  1125
361   Tyr Tyr Cys Ala Arg Tyr Tyr Asp Asp His Tyr Cys Leu Asp Tyr  375

1126  TGG GGT GGC GGA GGT TCA GGA GGT GGC GGA TCT GGT GGC GGA GGC  1170
376   Trp Gly Gly Gly Gly Ser Gly Gly Gly Gly Ser Gly Gly Gly Gly  390

1171  TCG CAA ATT GTT CTC ACC CAG TCT CCA GCA ATC ATG TCT GCA TCT  1215
391   Ser Gln Ile Val Leu Thr Gln Ser Pro Ala Ile Met Ser Ala Ser  405

1216  CCA GGG GAG AAG GTC ACC ATG ACC TGC AGT GCC AGC TCA AGT GTA  1260
406   Pro Gly Glu Lys Val Thr Met Thr Cys Ser Ala Ser Ser Ser Val  420

1261  AGT TAC ATG AAC TGG TAC CAG CAG AAG TCA GGC ACC TCC CCC AAA  1305
421   Ser Tyr Met Asn Trp Tyr Gln Gln Lys Ser Gly Thr Ser Pro Lys  435

1306  AGA TGG ATT TAT GAC ACA TCC AAA CTG GCT TCT GGA GTC CCT GCT  1350
436   Arg Trp Ile Tyr Asp Thr Ser Lys Leu Ala Ser Gly Val Pro Ala  450

1351  CAC TTC AGG GGC AGT GGG TCT GGG ACC TCT TAC TCT CTC ACA ATC  1395
451   His Phe Arg Gly Ser Gly Ser Gly Thr Ser Tyr Ser Leu Thr Ile  465

1396  AGC GGC ATG GAG GCT GAA GAT GCT GCC ACT TAT TAC TGC CAG CAG  1440
466   Ser Gly Met Glu Ala Glu Asp Ala Ala Thr Tyr Tyr Cys Gln Gln  480

1441  TGG AGT AGT AAC CCA TTC ACG TTC GGC TCG GGA GGC GGT CAC CAC  1485
481   Trp Ser Ser Asn Pro Phe Thr Phe Gly Ser Gly Gly Gly His His  495

1486  CAC CAC CAC CAC TGA  1500
496   His His His His End  500
```

[Figure 24]
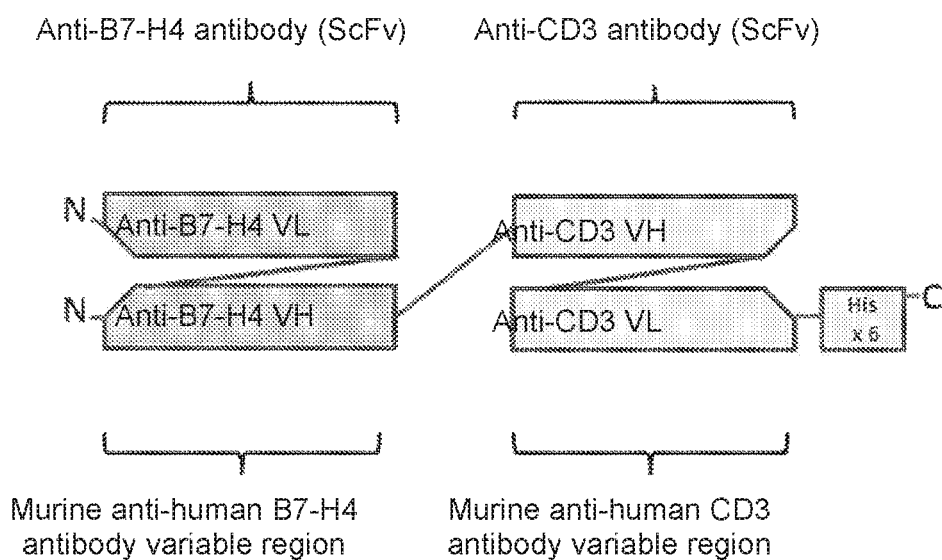

[Figure 25-1]

```
  1   ATG GAC ATG AGG GTC CCC GCT CAG CTC CTG GGG CTC CTT CTG CTT   45
  1   Met Asp Met Arg Val Pro Ala Gln Leu Leu Gly Leu Leu Leu Leu   15

46   TGG TTC CCA GGC GCC AGA TGT AAT ATT CAG ATG ACC CAG TCA CCG   90
 16   Trp Phe Pro Gly Ala Arg Cys Asn Ile Gln Met Thr Gln Ser Pro   30

91   AGC TCA CTG GCA GTT AGT GCC GGC GAA AAA GTT ACC ATG AGC TGT   135
 31   Ser Ser Leu Ala Val Ser Ala Gly Glu Lys Val Thr Met Ser Cys   45

136   AAA AGC AGC CAT GCA GTT CTG TAT AGC AGC AAC CAG AAA AAC TAT   180
 46   Lys Ser Ser His Ala Val Leu Tyr Ser Ser Asn Gln Lys Asn Tyr   60

181   CTG GCA TGG TAC CAG CAG AAG CCG GGT CAG AGC CCG AAA CTG CTG   225
 61   Leu Ala Trp Tyr Gln Gln Lys Pro Gly Gln Ser Pro Lys Leu Leu   75

226   ATT TAT TGG GCC AGC ACC CGC GAT AGC GGT GTT CCG GAT CGC TTT   270
 76   Ile Tyr Trp Ala Ser Thr Arg Asp Ser Gly Val Pro Asp Arg Phe   90

271   ACC GGT GGT GGT AGC GGC ACC GAT TTT ACC CTG ACC ATT ACC AAT   315
 91   Thr Gly Gly Gly Ser Gly Thr Asp Phe Thr Leu Thr Ile Thr Asn   105

316   ATT CAG CCG GAA GAT CTG GCA GTG TAT TAT TGT CAT CAG TAT TTA   360
106   Ile Gln Pro Glu Asp Leu Ala Val Tyr Tyr Cys His Gln Tyr Leu   120

361   AGC AGC TGG ACC TTT GGT GGT GGC ACC AAA GTT GAA ATC AAG GCA   405
121   Ser Ser Trp Thr Phe Gly Gly Gly Thr Lys Val Glu Ile Lys Gly   135

406   GGC TCA GGA GGC GGT GGG TCT GGT GGG GGC GGA TCG GGC GGA GAA   450
136   Gly Ser Gly Gly Gly Gly Ser Gly Gly Gly Gly Ser Gly Gly Glu   150

451   TTT CAG CTG CAA CAG AGC GGT CCG GAG CTG GTT AAA CCG GGC GCA   495
151   Phe Gln Leu Gln Gln Ser Gly Pro Glu Leu Val Lys Pro Gly Ala   165

496   AGC GTT AAA ATG AGC TGC AAA GCA AGC GGT TAT ATC TTT ACC AGC   540
166   Ser Val Lys Met Ser Cys Lys Ala Ser Gly Tyr Ile Phe Thr Ser   180
```

[Figure 25-2]

```
541  TAT GTT GTT CAT TGG GTG AAA CAG AAA CCT GGC CAA GGT CTG GAG  585
181  Tyr Val Val His Trp Val Lys Gln Lys Pro Gly Gln Gly Leu Glu  195

586  TGG ATT GGT TAT ATC AAT CCG TAT AAT GAC GGC ACC AAA TAC AGC  630
196  Trp Ile Gly Tyr Ile Asn Pro Tyr Asn Asp Gly Thr Lys Tyr Ser  210

631  GAA AAA TTC AAA GGT AAA GCA ACC CTG ACC TCC GAT AAA AGC AGT  675
211  Glu Lys Phe Lys Gly Lys Ala Thr Leu Thr Ser Asp Lys Ser Ser  225

676  AGC ACC GCA TAT ATG GAA CTG AGC AGT CTG ACC AGT GAT GAT AGC  720
226  Ser Thr Ala Tyr Met Glu Leu Ser Ser Leu Thr Ser Asp Asp Ser  240

721  GCA GTT TAT TAC TGT GCA CGC GAT GGT GTT TAT GGT TAT CAT GCA  765
241  Ala Val Tyr Tyr Cys Ala Arg Asp Gly Val Tyr Gly Tyr His Ala  255

766  ATG GAT TGC TGG GGT CAG GGC ACC AGC GTT ACC GTT AGC AGT GGA  810
256  Met Asp Cys Trp Gly Gln Gly Thr Ser Val Thr Val Ser Ser Gly  270

811  GGT TCT GGA GGT GGC GGG TCC GGC GGG GGT GGA TCA GGT GGA CAG  855
271  Gly Ser Gly Gly Gly Gly Ser Gly Gly Gly Gly Ser Gly Gly Gln  285

856  GTG CAA CTG CAA CAG TCA GGT GCC GAA CTG GCA CGC CCG GGT GCC  900
286  Val Gln Leu Gln Gln Ser Gly Ala Glu Leu Ala Arg Pro Gly Ala  300

901  TCA GTT AAA ATG TCA TGT AAA GCA AGT GGC TAT ACC TTC ACA CGC  945
301  Ser Val Lys Met Ser Cys Lys Ala Ser Gly Tyr Thr Phe Thr Arg  315

946  TAT ACC ATG CAC TGG GTT AAA CAG CGC CCA GGT CAG GGC TTA GAA  990
316  Tyr Thr Met His Trp Val Lys Gln Arg Pro Gly Gln Gly Leu Glu  330

991  TGG ATC GGC TAT ATT AAC CCG AGC CGC GGT TAT ACC AAT TAC AAC  1035
331  Trp Ile Gly Tyr Ile Asn Pro Ser Arg Gly Tyr Thr Asn Tyr Asn  345

1036 CAG AAG TTT AAA GAC AAA GCC ACA CTG ACC ACA GAT AAA TCA AGC  1080
346  Gln Lys Phe Lys Asp Lys Ala Thr Leu Thr Thr Asp Lys Ser Ser  360
```

[Figure 25-3]

```
1081  TCA ACC GCC TAT ATG CAG CTG TCA AGC CTT ACC AGC GAA GAT TCT  1125
 361  Ser Thr Ala Tyr Met Gln Leu Ser Ser Leu Thr Ser Glu Asp Ser   375

1126  GCA GTA TAC TAT TGT GCC CGC TAT TAT GAT GAT CAC TAT TGC CTG  1170
 376  Ala Val Tyr Tyr Cys Ala Arg Tyr Tyr Asp Asp His Tyr Cys Leu   390

1171  GAT TAT TGG GGA CAA GGT ACG ACC CTG ACC GTT TCA AGT GGA GGG  1215
 391  Asp Tyr Trp Gly Gln Gly Thr Thr Leu Thr Val Ser Ser Gly Gly   405

1216  TCG GGA GGG GGT GGC TCA GGT GGC GGA GGA TCC GGA GGG CAG ATT  1260
 406  Ser Gly Gly Gly Gly Ser Gly Gly Gly Gly Ser Gly Gly Gln Ile   420

1261  GTT CTG ACC CAG AGT CCG GCA ATT ATG AGC GCA AGT CCG GGT GAG  1305
 421  Val Leu Thr Gln Ser Pro Ala Ile Met Ser Ala Ser Pro Gly Glu   435

1306  AAA GTG ACA ATG ACC TGT AGC GCA AGC AGC GTT AGC TAT ATG      1350
 436  Lys Val Thr Met Thr Cys Ser Ala Ser Ser Val Ser Tyr Met       450

1351  AAT TGG TAC CAA CAA AAA AGC GGC ACC AGT CCG AAA CGC TGG ATT  1395
 451  Asn Trp Tyr Gln Gln Lys Ser Gly Thr Ser Pro Lys Arg Trp Ile   465

1396  TAT GAT ACC AGC AAA CTG GCA AGT GGC GTT CCG GCA CAT TTT CGC  1440
 466  Tyr Asp Thr Ser Lys Leu Ala Ser Gly Val Pro Ala His Phe Arg   480

1441  GGT TCA GGC AGC GGT ACA AGC TAT AGC CTG ACA ATT AGC GGT ATG  1485
 481  Gly Ser Gly Ser Gly Thr Ser Tyr Ser Leu Thr Ile Ser Gly Met   495

1486  GAA GCA GAA GAT GCA GCA ACC TAT TAC TGC CAG CAG TGG TCA AGC  1530
 496  Glu Ala Glu Asp Ala Ala Thr Tyr Tyr Cys Gln Gln Trp Ser Ser   510

1531  AAT CCG TTT ACA TTT GGT TCA GGC ACG AAA CTG GAA ATT AAA GGT  1575
 511  Asn Pro Phe Thr Phe Gly Ser Gly Thr Lys Leu Glu Ile Lys Gly   525

1576  GGT GGT CAT CAT CAC CAC CAT CAC TAA  1602
 526  Gly Gly His His His His His His End  534
```

[Figure 26]
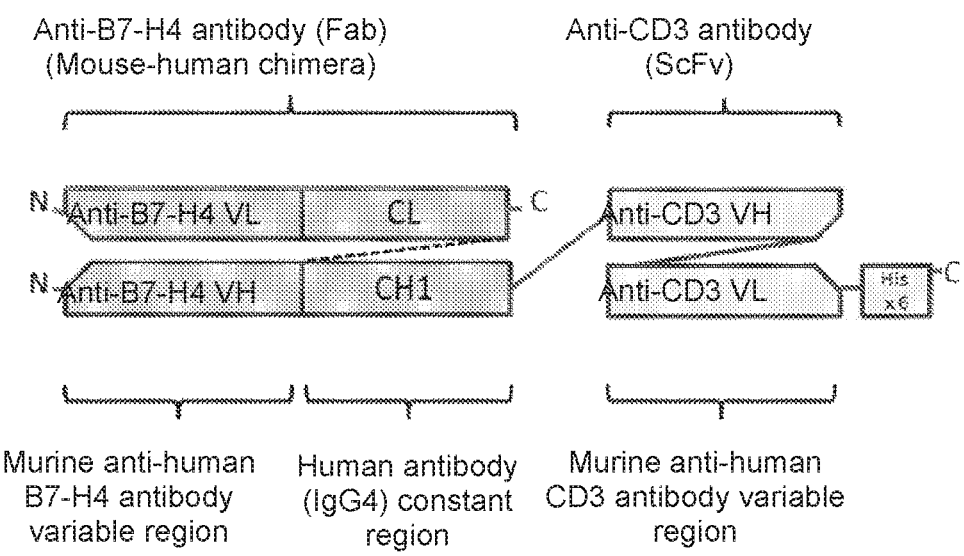

[Figure 27-1]

```
1    ATG GAG TTG GGG CTG TGC TGG GTT TTC CTT GTT GCT ATT TTA AAA    45
1    Met Glu Leu Gly Leu Cys Trp Val Phe Leu Val Ala Ile Leu Lys    15

46   GGT GTC CAG TGT GAA GTG CAG CTG CAA CAG AGC GGT CCG GAG CTG    90
16   Gly Val Gln Cys Glu Val Gln Leu Gln Gln Ser Gly Pro Glu Leu    30

91   GTT AAA CCG GGC GCA AGC GTT AAA ATG AGC TGC AAA GCA AGC GGT    135
31   Val Lys Pro Gly Ala Ser Val Lys Met Ser Cys Lys Ala Ser Gly    45

136  TAT ATC TTT ACC AGC TAT GTT GTT CAT TGG GTG AAA CAG AAA CCT    180
46   Tyr Ile Phe Thr Ser Tyr Val Val His Trp Val Lys Gln Lys Pro    60

181  GGC CAA GGT CTG GAG TGG ATT GGT TAT ATC AAT CCG TAT AAT GAC    225
61   Gly Gln Gly Leu Glu Trp Ile Gly Tyr Ile Asn Pro Tyr Asn Asp    75

226  GGC ACC AAA TAC AGC GAA AAA TTC AAA GGT AAA GCA ACC CTG ACC    270
76   Gly Thr Lys Tyr Ser Glu Lys Phe Lys Gly Lys Ala Thr Leu Thr    90

271  TCC GAT AAA AGC AGT AGC ACC GCA TAT ATG GAA CTG AGC AGT CTG    315
91   Ser Asp Lys Ser Ser Ser Thr Ala Tyr Met Glu Leu Ser Ser Leu    105

316  ACC AGT GAT GAT AGC GCA GTT TAT TAC TGT GCA CGC GAT GGT GTT    360
106  Thr Ser Asp Asp Ser Ala Val Tyr Tyr Cys Ala Arg Asp Gly Val    120

361  TAT GGT TAT CAT GCA ATG GAT TGC TGG GGT CAG GGC ACC AGC GTT    405
121  Tyr Gly Tyr His Ala Met Asp Cys Trp Gly Gln Gly Thr Ser Val    135

406  ACC GTT AGC AGT GCA TCC ACC AAG GGC CCA TCG GTC TTC CCC CTG    450
136  Thr Val Ser Ser Ala Ser Thr Lys Gly Pro Ser Val Phe Pro Leu    150

451  GCA CCC TGC TCC AGG AGC ACC TCC GAG AGC ACA GCC GCC CTG GGC    495
151  Ala Pro Cys Ser Arg Ser Thr Ser Glu Ser Thr Ala Ala Leu Gly    165

496  TGC CTG GTC AAG GAC TAC TTC CCC GAA CCG GTG ACG GTG TCG TGG    540
166  Cys Leu Val Lys Asp Tyr Phe Pro Glu Pro Val Thr Val Ser Trp    180
```

[Figure 27-2]

```
541  AAC TCA GGC GCC CTG ACC AGC GGC GTG CAC ACC TTC CCG GCT GTC  585
181  Asn Ser Gly Ala Leu Thr Ser Gly Val His Thr Phe Pro Ala Val  195

586  CTA CAG TCC TCA GGA CTC TAT TCC CTC AGC AGC GTG GTG ACC GTG  630
196  Leu Gln Ser Ser Gly Leu Tyr Ser Leu Ser Ser Val Val Thr Val  210

631  CCC TCC AGC AGC TTG GGC ACG AAG ACC TAC ACC TGC AAC GTA GAT  675
211  Pro Ser Ser Ser Leu Gly Thr Lys Thr Tyr Thr Cys Asn Val Asp  225

676  CAC AAG CCC AGC AAC ACC AAG GTG GAC AAG AGA GTT Cag tcc aaa  720
226  His Lys Pro Ser Asn Thr Lys Val Asp Lys Arg Val Glu Ser Lys  240

721  tat ggt gga ggt TCT ggg ggt ggc ggg TCC ggc ggg ggt gga TCA  765
241  Tyr Gly Gly Gly Ser Gly Gly Gly Gly Ser Gly Gly Gly Gly Ser  255

766  ggt gga CAG GTG CAA CTG CAA CAG TCA GGT GCC GAA CTG GCA CGC  810
256  Gly Gly Gln Val Gln Leu Gln Gln Ser Gly Ala Glu Leu Ala Arg  270

811  CCG GGT GCC TCA GTT AAA ATG TCA TGT AAA GCA AGT GGC TAT ACC  855
271  Pro Gly Ala Ser Val Lys Met Ser Cys Lys Ala Ser Gly Tyr Thr  285

856  TTC ACA CGC TAT ACC ATG CAC TGG GTT AAA CAG CGC CCA GGT CAG  900
286  Phe Thr Arg Tyr Thr Met His Trp Val Lys Gln Arg Pro Gly Gln  300

901  GGC TTA GAA TGG ATC GGC TAT ATT AAC CCG AGC CGC GGT TAT ACC  945
301  Gly Leu Glu Trp Ile Gly Tyr Ile Asn Pro Ser Arg Gly Tyr Thr  315

946  AAT TAC AAC CAG AAG TTT AAA GAC AAA GCC ACA CTG ACC ACA GAT  990
316  Asn Tyr Asn Gln Lys Phe Lys Asp Lys Ala Thr Leu Thr Thr Asp  330

991  AAA TCA AGC TCA ACC GCC TAT ATG CAG CTG TCA AGC CTT ACC AGC  1035
331  Lys Ser Ser Ser Thr Ala Tyr Met Gln Leu Ser Ser Leu Thr Ser  345

1036 GAA GAT TCT GCA GTA TAC TAT TGT GCC CGC TAT TAT GAT GAT CAC  1080
346  Glu Asp Ser Ala Val Tyr Tyr Cys Ala Arg Tyr Tyr Asp Asp His  360
```

[Figure 27-3]

```
1081  TAT TGC CTG GAT TAT TGG GGA CAA GGT ACG ACC CTG ACC GTT TCA  1125
 361  Tyr Cys Leu Asp Tyr Trp Gly Gln Gly Thr Thr Leu Thr Val Ser   375

1126  AGT gga ggg TCG gga ggg ggt ggc TCA ggt ggc gga gga TCC gga   1170
 376  Ser Gly Gly Ser Gly Gly Gly Gly Ser Gly Gly Gly Gly Ser Gly   390

1171  ggg CAG ATT GTT CTG ACC CAG AGT CCG GCA ATT ATG AGC GCA AGT   1215
 391  Gly Gln Ile Val Leu Thr Gln Ser Pro Ala Ile Met Ser Ala Ser   405

1216  CCG GGT GAG AAA GTG ACA ATG ACC TGT AGC GCA AGC AGC AGC GTT   1260
 406  Pro Gly Glu Lys Val Thr Met Thr Cys Ser Ala Ser Ser Ser Val   420

1261  AGC TAT ATG AAT TGG TAC CAA CAA AAA AGC GGC ACC AGT CCG AAA   1305
 421  Ser Tyr Met Asn Trp Tyr Gln Gln Lys Ser Gly Thr Ser Pro Lys   435

1306  CGC TGG ATT TAT GAT ACC AGC AAA CTG GCA AGT GGC GTT CCG GCA   1350
 436  Arg Trp Ile Tyr Asp Thr Ser Lys Leu Ala Ser Gly Val Pro Ala   450

1351  CAT TTT CGC GGT TCA GGC AGC GGT ACA AGC TAT AGC CTG ACA ATT   1395
 451  His Phe Arg Gly Ser Gly Ser Gly Thr Ser Tyr Ser Leu Thr Ile   465

1396  AGC GGT ATG GAA GCA GAA GAT GCA GCA ACC TAT TAC TGC CAG CAG   1440
 466  Ser Gly Met Glu Ala Glu Asp Ala Ala Thr Tyr Tyr Cys Gln Gln   480

1441  TGG TCA AGC AAT CCG TTT ACA TTT GGT TCA GGC ACC AAA CTG GAA   1485
 481  Trp Ser Ser Asn Pro Phe Thr Phe Gly Ser Gly Thr Lys Leu Glu   495

1486  ATT AAA GGT GGT GGT CAT CAT CAC CAC CAT CAC TAA    1521
 496  Ile Lys Gly Gly Gly His His His His His His End    507
```

[Figure 28-1]

```
1    ATG GAC ATG AGG GTC CCC GCT CAG CTC CTG GGG CTC CTT CTG CTT    45
1    Met Asp Met Arg Val Pro Ala Gln Leu Leu Gly Leu Leu Leu Leu    15

46   TGG TTC CCA GGC GCC AGA TGT AAT ATT CAG ATG ACC CAG TCA CCG    90
16   Trp Phe Pro Gly Ala Arg Cys Asn Ile Gln Met Thr Gln Ser Pro    30

91   AGC TCA CTG GCA GTT AGT GCC GGC GAA AAA GTT ACC ATG AGC TGT    135
31   Ser Ser Leu Ala Val Ser Ala Gly Glu Lys Val Thr Met Ser Cys    45

136  AAA AGC AGC CAT GCA GTT CTG TAT AGC AGC AAC CAG AAA AAC TAT    180
46   Lys Ser Ser His Ala Val Leu Tyr Ser Ser Asn Gln Lys Asn Tyr    60

181  CTG GCA TGG TAC CAG CAG AAG CCG GGT CAG AGC CCG AAA CTG CTG    225
61   Leu Ala Trp Tyr Gln Gln Lys Pro Gly Gln Ser Pro Lys Leu Leu    75

226  ATT TAT TGG GCC AGC ACC CGC GAT AGC GGT GTT CCG GAT CGC TTT    270
76   Ile Tyr Trp Ala Ser Thr Arg Asp Ser Gly Val Pro Asp Arg Phe    90

271  ACC GGT GGT GGT AGC GGC ACC GAT TTT ACC CTG ACC ATT ACC AAT    315
91   Thr Gly Gly Gly Ser Gly Thr Asp Phe Thr Leu Thr Ile Thr Asn    105

316  ATT CAG CCG GAA GAT CTG GCA GTC TAT TAT TGT CAT CAG TAT TTA    360
106  Ile Gln Pro Glu Asp Leu Ala Val Tyr Tyr Cys His Gln Tyr Leu    120

361  AGC AGC TGG ACC TTT GGT GGT GGC ACC AAA GTT GAA ATC AAG CGA    405
121  Ser Ser Trp Thr Phe Gly Gly Gly Thr Lys Val Glu Ile Lys Arg    135

406  ACT GTG GCT GCA CCA TCT GTC TTC ATC TTC CCG CCA TCT GAT GAG    450
136  Thr Val Ala Ala Pro Ser Val Phe Ile Phe Pro Pro Ser Asp Glu    150

451  CAG TTG AAA TCT GGA ACT GCC TCT GTT GTG TGC CTG CTG AAT AAC    495
151  Gln Leu Lys Ser Gly Thr Ala Ser Val Val Cys Leu Leu Asn Asn    165

496  TTC TAT CCC AGA GAG GCC AAA GTA CAG TGG AAG GTG GAT AAC GCC    540
166  Phe Tyr Pro Arg Glu Ala Lys Val Gln Trp Lys Val Asp Asn Ala    180
```

[Figure 28-2]

```
541  CTC CAA TCG GGT AAC TCC CAG GAG AGT GTC ACA GGG CAG GAC AGC  585
181  Leu Gln Ser Gly Asn Ser Gln Glu Ser Val Thr Gly Gln Asp Ser  195

586  AAG GAC AGC ACC TAC AGC CTC AGC AGC ACT CTG GCG CTG AGC AAA  630
196  Lys Asp Ser Thr Tyr Ser Leu Ser Ser Thr Leu Ala Leu Ser Lys  210

631  GCA GAC TAC GAG AAA CAC AAA GTC TAC GCC TGC GAA GTC ACC CAT  675
211  Ala Asp Tyr Glu Lys His Lys Val Tyr Ala Cys Glu Val Thr His  225

676  CAG GGC CTG AGC TCG CCC GTC ACA AAG AGC TTC AAC AGG GGA GAG  720
226  Gln Gly Leu Ser Ser Pro Val Thr Lys Ser Phe Asn Arg Gly Glu  240

721  TGT TGA  726
241  Cys End  242
```

[Figure 29]

Staining of cell lines with anti-B7-H4 antibody (clone #25) and anti B7-H4 × anti-CD3 (Fab-scFv)

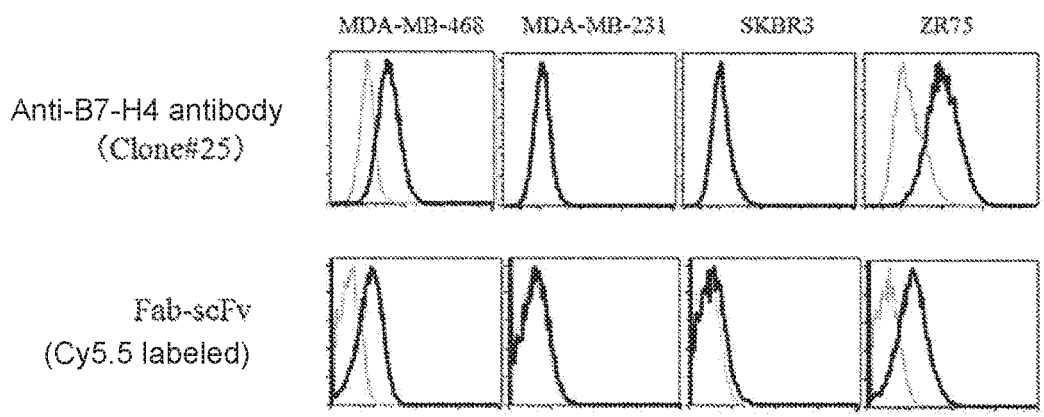

[Figure 30]
Bispecific antibody, 50% Effective Concentration (EC$_{50}$) Measurement (Brest cancer cell line MDA-MB-468/fresh human peripheral blood mononuclear cell)
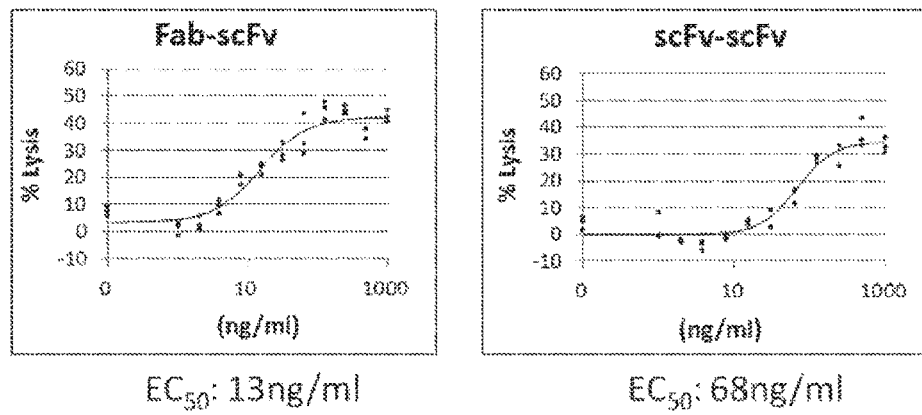
[Figure 31]
Cancer cell line/human peripheral blood mononuclear cell/Fab-scFv
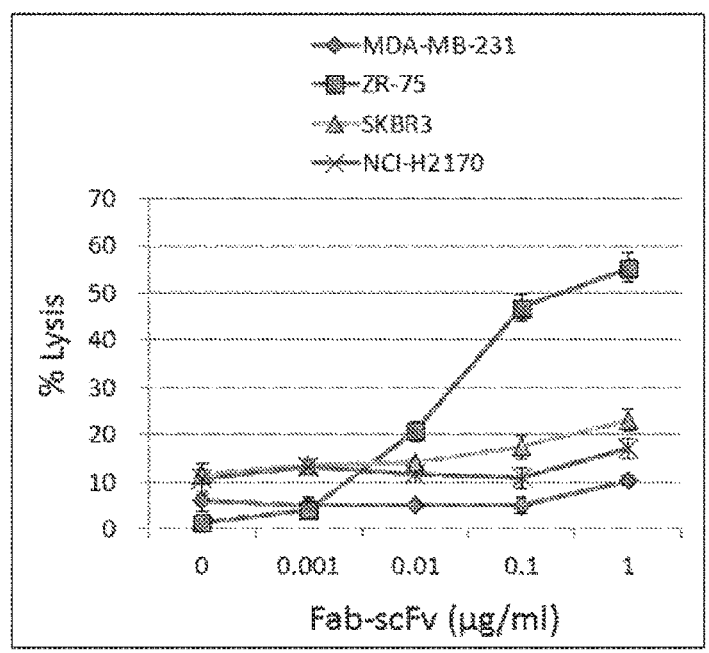

[Figure 32]
Administration of bispecific antibody to murine model co-transplanted human peripheral blood mononuclear cell and human tumor line
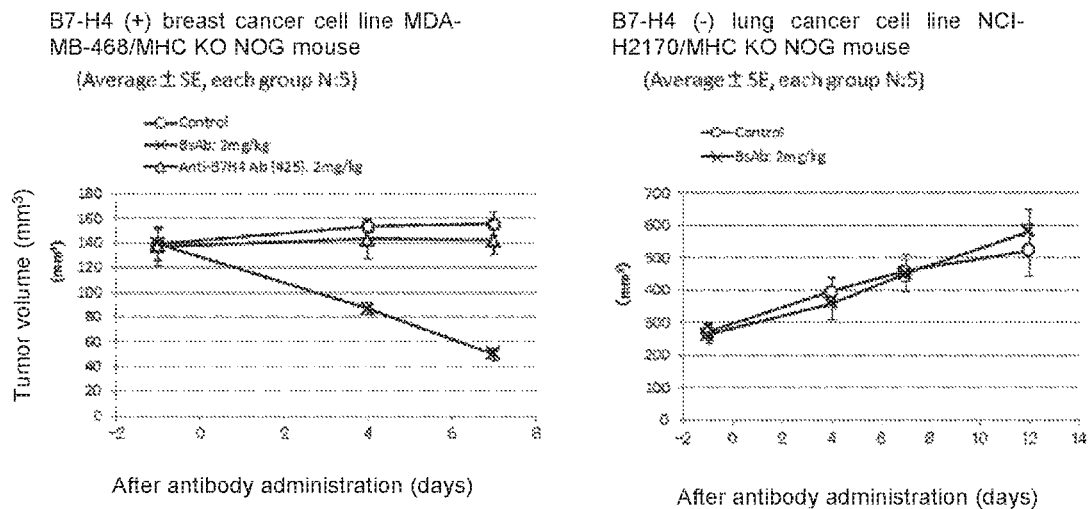
[Figure 33]
Administration of bispecific antibody, effect on transplanted tumor in mouse
MHC-KO-NOG mouse/human peripheral blood mononuclear cell/breast cancer cell line MDA-MB-468 transplanted model
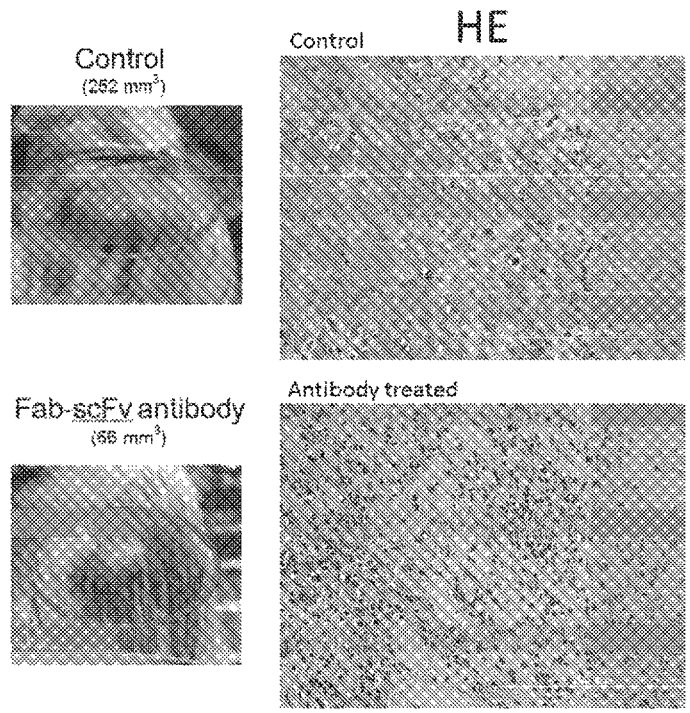

[Figure 34]
Administration of bispecific antibody, effect on transplanted tumor in mouse
MHC-KO-NOG mouse/human peripheral blood mononuclear cell/breast cancer cell line MDA-MB-468 transplanted model
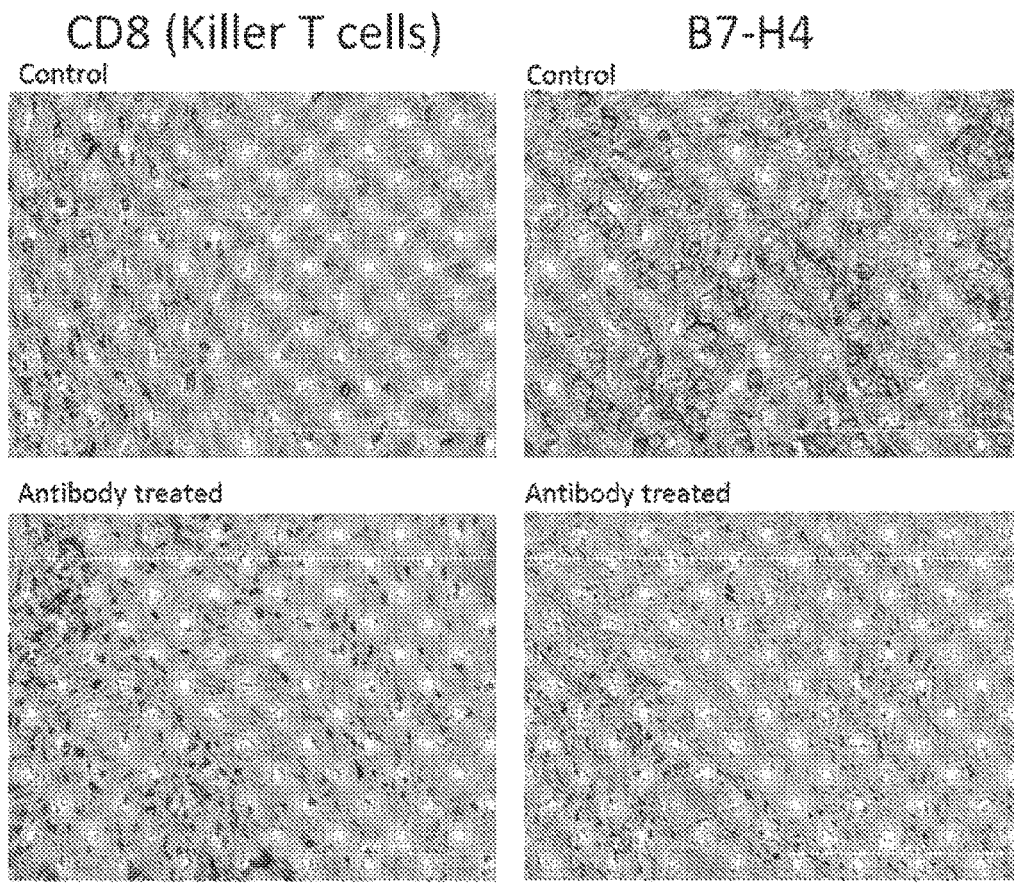

[Figure 35]
(Breast cancer cell single transplanted mouse model)
Administration of fluorescence labeled anti-B7-H4 × anti-CD3 bispecific antibody, mouse fluorescence imaging
① Cy5.5 labelled Fab-scFv administration: 5 µg/body
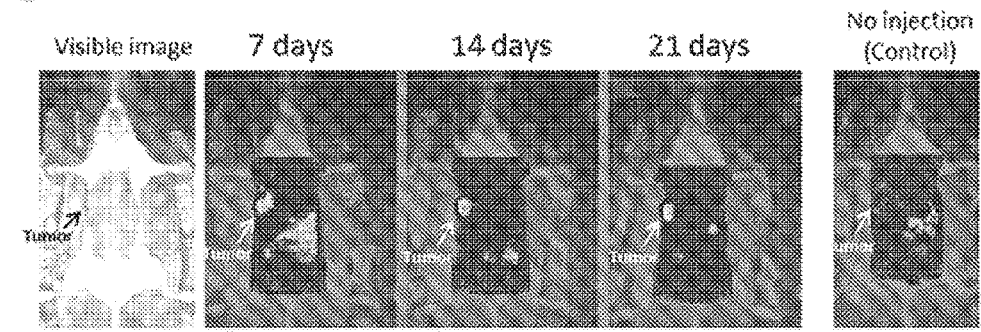
② Cy5.5 labelled Fab-scFv administration: 200 µg/body
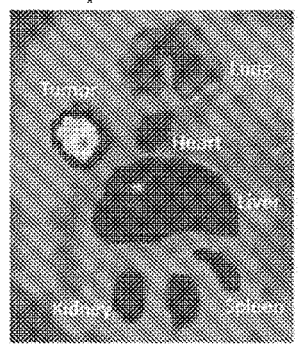
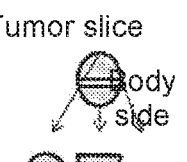
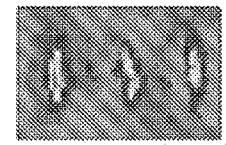
(Fluorescence overlay)
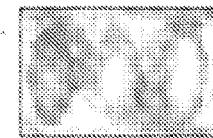
(Visible image)

SEQUENCE LISTING

```
<160> NUMBER OF SEQ ID NOS: 41

<210> SEQ ID NO 1
<211> LENGTH: 342
<212> TYPE: DNA
<213> ORGANISM: Mus musculus
<220> FEATURE:
<221> NAME/KEY: misc_feature
<223> OTHER INFORMATION: Inventor: AKIYAMA, Yasuto; IIZUKA Akira
```

<400> SEQUENCE: 1

```
gaagtgaagc tggtggagtc tgggggaggc ttagtgaagc ctggagggtc cctgaaactc    60
tcctgtgcag cctctggatt cactttcagt agctatgcca tgtcttgggt tcgccagact   120
ccggagaaga ggctggagtg ggtcgcaacc attagtagtg gtggtaatta cacctactat   180
ccagacagtg tgaagggtcg attcaccatc tccagagaca atgccaagaa caccctgtac   240
ctgcaaatga gcagtctgag gtctgaggac acggccatgt attactgtgc aagacatcgg   300
tacgataata actacgatta ctatgctatg gactactggg gt                     342
```

<210> SEQ ID NO 2
<211> LENGTH: 114
<212> TYPE: PRT
<213> ORGANISM: Mus musculus

<400> SEQUENCE: 2

```
Glu Val Lys Leu Val Glu Ser Gly Gly Gly Leu Val Lys Pro Gly Gly
1               5                   10                  15
Ser Leu Lys Leu Ser Cys Ala Ala Ser Gly Phe Thr Phe Ser Ser Tyr
            20                  25                  30
Ala Met Ser Trp Val Arg Gln Thr Pro Glu Lys Arg Leu Glu Trp Val
        35                  40                  45
Ala Thr Ile Ser Gly Gly Asn Tyr Thr Tyr Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Arg Ser Glu Asp Thr Ala Met Tyr Tyr Cys
                85                  90                  95
Ala Arg His Arg Tyr Asp Asn Asn Tyr Asp Tyr Tyr Ala Met Asp Tyr
            100                 105                 110
Trp Gly
```

<210> SEQ ID NO 3
<211> LENGTH: 333
<212> TYPE: DNA
<213> ORGANISM: Mus musculus

<400> SEQUENCE: 3

```
gagttccagc tgcagcagtc tggacctgag ctggtaaagc ctggggcttc agtgaagatg    60
tcctgcaagg cttctggata catattcacc agctatgttg tgcactgggt gaagcagaag   120
cctgggcagg gccttgagtg gattggatat attaatcctt acaatgatgg aactaagtac   180
agtgaaaagt tcaaaggcaa ggccacactg acctcagaca atcctccag cacagcctac   240
atggagctca gcagtctgac ctctgatgac tctgcggtct attattgtgc aagagatggt   300
gtctacgggt accatgctat ggactgctgg ggt                               333
```

<210> SEQ ID NO 4
<211> LENGTH: 111
<212> TYPE: PRT
<213> ORGANISM: Mus musculus

<400> SEQUENCE: 4

```
Glu Phe Gln Leu Gln Gln Ser Gly Pro Glu Leu Val Lys Pro Gly Ala
1               5                   10                  15
Ser Val Lys Met Ser Cys Lys Ala Ser Gly Tyr Ile Phe Thr Ser Tyr
            20                  25                  30
```

```
Val Val His Trp Val Lys Gln Lys Pro Gly Gln Gly Leu Glu Trp Ile
        35                  40                  45

Gly Tyr Ile Asn Pro Tyr Asn Asp Gly Thr Lys Tyr Ser Glu Lys Phe
    50                  55                  60

Lys Gly Lys Ala Thr Leu Thr Ser Asp Lys Ser Ser Thr Ala Tyr
 65                 70                  75                  80

Met Glu Leu Ser Ser Leu Thr Ser Asp Asp Ser Ala Val Tyr Tyr Cys
                85                  90                  95

Ala Arg Asp Gly Val Tyr Gly Tyr His Ala Met Asp Cys Trp Gly
            100                 105                 110

<210> SEQ ID NO 5
<211> LENGTH: 312
<212> TYPE: DNA
<213> ORGANISM: Mus musculus

<400> SEQUENCE: 5
aacattatga tgacacagtc gccatcatct ctggctgtgt ctgcaggaga aaaggtcact      60
atgagctgta agtccagtca tgctgtttta tacagttcaa atcagaagaa ctacttggcc    120
tggtaccagc agaaaccagg gcagtctcct aaactactga tatactgggc atccactagg    180
gattctggtg tccctgatcg cttcacaggc ggtggatctg ggacagattt tactcttacc    240
atcaccaata ttcaacctga agacctggca gtttattact gtcatcaata cctctcctcg    300
tggacgttcg gt                                                        312

<210> SEQ ID NO 6
<211> LENGTH: 104
<212> TYPE: PRT
<213> ORGANISM: Mus musculus

<400> SEQUENCE: 6

Asn Ile Met Met Thr Gln Ser Pro Ser Ser Leu Ala Val Ser Ala Gly
 1               5                   10                  15

Glu Lys Val Thr Met Ser Cys Lys Ser Ser His Ala Val Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Asp Ser Gly Val
        50                  55                  60

Pro Asp Arg Phe Thr Gly Gly Gly Ser Gly Thr Asp Phe Thr Leu Thr
 65                 70                  75                  80

Ile Thr Asn Ile Gln Pro Glu Asp Leu Ala Val Tyr Tyr Cys His Gln
                85                  90                  95

Tyr Leu Ser Ser Trp Thr Phe Gly
            100

<210> SEQ ID NO 7
<211> LENGTH: 318
<212> TYPE: DNA
<213> ORGANISM: Mus musculus

<400> SEQUENCE: 7
caggctgttg tgactcagga atctgcactc accacatcac ctggtgaaac agtcacactc     60
acttgtcgct caagtactgg ggctgttaca actagtaact atgccaactg ggtccaagag   120
aaaccagatc atttattcac tggtctaata ggtggtacca cgaccgagc tccaggtgtt   180
```

```
cctgccagat tctcaggctc cctgattgga gacaaggctg ccctcaccat cacaggggca    240
cagactgagg atgaggcaat atatttctgt gctctatggt acagcaacca tttccacaat    300
gacatgtgta gatgggga                                                  318
```

<210> SEQ ID NO 8
<211> LENGTH: 106
<212> TYPE: PRT
<213> ORGANISM: Mus musculus

<400> SEQUENCE: 8

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asp Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Phe His Asn Asp Met Cys Arg Trp Gly
            100                 105
```

<210> SEQ ID NO 9
<211> LENGTH: 324
<212> TYPE: DNA
<213> ORGANISM: Mus musculus

<400> SEQUENCE: 9

```
gaggttcagc tgcagcagtc tggggcagag cttgtgaggt caggggcctc agtcaagttg     60
tcctgcacag cttctggctt caacattaaa gacttctatg tacactgggt gaagcagagg    120
cctgaacagg gcctggagtg gattggatgg attgatcctg cgcatgttga tactgaatat    180
gcccctaagt tcagggcaa gaccactatg actgcagaca catcctccaa cacagcctac    240
ctgcagctca gcagcctgac atctgaagac tctgccgtct attactgtaa tgccctccta    300
ccacggacta tggactactg gggt                                           324
```

<210> SEQ ID NO 10
<211> LENGTH: 108
<212> TYPE: PRT
<213> ORGANISM: Mus musculus

<400> SEQUENCE: 10

```
Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Phe
            20                  25                  30

Tyr Val His Trp Val Lys Gln Arg Pro Glu Gln Gly Leu Glu Trp Ile
        35                  40                  45

Gly Trp Ile Asp Pro Ala His Val Asp Thr Glu Tyr Ala Pro Lys Phe
    50                  55                  60

Gln Gly Lys Thr Thr Met Thr Ala Asp Thr Ser Ser Asn Thr Ala Tyr
65                  70                  75                  80
```

Leu Gln Leu Ser Ser Leu Thr Ser Glu Asp Ser Ala Val Tyr Tyr Cys
                85                  90                  95

Asn Ala Leu Leu Pro Arg Thr Met Asp Tyr Trp Gly
            100                 105

<210> SEQ ID NO 11
<211> LENGTH: 312
<212> TYPE: DNA
<213> ORGANISM: Mus musculus

<400> SEQUENCE: 11

```
gatgttgttc tgacccaaac tccactctct ctgcctgtca atgttggaga tcaagcctct      60
atctcctgca agtctactaa gagtcttctg aatagtgatg gattcactta tttggactgg     120
tatttgcaga agccaggcca gtctccacag ctcctaatat atttggtttc taatcgattt     180
tctggagttc cagacaggtt cagtggcagt gggtcaggaa cagatttcac actcaagatc     240
agcagagtgg aggctgagga tttgggagtt tattattgct tccagagtaa ctatcttccg     300
tacacgttcg ga                                                        312
```

<210> SEQ ID NO 12
<211> LENGTH: 104
<212> TYPE: PRT
<213> ORGANISM: Mus musculus

<400> SEQUENCE: 12

Asp Val Val Leu Thr Gln Thr Pro Leu Ser Leu Pro Val Asn Val Gly
1               5                   10                  15

Asp Gln Ala Ser Ile Ser Cys Lys Ser Thr Lys Ser Leu Leu Asn Ser
            20                  25                  30

Asp Gly Phe Thr Tyr Leu Asp Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Tyr Thr Phe Gly
            100

<210> SEQ ID NO 13
<211> LENGTH: 324
<212> TYPE: DNA
<213> ORGANISM: Mus musculus

<400> SEQUENCE: 13

```
caggtgcagc tgaaggagtc aggacctggc ctggtggcgc cctcacagag cctgtccatc      60
acatgcaccg tctcagggtt ctcattaact agctatggtg tacactgggt tcgccagcct     120
ccaggaaagg gtctggagtg gctggtagtg atatggagtg atggaagcac aacctataat     180
tcagctctca atccagact gagcatcagc aaggacaact ccaagagcca agttttctta     240
aaaatgaaca gtctccaaac tgatgacaca gccatgtact actgtgccag agagcctccc     300
acgacgtacg tttgcttact gggg                                           324
```

<210> SEQ ID NO 14
<211> LENGTH: 108

<212> TYPE: PRT
<213> ORGANISM: Mus musculus

<400> SEQUENCE: 14

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Glu Pro Pro Thr Thr Tyr Val Cys Leu Leu Gly
            100                 105

<210> SEQ ID NO 15
<211> LENGTH: 312
<212> TYPE: DNA
<213> ORGANISM: Mus musculus

<400> SEQUENCE: 15
gacattgtga tgtcacagtc tccatcctcc ctggctgtgt cagtaggaga gaaggtcacc      60
atgagctgca atccagtca gagtctgctc aacagtagaa cccgaaagag ctatttggct      120
tggtaccagc agaaaccagg gcagtctcct aaactgctga tctactgggc atccactagg     180
gaatctgggg tccctgatcg cttcacaggc agtggatctg ggacagattt cactctcacc     240
atcagcagtg tgcaggctga agacctggca gtttattact gcaagcaatc ttataatctg     300
ctcacgttcg gt                                                         312

<210> SEQ ID NO 16
<211> LENGTH: 104
<212> TYPE: PRT
<213> ORGANISM: Mus musculus

<400> SEQUENCE: 16

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Asn Ser
            20                  25                  30

Arg Thr Arg Lys Ser Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly
            100

<210> SEQ ID NO 17
<211> LENGTH: 318
<212> TYPE: DNA

<213> ORGANISM: Mus musculus

<400> SEQUENCE: 17

```
caggctgttg tgactcagga atctgcactc accacatcac ctggtgaaac agtcacactc    60
acttgtcgct caagtactgg ggctgttaca actagtaact atgccaactg ggtccaagag   120
aaaccagatc atttattcac tggtctaata ggtggtacca acgaccgagc tccaggtgtt   180
cctgccagat tctcaggctc cctgattgga acaaggctg ccctcaccat cacggggca    240
cagactgagg atgaggcaat atatttctgt gctctatggt acagcaacca tttccacaat   300
gacatgtgta gatgggga                                                 318
```

<210> SEQ ID NO 18
<211> LENGTH: 106
<212> TYPE: PRT
<213> ORGANISM: Mus musculus

<400> SEQUENCE: 18

```
Gln Ala Val Val Thr Gln Glu Ser Ala Leu Thr Thr Ser Pro Gly Glu
1               5                   10                  15
Thr Val Thr Leu Thr Cys Arg Ser Ser Thr Gly Ala Val Thr Thr Ser
            20                  25                  30
Asn Tyr Ala Asn Trp Val Gln Glu Lys Pro Asp His Leu Phe Thr Gly
        35                  40                  45
Leu Ile Gly Gly Thr Asn Asp Arg Ala Pro Gly Val Pro Ala Arg Phe
    50                  55                  60
Ser Gly Ser Leu Ile Gly Asp Lys Ala Ala Leu Thr Ile Thr Gly Ala
65                  70                  75                  80
Gln Thr Glu Asp Glu Ala Ile Tyr Phe Cys Ala Leu Trp Tyr Ser Asn
                85                  90                  95
His Phe His Asn Asp Met Cys Arg Trp Gly
            100                 105
```

<210> SEQ ID NO 19
<211> LENGTH: 330
<212> TYPE: DNA
<213> ORGANISM: Mus musculus

<400> SEQUENCE: 19

```
caggttcagc tgcagcagtc tggagctgaa ctgatgaaac tggggcctc agtgaagata    60
tcctgcaagg ctactggcta cacattcagt agctactgga tagagtgggt aaagcagagg   120
cctggacatg gccttgagtg gattggagag atttacatg gaagtgatag tactaactac    180
aatgagaatt tcaagggcaa ggccacattc actgcagata catcctccaa cacagcctac   240
atgcgactca gcagcctgac atctgaggac tctgccgtct attactgtgc aagccattac   300
tacggtagta gccccttgc ttactggggc                                     330
```

<210> SEQ ID NO 20
<211> LENGTH: 110
<212> TYPE: PRT
<213> ORGANISM: Mus musculus

<400> SEQUENCE: 20

```
Gln Val Gln Leu Gln Gln Ser Gly Ala Glu Leu Met Lys Pro Gly Ala
1               5                   10                  15
Ser Val Lys Ile Ser Cys Lys Ala Thr Gly Tyr Thr Phe Ser Ser Tyr
            20                  25                  30
```

Trp Ile Glu Trp Val Lys Gln Arg Pro Gly His Gly Leu Glu Trp Ile
             35                  40                  45

Gly Glu Ile Leu His Gly Ser Asp Ser Thr Asn Tyr Asn Glu Asn Phe
 50                  55                  60

Lys Gly Lys Ala Thr Phe Thr Ala Asp Thr Ser Ser Asn Thr Ala Tyr
 65                  70                  75                  80

Met Arg Leu Ser Ser Leu Thr Ser Glu Asp Ser Ala Val Tyr Tyr Cys
                 85                  90                  95

Ala Ser His Tyr Tyr Gly Ser Ser Pro Phe Ala Tyr Trp Gly
                100                 105                 110

<210> SEQ ID NO 21
<211> LENGTH: 315
<212> TYPE: DNA
<213> ORGANISM: Mus musculus

<400> SEQUENCE: 21
gacattgtga tgtcacagtc tccatcctcc ctagctgtgt cagttggaga aaggttact      60 atgagctgca agtccagtca gagccttta tatagtagta atcaaaagaa ttacttggcc     120
tggtaccagc agaaaccagg gcagtctcct aaactgctga tttactgggc atccactagg    180
gaatctgggg tccctgatcg cttcacaggc agtggatctg gacagattt cactctcacc     240 atcagcagtg tgaaggctga agacctggca gtttattact gtcagcaata ttatagctat    300
ccgctcacgt tcggt                                                     315

<210> SEQ ID NO 22
<211> LENGTH: 105
<212> TYPE: PRT
<213> ORGANISM: Mus musculus

<400> SEQUENCE: 22

Asp Ile Val Met Ser Gln Ser Pro Ser Ser Leu Ala Val Ser Val Gly
  1               5                  10                  15

Glu Lys Val Thr Met Ser Cys Lys Ser Ser Gln Ser Leu Leu Tyr Ser
                 20                  25                  30

Ser Asn Gln Lys Asn Tyr Leu Ala Trp Tyr Gln Lys Pro Gly Gln
             35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Leu Thr Phe Gly
                100                 105

<210> SEQ ID NO 23
<211> LENGTH: 324
<212> TYPE: DNA
<213> ORGANISM: Mus musculus

<400> SEQUENCE: 23
gaggtgcagc tggtggagtc agggggagac ttagtgaagc ctggagggtc cctgaaactc      60
tcctgtgcag cctctggatt cactttcagt acctatggca tgtcttgggt tcgccagact    120
ccagacaaga ggctggagtg ggtcgcaacc attagtagtg gtggtaatta cacctactat    180
ccagacagtg tgaaggggcg attcaccatc tccagagaca atgccaagaa cacctgtac     240

```
ctgcaaatga gcagtctgaa gtctgaggac acagccatgt attactgtgc aagaccgtat    300
ggtaaccact tgactactg gggc                                            324
```

<210> SEQ ID NO 24
<211> LENGTH: 108
<212> TYPE: PRT
<213> ORGANISM: Mus musculus

<400> SEQUENCE: 24

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Thr Tyr
                20                  25                  30

Gly Met Ser Trp Val Arg Gln Thr Pro Asp Lys Arg Leu Glu Trp Val
            35                  40                  45

Ala Thr Ile Ser Ser Gly Gly Asn Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Pro Tyr Gly Asn His Phe Asp Tyr Trp Gly
            100                 105

<210> SEQ ID NO 25
<211> LENGTH: 297
<212> TYPE: DNA
<213> ORGANISM: Mus musculus

<400> SEQUENCE: 25

```
gacatccaga tgactcagtc tccagcctcc ctggctgcat ctgtgggaga aactgtcacc    60
atcacatgtc gagcaagtga gaacatttac tacagtttag catggtatca gcagaagcaa   120
gggaaatctc ctcagctcct gatctataat gcaaacagct tggaagatgg tgtcccatcg   180
aggttcagtg gcagtggatc tgggacacag tattctatga agatcaacag catgcagcct   240
gaagataccg caacttattt ctgtaaacag gcttatgacg ttccgtacac gttcgga      297
```

<210> SEQ ID NO 26
<211> LENGTH: 99
<212> TYPE: PRT
<213> ORGANISM: Mus musculus

<400> SEQUENCE: 26

Asp Ile Gln Met Thr Gln Ser Pro Ala Ser Leu Ala Ala Ser Val Gly
1               5                   10                  15

Glu Thr Val Thr Ile Thr Cys Arg Ala Ser Glu Asn Ile Tyr Tyr Ser
                20                  25                  30

Leu Ala Trp Tyr Gln Gln Lys Gln Gly Lys Ser Pro Gln Leu Leu Ile
            35                  40                  45

Tyr Asn Ala Asn Ser Leu Glu Asp Gly Val Pro Ser Arg Phe Ser Gly
        50                  55                  60

Ser Gly Ser Gly Thr Gln Tyr Ser Met Lys Ile Asn Ser Met Gln Pro
65                  70                  75                  80

Glu Asp Thr Ala Thr Tyr Phe Cys Lys Gln Ala Tyr Asp Val Pro Tyr
                85                  90                  95

Thr Phe Gly

<210> SEQ ID NO 27
<211> LENGTH: 330
<212> TYPE: DNA
<213> ORGANISM: Mus musculus

<400> SEQUENCE: 27

```
gaagtgaagc tggtggagtc tgggggaggc ttagtgaagc ctggagggtc cctgaaactc      60
tcctgtgcag cctctggatt cactttcagt aactatgcct tgtcttgggt tcgccagact     120
ccagaaaaga ggctggagtg gtcgcatcc attagtggtg gtggtagcac ttactatcca     180
gacagtgtga agggccgatt cattatctcc agagataatg ccaggaacat cctgtacctg     240
caaatgagca gtctgaggtc tgaggacacg gccatgtatt actgtgcaag aggcccctcc     300
tatgatgatt actacttcga tgtctggggc                                      330
```

<210> SEQ ID NO 28
<211> LENGTH: 110
<212> TYPE: PRT
<213> ORGANISM: Mus musculus

<400> SEQUENCE: 28

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Leu Ser Trp Val Arg Gln Thr Pro Glu Lys Arg Leu Glu Trp Val
        35                  40                  45

Ala Ser Ile Ser Gly Gly Gly Ser Thr Tyr Tyr Pro Asp Ser Val Lys
    50                  55                  60

Gly Arg Phe Ile Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Gly Pro Ser Tyr Asp Asp Tyr Tyr Phe Asp Val Trp Gly
            100                 105                 110
```

<210> SEQ ID NO 29
<211> LENGTH: 312
<212> TYPE: DNA
<213> ORGANISM: Mus musculus

<400> SEQUENCE: 29

```
gatgttgtga tgacccagac tccactcact ttgtcggtta ccattggaca accagcctcc      60
atctcttgca gtcaagtca gagcctctta gatagtgctg gaaagacata tttgaattgg     120
ttgttacaga ggccaggcca gtctccaaag cgcctaattt acctggtgtc taaactggac     180
tctggagtcc ctgacaggtt cactggcagt ggatcaggga cagatttcac tctgaaaatc     240
agcagtctgc aggctgagga tttgggaatt tattattgct ggcaaggtac acatttttcct     300 ctcacgttcg gt                                                         312
```

<210> SEQ ID NO 30
<211> LENGTH: 104
<212> TYPE: PRT
<213> ORGANISM: Mus musculus

<400> SEQUENCE: 30

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Ala Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Ser Leu Gln Ala Glu Asp Leu Gly Ile Tyr Tyr Cys Trp Gln Gly
                85                  90                  95

Thr His Phe Pro Leu Thr Phe Gly
            100
```

<210> SEQ ID NO 31
<211> LENGTH: 1500
<212> TYPE: DNA
<213> ORGANISM: Artificial
<220> FEATURE:
<223> OTHER INFORMATION: Mus musculus, Synthesized sequence

<400> SEQUENCE: 31

```
atggaagccc cagctcagct tctcttcctc ctgctactct ggctcccaga taccaccgga      60
aacattatga tgacacagtc gccatcatct ctggctgtgt ctgcaggaga aaaggtcact     120
atgagctgta gtccagtca tgctgtttta tacagttcaa atcagaagaa ctacttggcc     180
tggtaccagc agaaaccagg gcagtctcct aaactactga tatactgggc atccactagg     240
gattctggtg tccctgatcg cttcacaggc ggtggatctg ggacagattt tactcttacc     300
atcaccaata ttcaacctga agacctggca gtttattact gtcatcaata cctctcctcg     360
tggacgttcg gaggcggtgg gtcaggcggt ggagggtctg gtggaggcgg ttcggagttc     420
cagctgcagc agtctggacc tgagctggta agcctgggg cttcagtgaa gatgtcctgc     480
aaggcttctg gatacatatt caccagctat gttgtgcact gggtgaagca gaagcctggg     540
cagggccttg agtggattgg atatattaat ccttacaatg atggaactaa gtacagtgaa     600
aagttcaaag gcaaggccac actgacctca gacaaatcct ccagcacagc ctacatggag     660
ctcagcagtc tgacctctga tgactctgcg gtctattatt gtgcaagaga tggtgtctac     720
gggtaccatg ctatggactg ctggggtcaa ggagagccca atcttcaga caaaactcac     780
acatcaccac cgtcaccagc tcaggtccag ctgcagcagt ctggggctga actggcaaga     840
cctggggcct cagtgaagat gtcctgcaag gcttctggct acacctttac taggtacacg     900
atgcactggg taaaacagag gcctggacag ggtctggaat ggattggata cattaatcct     960
agccgtggtt atactaatta caatcagaag ttcaaggaca aggccacatt gactacagac    1020
aaatcctcca gcacagccta catgcaactg agcagcctga tctgagga ctctgcagtc    1080
tattactgtg caagatatta tgatgatcat tactgccttg actactgggg tgcggaggt    1140
tcaggaggtg gcggatctgg tggcggaggc tcgcaaattg ttctcaccca gtctccagca    1200
atcatgtctg catctccagg ggagaaggtc accatgacct gcagtgccag ctcaagtgta    1260
agttacatga actggtacca gcagaagtca ggcacctccc ccaaaagatg gatttatgac    1320
acatccaaac tggcttctgg agtccctgct cacttcaggg gcagtgggtc tgggacctct    1380
```

```
tactctctca caatcagcgg catggaggct gaagatgctg ccacttatta ctgccagcag      1440
tggagtagta acccattcac gttcggctcg ggaggcggtc accaccacca ccaccactga     1500
```

<210> SEQ ID NO 32
<211> LENGTH: 499
<212> TYPE: PRT
<213> ORGANISM: Artificial
<220> FEATURE:
<223> OTHER INFORMATION: Mus musculus, Synthesized sequence

<400> SEQUENCE: 32

```
Met Glu Ala Pro Ala Gln Leu Leu Phe Leu Leu Leu Leu Trp Leu Pro
1               5                   10                  15

Asp Thr Thr Gly Asn Ile Met Met Thr Gln Ser Pro Ser Ser Leu Ala
            20                  25                  30

Val Ser Ala Gly Glu Lys Val Thr Met Ser Cys Lys Ser Ser His Ala
        35                  40                  45

Val Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Asp Ser Gly Val Pro Asp Arg Phe Thr Gly Gly Ser Gly Thr Asp
                85                  90                  95

Phe Thr Leu Thr Ile Thr Asn Ile Gln Pro Glu Asp Leu Ala Val Tyr
            100                 105                 110

Tyr Cys His Gln Tyr Leu Ser Ser Trp Thr Phe Gly Gly Gly Gly Ser
        115                 120                 125

Gly Gly Gly Gly Ser Gly Gly Gly Ser Glu Phe Gln Leu Gln Gln
    130                 135                 140

Ser Gly Pro Glu Leu Val Lys Pro Gly Ala Ser Val Lys Met Ser Cys
145                 150                 155                 160

Lys Ala Ser Gly Tyr Ile Phe Thr Ser Tyr Val Val His Trp Val Lys
                165                 170                 175

Gln Lys Pro Gly Gln Gly Leu Glu Trp Ile Gly Tyr Ile Asn Pro Tyr
            180                 185                 190

Asn Asp Gly Thr Lys Tyr Ser Glu Lys Phe Lys Gly Lys Ala Thr Leu
        195                 200                 205

Thr Ser Asp Lys Ser Ser Ser Thr Ala Tyr Met Glu Leu Ser Ser Leu
    210                 215                 220

Thr Ser Asp Asp Ser Ala Val Tyr Tyr Cys Ala Arg Asp Gly Val Tyr
225                 230                 235                 240

Gly Tyr His Ala Met Asp Cys Trp Gly Gln Gly Glu Pro Lys Ser Ser
                245                 250                 255

Asp Lys Thr His Thr Ser Pro Pro Ser Pro Ala Gln Val Gln Leu Gln
            260                 265                 270

Gln Ser Gly Ala Glu Leu Ala Arg Pro Gly Ala Ser Val Lys Met Ser
        275                 280                 285

Cys Lys Ala Ser Gly Tyr Thr Phe Thr Arg Tyr Thr Met His Trp Val
    290                 295                 300

Lys Gln Arg Pro Gly Gln Gly Leu Glu Trp Ile Gly Tyr Ile Asn Pro
305                 310                 315                 320

Ser Arg Gly Tyr Thr Asn Tyr Asn Gln Lys Phe Lys Asp Lys Ala Thr
                325                 330                 335
```

```
Leu Thr Thr Asp Lys Ser Ser Thr Ala Tyr Met Gln Leu Ser Ser
            340                 345                 350

Leu Thr Ser Glu Asp Ser Ala Val Tyr Tyr Cys Ala Arg Tyr Tyr Asp
        355                 360                 365

Asp His Tyr Cys Leu Asp Tyr Trp Gly Gly Gly Ser Gly Gly Gly
    370                 375                 380

Gly Ser Gly Gly Gly Ser Gln Ile Val Leu Thr Gln Ser Pro Ala
385                 390                 395                 400

Ile Met Ser Ala Ser Pro Gly Glu Lys Val Thr Met Thr Cys Ser Ala
                405                 410                 415

Ser Ser Ser Val Ser Tyr Met Asn Trp Tyr Gln Gln Lys Ser Gly Thr
            420                 425                 430

Ser Pro Lys Arg Trp Ile Tyr Asp Thr Ser Lys Leu Ala Ser Gly Val
        435                 440                 445

Pro Ala His Phe Arg Gly Ser Gly Ser Gly Thr Ser Tyr Ser Leu Thr
    450                 455                 460

Ile Ser Gly Met Glu Ala Glu Asp Ala Ala Thr Tyr Tyr Cys Gln Gln
465                 470                 475                 480

Trp Ser Ser Asn Pro Phe Thr Phe Gly Ser Gly Gly His His His
                485                 490                 495

His His His

<210> SEQ ID NO 33
<211> LENGTH: 282
<212> TYPE: PRT
<213> ORGANISM: Homo sapiens

<400> SEQUENCE: 33

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205
```

```
Lys Val Val Ser Val Leu Tyr Asn Val Thr Ile Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
                260                 265                 270

Leu Pro Leu Ser Pro Tyr Leu Met Leu Lys
            275                 280
```

<210> SEQ ID NO 34
<211> LENGTH: 290
<212> TYPE: PRT
<213> ORGANISM: Homo sapiens

<400> SEQUENCE: 34

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270
```

Gly Ile Gln Asp Thr Asn Ser Lys Lys Gln Ser Asp Thr His Leu Glu
        275                 280                 285

Glu Thr
    290

<210> SEQ ID NO 35
<211> LENGTH: 273
<212> TYPE: PRT
<213> ORGANISM: Homo sapiens

<400> SEQUENCE: 35

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile

<210> SEQ ID NO 36
<211> LENGTH: 1602
<212> TYPE: DNA
<213> ORGANISM: Artificial
<220> FEATURE:
<223> OTHER INFORMATION: Mus musculus (codon-optimized), Synthesized
      sequence

<400> SEQUENCE: 36

```
atggacatga gggtccccgc tcagctcctg gggctccttc tgctttggtt cccaggcgcc      60
agatgtaata ttcagatgac ccagtcaccg agctcactgg cagttagtgc cggcgaaaaa     120
gttaccatga gctgtaaaag cagccatgca gttctgtata gcagcaacca gaaaaactat     180
ctggcatggt accagcagaa gccgggtcag agcccgaaac tgctgattta ttgggccagc     240
acccgcgata gcggtgttcc ggatcgcttt accggtggtg gtagcggcac cgattttacc     300
ctgaccatta ccaatattca gccggaagat ctggcagtgt attattgtca tcagtattta     360
agcagctgga cctttggtgg tggcaccaaa gttgaaatca aggaggctc aggaggcggt     420
gggtctggtg ggcggatc gggcggagaa tttcagctgc aacagagcgg tccggagctg     480
gttaaaccgg cgcaagcgt taaaatgagc tgcaaagcaa gcggttatat ctttaccagc     540
tatgttgttc attgggtgaa acagaaacct ggccaaggtc tggagtggat tggttatatc     600
aatccgtata tgacggcac caaatacagc gaaaaattca aggtaaagc aaccctgacc     660
tccgataaaa gcagtagcac cgcatatatg aactgagca gtctgaccag tgatgatagc     720
gcagtttatt actgtgcacg cgatggtgtt tatggttatc atgcaatgga ttgctggggt     780
cagggcacca gcgttaccgt tagcagtgga ggttctggag gtggcgggtc cggcggggt     840
ggatcaggtg acaggtgca actgcaacag tcaggtgccg aactggcacg cccgggtgcc     900
tcagttaaaa tgtcatgtaa agcaagtggc tataccttca cacgctatac catgcactgg     960
gttaaacagc gcccaggtca gggcttagaa tggatcggct atattaaccc gagccgcggt    1020
tataccaatt acaaccagaa gtttaagac aaagccacac tgaccacaga taaatcaagc    1080
tcaaccgcct atatgcagct gtcaagcctt accagcgaag attctgcagt atactattgt    1140
gcccgctatt atgatgatca ctattgcctg gattattggg gacaaggtac gaccctgacc    1200
gtttcaagtg agggtcggg agggggtggc tcaggtggcg gaggatccgg agggcagatt    1260
gttctgaccc agagtccggc aattatgagc gcaagtccgg gtgagaaagt gacaatgacc    1320
tgtagcgcaa gcagcagcgt tagctatatg aattggtacc aacaaaaag cggcaccagt    1380
ccgaaacgct ggatttatga taccagcaaa ctggcaagtg gcgttccggc acattttcgc    1440
ggttcaggca gcggtacaag ctatagcctg acaattagcg gtatggaagc agaagatgca    1500
gcaacctatt actgccagca gtggtcaagc aatccgttta catttggttc aggcacgaaa    1560
ctggaaatta aggtggtgg tcatcatcac caccatcact aa                        1602
```

<210> SEQ ID NO 37
<211> LENGTH: 533
<212> TYPE: PRT
<213> ORGANISM: Artificial
<220> FEATURE:
<223> OTHER INFORMATION: Mus musculus, Synthesized sequence

<400> SEQUENCE: 37

```
Met Asp Met Arg Val Pro Ala Gln Leu Leu Gly Leu Leu Leu Leu Trp
1               5                   10                  15

Phe Pro Gly Ala Arg Cys Asn Ile Gln Met Thr Gln Ser Pro Ser Ser
            20                  25                  30

Leu Ala Val Ser Ala Gly Glu Lys Val Thr Met Ser Cys Lys Ser Ser
        35                  40                  45

His Ala Val Leu Tyr Ser Ser Asn Gln Lys Asn Tyr Leu Ala Trp Tyr
    50                  55                  60
```

-continued

```
Gln Gln Lys Pro Gly Gln Ser Pro Lys Leu Leu Ile Tyr Trp Ala Ser
 65                  70                  75                  80

Thr Arg Asp Ser Gly Val Pro Asp Arg Phe Thr Gly Gly Gly Ser Gly
                 85                  90                  95

Thr Asp Phe Thr Leu Thr Ile Thr Asn Ile Gln Pro Glu Asp Leu Ala
            100                 105                 110

Val Tyr Tyr Cys His Gln Tyr Leu Ser Ser Trp Thr Phe Gly Gly Gly
        115                 120                 125

Thr Lys Val Glu Ile Lys Gly Gly Ser Gly Gly Gly Ser Gly Gly
    130                 135                 140

Gly Gly Ser Gly Gly Glu Phe Gln Leu Gln Gln Ser Gly Pro Glu Leu
145                 150                 155                 160

Val Lys Pro Gly Ala Ser Val Lys Met Ser Cys Lys Ala Ser Gly Tyr
                165                 170                 175

Ile Phe Thr Ser Tyr Val Val His Trp Val Lys Gln Lys Pro Gly Gln
            180                 185                 190

Gly Leu Glu Trp Ile Gly Tyr Ile Asn Pro Tyr Asn Asp Gly Thr Lys
        195                 200                 205

Tyr Ser Glu Lys Phe Lys Gly Lys Ala Thr Leu Thr Ser Asp Lys Ser
    210                 215                 220

Ser Ser Thr Ala Tyr Met Glu Leu Ser Ser Leu Thr Ser Asp Asp Ser
225                 230                 235                 240

Ala Val Tyr Tyr Cys Ala Arg Asp Gly Val Tyr Gly Tyr His Ala Met
                245                 250                 255

Asp Cys Trp Gly Gln Gly Thr Ser Val Thr Val Ser Ser Gly Gly Ser
            260                 265                 270

Gly Gly Gly Gly Ser Gly Gly Gly Ser Gly Gly Gln Val Gln Leu
        275                 280                 285

Gln Gln Ser Gly Ala Glu Leu Ala Arg Pro Gly Ala Ser Val Lys Met
    290                 295                 300

Ser Cys Lys Ala Ser Gly Tyr Thr Phe Thr Arg Tyr Thr Met His Trp
305                 310                 315                 320

Val Lys Gln Arg Pro Gly Gln Gly Leu Glu Trp Ile Gly Tyr Ile Asn
                325                 330                 335

Pro Ser Arg Gly Tyr Thr Asn Tyr Asn Gln Lys Phe Lys Asp Lys Ala
            340                 345                 350

Thr Leu Thr Thr Asp Lys Ser Ser Ser Thr Ala Tyr Met Gln Leu Ser
        355                 360                 365

Ser Leu Thr Ser Glu Asp Ser Ala Val Tyr Tyr Cys Ala Arg Tyr Tyr
    370                 375                 380

Asp Asp His Tyr Cys Leu Asp Tyr Trp Gly Gln Gly Thr Thr Leu Thr
385                 390                 395                 400

Val Ser Ser Gly Gly Ser Gly Gly Gly Ser Gly Gly Gly Ser
                405                 410                 415

Gly Gly Gln Ile Val Leu Thr Gln Ser Pro Ala Ile Met Ser Ala Ser
        420                 425                 430

Pro Gly Glu Lys Val Thr Met Thr Cys Ser Ala Ser Ser Ser Val Ser
    435                 440                 445

Tyr Met Asn Trp Tyr Gln Gln Lys Ser Gly Thr Ser Pro Lys Arg Trp
450                 455                 460

Ile Tyr Asp Thr Ser Lys Leu Ala Ser Gly Val Pro Ala His Phe Arg
465                 470                 475                 480
```

Gly Ser Gly Ser Gly Thr Ser Tyr Ser Leu Thr Ile Ser Gly Met Glu
            485                 490                 495

Ala Glu Asp Ala Ala Thr Tyr Tyr Cys Gln Gln Trp Ser Ser Asn Pro
        500                 505                 510

Phe Thr Phe Gly Ser Gly Thr Lys Leu Glu Ile Lys Gly Gly Gly His
        515                 520                 525

His His His His His
        530

<210> SEQ ID NO 38
<211> LENGTH: 1521
<212> TYPE: DNA
<213> ORGANISM: Artificial
<220> FEATURE:
<223> OTHER INFORMATION: Mus musculus (codon-optimized), Homo sapiens,
      Synthesized sequence

<400> SEQUENCE: 38

| | | | | | |
|---|---|---|---|---|---|
| atggagttgg | ggctgtgctg | ggttttcctt | gttgctattt | taaaaggtgt | ccagtgtgaa | 60 |
| gtgcagctgc | aacagagcgg | tccggagctg | gttaaaccgg | cgcaagcgt | taaaatgagc | 120 |
| tgcaaagcaa | gcggttatat | ctttaccagc | tatgttgttc | attgggtgaa | acagaaacct | 180 |
| ggccaaggtc | tggagtggat | tggttatatc | aatccgtata | atgacggcac | caaatacagc | 240 |
| gaaaaattca | aggtaaagc | aaccctgacc | tccgataaaa | gcagtagcac | cgcatatatg | 300 |
| gaactgagca | gtctgaccag | tgatgatagc | gcagtttatt | actgtgcacg | cgatggtgtt | 360 |
| tatggttatc | atgcaatgga | ttgctggggt | cagggcacca | cgttaccgt | tagcagtgca | 420 |
| tccaccaagg | gcccatcggt | cttcccctg | cgccctgct | ccaggagcac | ctccgagagc | 480 |
| acagccgccc | tgggctgcct | ggtcaaggac | tacttccccg | aaccggtgac | ggtgtcgtgg | 540 |
| aactcaggcg | ccctgaccag | cggcgtgcac | accttcccgg | ctgtcctaca | gtcctcagga | 600 |
| ctctattccc | tcagcagcgt | ggtgaccgtg | ccctccagca | gcttgggcac | gaagacctac | 660 |
| acctgcaacg | tagatcacaa | gcccagcaac | accaaggtgg | acaagagagt | tgagtccaaa | 720 |
| tatggtggag | ttctggagg | tggcgggtcc | ggcggggtg | gatcaggtgg | acaggtgcaa | 780 |
| ctgcaacagt | caggtgccga | actggcacgc | ccgggtgcct | cagttaaaat | gtcatgtaaa | 840 |
| gcaagtggct | ataccttcac | acgctatacc | atgcactggg | ttaaacagcg | cccaggtcag | 900 |
| ggcttagaat | ggatcggcta | tattaacccg | agccgcggtt | ataccaatta | caaccagaag | 960 |
| tttaaagaca | aagccacact | gaccacagat | aaatcaagct | caaccgccta | tatgcagctg | 1020 |
| tcaagcctta | ccagcgaaga | ttctgcagta | tactattgtg | cccgctatta | tgatgatcac | 1080 |
| tattgcctgg | attattgggg | acaaggtacg | accctgaccg | tttcaagtgg | agggtcggga | 1140 |
| gggggtggct | caggtggcgg | aggatccgga | gggcagattg | ttctgaccca | gagtccggca | 1200 |
| attatgagcg | caagtccggg | tgagaaagtg | acaatgacct | gtagcgcaag | cagcagcgtt | 1260 |
| agctatatga | attggtacca | acaaaaaagc | ggcaccagtc | cgaaacgctg | gatttatgat | 1320 |
| accagcaaac | tggcaagtgg | cgttccggca | cattttcgcg | gttcaggcag | cggtacaagc | 1380 |
| tatagcctga | caattagcgg | tatggaagca | gaagatgcag | caacctatta | ctgccagcag | 1440 |
| tggtcaagca | atccgtttac | atttggttca | ggcacgaaac | tggaaattaa | aggtggtggt | 1500 |
| catcatcacc | accatcacta | a | | | | 1521 |

<210> SEQ ID NO 39
<211> LENGTH: 506

<212> TYPE: PRT
<213> ORGANISM: Artificial
<220> FEATURE:
<223> OTHER INFORMATION: Mus musculus, Homo sapiens, Synthesized sequence

<400> SEQUENCE: 39

```
Met Glu Leu Gly Leu Cys Trp Val Phe Leu Val Ala Ile Leu Lys Gly
1               5                   10                  15

Val Gln Cys Glu Val Gln Leu Gln Gln Ser Gly Pro Glu Leu Val Lys
            20                  25                  30

Pro Gly Ala Ser Val Lys Met Ser Cys Lys Ala Ser Gly Tyr Ile Phe
        35                  40                  45

Thr Ser Tyr Val Val His Trp Val Lys Gln Lys Pro Gly Gln Gly Leu
    50                  55                  60

Glu Trp Ile Gly Tyr Ile Asn Pro Tyr Asn Asp Gly Thr Lys Tyr Ser
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Asp Asp Ser Ala Val
            100                 105                 110

Tyr Tyr Cys Ala Arg Asp Gly Val Tyr Gly Tyr His Ala Met Asp Cys
        115                 120                 125

Trp Gly Gln Gly Thr Ser Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Gly Gly Ser Gly Gly Gly Ser Gly Gly Gly Gly Ser Gly
                245                 250                 255

Gly Gln Val Gln Leu Gln Gln Ser Gly Ala Glu Leu Ala Arg Pro Gly
            260                 265                 270

Ala Ser Val Lys Met Ser Cys Lys Ala Ser Gly Tyr Thr Phe Thr Arg
        275                 280                 285

Tyr Thr Met His Trp Val Lys Gln Arg Pro Gly Gln Gly Leu Glu Trp
    290                 295                 300

Ile Gly Tyr Ile Asn Pro Ser Arg Gly Tyr Thr Asn Tyr Asn Gln Lys
305                 310                 315                 320

Phe Lys Asp Lys Ala Thr Leu Thr Thr Asp Lys Ser Ser Ser Thr Ala
                325                 330                 335

Tyr Met Gln Leu Ser Ser Leu Thr Ser Glu Asp Ser Ala Val Tyr Tyr
            340                 345                 350

Cys Ala Arg Tyr Tyr Asp Asp His Tyr Cys Leu Asp Tyr Trp Gly Gln
        355                 360                 365

Gly Thr Thr Leu Thr Val Ser Ser Gly Gly Gly Gly Ser Gly
    370                 375                 380
```

Gly Gly Gly Gly Ser Gly Gly Gln Ile Val Leu Thr Gln Ser Pro Ala
385                 390                 395                 400

Ile Met Ser Ala Ser Pro Gly Glu Lys Val Thr Met Thr Cys Ser Ala
            405                 410                 415

Ser Ser Ser Val Ser Tyr Met Asn Trp Tyr Gln Gln Lys Ser Gly Thr
        420                 425                 430

Ser Pro Lys Arg Trp Ile Tyr Asp Thr Ser Lys Leu Ala Ser Gly Val
    435                 440                 445

Pro Ala His Phe Arg Gly Ser Gly Ser Gly Thr Ser Tyr Ser Leu Thr
450                 455                 460

Ile Ser Gly Met Glu Ala Glu Asp Ala Ala Thr Tyr Tyr Cys Gln Gln
465                 470                 475                 480

Trp Ser Ser Asn Pro Phe Thr Phe Gly Ser Gly Thr Lys Leu Glu Ile
            485                 490                 495

Lys Gly Gly Gly His His His His His His
            500                 505

<210> SEQ ID NO 40
<211> LENGTH: 726
<212> TYPE: DNA
<213> ORGANISM: Artificial
<220> FEATURE:
<223> OTHER INFORMATION: Mus musculus (codon-optimized), Homo sapiens,
      Synthesized sequence

<400> SEQUENCE: 40
atggacatga gggtccccgc tcagctcctg gggctccttc tgctttggtt cccaggcgcc       60
agatgtaata ttcagatgac ccagtcaccg agctcactgg cagttagtgc cggcgaaaaa      120
gttaccatga gctgtaaaag cagccatgca gttctgtata gcagcaacca gaaaaactat      180
ctggcatggt accagcagaa gccgggtcag agcccgaaac tgctgattta ttgggccagc      240
acccgcgata gcgtggttcc ggatcgcttt accggtggtg gtagcggcac cgattttacc      300
ctgaccatta ccaatattca gccggaagat ctggcagtgt attattgtca tcagtattta      360
agcagctgga cctttggtgg tggcaccaaa gttgaaatca gcgaactgt ggctgcacca      420 tctgtcttca tcttcccgcc atctgatgag cagttgaaat ctggaactgc tctgttgtg       480 tgcctgctga ataacttcta tcccagagag gccaaagtac agtggaaggt ggataacgcc      540
ctccaatcgg gtaactccca ggagagtgtc acagggcagg acagcaagga cagcacctac      600
agcctcagca gcactctggc gctgagcaaa gcagactacg agaaacacaa agtctacgcc      660
tgcgaagtca cccatcaggg cctgagctcg cccgtcacaa agagcttcaa caggggagag      720
tgttga                                                                 726

<210> SEQ ID NO 41
<211> LENGTH: 241
<212> TYPE: PRT
<213> ORGANISM: Artificial
<220> FEATURE:
<223> OTHER INFORMATION: Mus musculus, Homo sapiens, Synthesized
      sequence

<400> SEQUENCE: 41

Met Asp Met Arg Val Pro Ala Gln Leu Leu Gly Leu Leu Leu Leu Trp
1               5                   10                  15

Phe Pro Gly Ala Arg Cys Asn Ile Gln Met Thr Gln Ser Pro Ser Ser
            20                  25                  30

```
Leu Ala Val Ser Ala Gly Glu Lys Val Thr Met Ser Cys Lys Ser Ser
        35              40              45

His Ala Val Leu Tyr Ser Ser Asn Gln Lys Asn Tyr Leu Ala Trp Tyr
50                  55                  60

Gln Gln Lys Pro Gly Gln Ser Pro Lys Leu Leu Ile Tyr Trp Ala Ser
65              70              75              80

Thr Arg Asp Ser Gly Val Pro Asp Arg Phe Thr Gly Gly Gly Ser Gly
                85              90              95

Thr Asp Phe Thr Leu Thr Ile Thr Asn Ile Gln Pro Glu Asp Leu Ala
            100             105             110

Val Tyr Tyr Cys His Gln Tyr Leu Ser Ser Trp Thr Phe Gly Gly Gly
        115             120             125

Thr Lys Val Glu Ile Lys Arg Thr Val Ala Ala Pro Ser Val Phe Ile
    130             135             140

Phe Pro Pro Ser Asp Glu Gln Leu Lys Ser Gly Thr Ala Ser Val Val
145             150             155             160

Cys Leu Leu Asn Asn Phe Tyr Pro Arg Glu Ala Lys Val Gln Trp Lys
            165             170             175

Val Asp Asn Ala Leu Gln Ser Gly Asn Ser Gln Glu Ser Val Thr Gly
        180             185             190

Gln Asp Ser Lys Asp Ser Thr Tyr Ser Leu Ser Ser Thr Leu Ala Leu
    195             200             205

Ser Lys Ala Asp Tyr Glu Lys His Lys Val Tyr Ala Cys Glu Val Thr
    210             215             220

His Gln Gly Leu Ser Ser Pro Val Thr Lys Ser Phe Asn Arg Gly Glu
225             230             235             240

Cys
```

ANTI-B7-H4 ANTIBODY

CROSS-REFERENCE TO RELATED APPLICATIONS

This application is a national phase application under 35 U.S.C. § 371 of International Application No. PCT/JP2017/026847, filed Jul. 25, 2017, which claims priority to Japanese of Patent Application No. 2016-145902, filed Jul. 26, 2016, each of which is incorporated herein by reference in its entirety.

TECHNICAL FIELD

The present invention relates to an antibody that recognizes an extracellular domain of a human B7-H4 protein, an antibody conjugate-cell complex in which the aforementioned antibody and an effector cell are bound, a bispecific antibody comprising a heavy chain variable region and a light chain variable region of the aforementioned antibody, and the like.

BACKGROUND ART

B7-H4 is a membrane protein belonging to the B7 family and known as an immune checkpoint molecule (Non-patent Document 1). It has been reported that low levels of B7-H4 mRNA expression are observed in various normal tissues such as the lung, the liver, the ovary, and the like, but the expression of B7-H4 protein in these normal tissues has not been confirmed. On the other hand, in various cancer tissues such as ovarian cancer, uterine cancer, endometrium cancer, and the like, high levels of B7-H4 protein expression regardless of the stage have been reported (Non-patent Document 2). Based on these, B7-H4 is considered to be promising as a new molecular marker for cancer and as a target molecule of cancer therapies, but many things on expression and action of B7-H4 have been remained to be elucidated.

Recent progress in antibody engineering have made it possible to produce clinically applicable genetically modified antibodies having low antigenicity to humans like human chimeric antibodies and humanized antibodies and therefore leads to development and approval of antibody medicines one after another mainly in the field of cancer treatment, in particular. Most of the antibodies that have been developed as medical drugs are human IgG with a molecular weight of about 150 kDa and glycoproteins having 2 N-glycoside-linked complex type sugar chains attached to its Fc region. The Fc region is the region to which an Fc receptor or a complement binds and the effector activity such as antibody-dependent cellular cytotoxicity (ADCC) and complement-dependent cytotoxicity (CDC) is considered to be exhibited via this region.

In fact, polymorphism analyses of Fc receptors from cancer patients have revealed that one of the main antitumor mechanisms of the anti-CD20 antibody Rituxan® (rituximab), a therapeutic agent for non-Hodgkin lymphoma, and the anti-Her2 antibody Herceptin® (trastuzumab), a therapeutic agent for breast cancer is the ADCC activity (Non-patent Documents 3 to 7) and the development of techniques for enhancing the ADCC activity that can be applied to the development of medical drugs is drawing attention as a next-generation antibody technique.

Some monoclonal antibodies that specifically recognize B7-H4 have been already disclosed (for example, Patent Documents 1 and 2). In particular, Patent Document 1 discloses an anti-B7-H4 antibody that exhibits ADCC activity against cancer cells expressing B7-H4 in vitro, but does not make it clear if there is a possibility that the antibody exhibits the ADCC activity in vivo. Moreover, Patent Document 1 discloses a bispecific molecule comprising the aforementioned anti-B7-H4 antibody or a fragment thereof and describes as specific examples a bispecific molecule that recognizes B7-H4 and an Fc receptor and the possibility that the bispecific molecule can direct a B7-H4 expressing cell to an effector cell to induce the effector cell activity via the Fc receptor (antibody-dependent cell-mediated cytotoxicity), but such an effect is not actually confirmed.

PRIOR ART DOCUMENTS

Patent Documents

Patent Document 1:
   Japanese unexamined Patent Application Publication (Translation of PCT Application) No. 2011-505372
Patent Document 2:
   Japanese unexamined Patent Application Publication (Translation of PCT Application) No. 2016-509582

Non-patent Documents

Non-patent Document 1:
   Immunity, 18, 849 (2003)
Non-patent Document 2:
   Gynecol Oncol., 134, 181 (2014)
Non-patent Document 3:
   Blood 99, 754 (2002)
Non-patent Document 4:
   Cancer Res., 64, 4664 (2004)
Non-patent Document 5:
   Arthritis Rheum., 48, 455 (2003)
Non-patent Document 6:
   J. Clin. Oncol., 21, 3940 (2003)
Non-patent Document 7:
   Clin. Cancer Res., 10, 5650 (2004)

SUMMARY OF THE INVENTION

Object to be Solved by the Invention

An object of the present invention is to produce a new anti-B7-H4 antibody having high specificity and affinity and to further produce an "antibody conjugate-cell complex" or a "bispecific antibody" in which the ADCC activity of the antibody is increased to provide an effective composition for treating cancer.

Means to Solve the Object

The present inventors have immunized mice with an extracellular domain protein of a human B7-H4 protein as an antigen and produced a plurality of hybridoma lines that produce an antibody having an ability to bind to B7-H4. The present inventors have selected 8 anti-B7-H4 antibodies (H4.018, H4.025, H4.051, H4.079, H4.113, H4.140, H4.160, and H4.209) having high specificity and affinity for a free form of B7-H4 from antibodies derived from the obtained hybridoma lines by ELISA and sandwich ELISA and further revealed by immunostaining experiments using cultured cells made to transiently overexpress the B7-H4 protein that at least H4.018, H4.025, H4.113, H4.121, and H4.209 among the aforementioned anti-B7-H4 antibodies can recognize B7-H4 expressed on the cell surface.

Subsequently, the present inventors immunostained cultured cancer cells expressing a human B7-H4 protein with the aforementioned anti-B7-H4 antibodies (H4.018, H4.025, H4.113, and H4.209). However, the obtained results suggested that none of the anti-B7-H4 antibodies used in the experiment cannot maintain stable binding to cancer cells. Therefore, the present inventors considered that the aforementioned anti-B7-H4 antibody cannot exhibit sufficient ADCC activity when they are used singly for a cancer therapy.

Thus, the present inventors diligently studied a method for enhancing the ADCC activity of the aforementioned anti B7-H4 antibodies, got an original idea that indirect antibody-dependent cellular cytotoxicity (indirect ADCC, iADCC) can be induced by having one of the aforementioned anti-B7-H4 antibodies and an effector cell bound together beforehand and act on a target cell, and produced actually an "anti-B7-H4 antibody-effector cell complex" to confirm its effect. More specifically, the present inventors had an anti-CD3 antibody, a rabbit anti-murine immunoglobulin polyclonal antibody, and an anti-B7-H4 antibody (H4.018, H4.025, H4.113, or H4.209) bound sequentially to an effector cell isolated from human peripheral blood to produce 4 anti-B7-H4 antibody-effector cell complexes (anti-B7-H4 antibody-effector cell complexes: an H4.018-effector cell complex, H4.025-effector cell complex, an H4.113-effector cell complex, and an H4.209-effector cell complex), performed a cytotoxic assay using these anti-B7-H4 antibody-effector cell complexes, and revealed as a result that at least the H4.025-effector cell complex exhibited the cytotoxicity against target cancer cells.

Furthermore, the present inventors analyzed the amino acid and gene sequences of the heavy and light chain variable regions of 7 antibodies (H4.018, H4.025, H4.051, H4.113, H4.121, H4.140, and H4.209) among the aforementioned anti-B7-H4 antibodies, produced 2 bispecific antibodies (scFv-scFv and Fab-scFv) that recognize both B7-H4 and a CD3 antigen ('1' cell antigen) based on the obtained sequence information, and confirmed their effects in vitro and in vivo. As a result, the present inventors have revealed that either of the aforementioned scFv-scFv and Fab-scFv exhibits concentration-dependent cytotoxicity against cancer cells expressing B7-H4 and also that administration of the aforementioned Fab-scFv to tumor-bearing mice result in excellent antitumor effects such as the reduction of tumor size, the accumulation of Fab-scFv and the infiltration of CD8-positive killer T cells in tumor tissue, and the reduction or elimination of B7-H4-positive cancer cells in tumor tissue, thereby completing the present invention.

Accordingly, the present invention relates to: (1) an antibody that recognizes an extracellular domain of a human B7-H4 protein, comprising any one of following regions (a) to (g): (a) a heavy chain variable region comprising the amino acid sequence set forth in SEQ ID NO: 2; (b) a heavy chain variable region comprising the amino acid sequence set forth in SEQ ID NO: 4 or the amino acid sequence set forth in positions 3 to 111 of SEQ ID NO: 4 and a light chain variable region comprising the amino acid sequence set forth in SEQ ID NO: 6 or the amino acid sequence set forth in positions 4 to 104 of SEQ ID NO: 6 or the amino acid sequence set forth in SEQ ID NO: 8; (c) a heavy chain variable region comprising the amino acid sequence set forth in SEQ ID NO: 10 and a light chain variable region comprising the amino acid sequence set forth in SEQ ID NO: 12; (d) a heavy chain variable region comprising the amino acid sequence set forth in SEQ ID NO: 14 and a light chain variable region comprising the amino acid sequence set forth in SEQ ID NO: 16 or 18; (e) a heavy chain variable region comprising the amino acid sequence set forth in SEQ ID NO: 20 and a light chain variable region comprising the amino acid sequence set forth in SEQ ID NO: 22; (t) a heavy chain variable region comprising the amino acid sequence set forth in SEQ ID NO: 24 and a light chain variable region comprising the amino acid sequence set forth in SEQ ID NO: 26; and (g) a heavy chain variable region comprising the amino acid sequence set forth in SEQ ID NO: 28 and a light chain variable region comprising the amino acid sequence set forth in SEQ ID NO: 30; and (2) a nucleic acid encoding an antibody that recognizes an extracellular domain of a human B7-H4 protein, comprising any one of following nucleic acid sequences (A') to (G'): (A') a nucleic acid sequence encoding a heavy chain variable region comprising the amino acid sequence set forth in SEQ ID NO: 2; (B') a nucleic acid sequence encoding a heavy chain variable region comprising the amino acid sequence set forth in SEQ ID NO: 4 or the amino acid sequence set forth in positions 3 to 111 of SEQ ID NO: 4 and a light chain variable region comprising the amino acid sequence set forth in SEQ ID NO: 6 or the amino acid sequence set forth in positions 4 to 104 of SEQ ID NO: 6 or the amino acid sequence set forth in SEQ ID NO: 8; (C) a nucleic acid sequence encoding a heavy chain variable region comprising the amino acid sequence set forth in SEQ ID NO: 10 and a light chain variable region comprising the amino acid sequence set forth in SEQ ID NO: 12; (D') a nucleic acid sequence encoding a heavy chain variable region comprising the amino acid sequence set forth in SEQ ID NO: 14 and a light chain variable region comprising the amino acid sequence set forth in SEQ ID NO: 16 or 18; (E') a nucleic acid sequence encoding a heavy chain variable region comprising the amino acid sequence set forth in SEQ ID NO: 20 and a light chain variable region comprising the amino acid sequence set forth in SEQ ID NO: 22; (F') a nucleic acid sequence encoding a heavy chain variable region comprising the amino acid sequence set forth in SEQ ID NO: 24 and a light chain variable region comprising the amino acid sequence set forth in SEQ ID NO: 26; and (G') a nucleic acid sequence encoding a heavy chain variable region comprising the amino acid sequence set forth in SEQ ID NO: 28 and a light chain variable region comprising the amino acid sequence set forth in SEQ ID NO: 30.

Moreover, the present invention relates to: (3) the nucleic acid according to the aforementioned (2), comprising any one of following nucleic acid sequences (A) to (G): (A) the nucleic acid sequence set forth in SEQ ID NO: 1; (B) the nucleic acid sequence set forth in SEQ ID NO: 3 or the nucleic acid sequence set forth in positions 64 to 390 of SEQ ID NO: 38 and the nucleic acid sequence set forth in SEQ ID NO: 5 or the nucleic acid sequence set forth in positions 76 to 378 of SEQ ID NO: 36 or the nucleic acid sequence set forth in SEQ ID NO: 7; (C) the nucleic acid sequence set forth in SEQ ID NO: 9 and the nucleic acid sequence set forth in SEQ ID NO: 11; (D) the nucleic acid sequence set forth in SEQ ID NO: 13 and the nucleic acid sequence set forth in SEQ ID NO: 15 or 17; (E) the nucleic acid sequence set forth in SEQ ID NO: 19 and the nucleic acid sequence set forth in SEQ ID NO: 21; (F) the nucleic acid sequence set forth in SEQ ID NO: 23 and the nucleic acid sequence set forth in SEQ ID NO: 25; and (G) the nucleic acid sequence set forth in SEQ ID NO: 27 and the nucleic acid sequence set forth in SEQ ID NO: 29; (4) a vector comprising the nucleic acid according to the aforementioned (2) or (3); and (5) a transformant obtained by introducing the vector according to the aforementioned (4) into a host cell.

Furthermore, the present invention relates to: (6) the antibody according to the aforementioned (1), wherein the antibody is a monoclonal antibody; (7) a hybridoma that produces the antibody according to the aforementioned (6); (8) a kit for detecting cancer cells, comprising the antibody according to the aforementioned (1) or (6); (9) an antibody conjugate in which a first antibody consisting of the antibody according to the aforementioned (1) or (6) is bound to a second antibody that recognizes an effector cell antigen; (10) the antibody conjugate according to the aforementioned (9), wherein the second antibody is an antibody that recognizes a CD3 antigen; (11) a composition for treating cancer, comprising the antibody conjugate according to the aforementioned (9) or (10), wherein an effector cell is delivered to a cancer cell by the antibody conjugate; (12) an antibody conjugate-cell complex in which an effector cell is bound to an antibody conjugate in which a first antibody consisting of the antibody according to the aforementioned (1) or (6) is bound to a second antibody that recognizes an effector cell antigen; (13) the antibody conjugate-cell complex according to the aforementioned (12), wherein the first antibody and the second antibody are bound via a third antibody that recognizes both the first antibody and the second antibody, (14) the antibody conjugate-cell complex according to the aforementioned (12) or (13), wherein the first antibody and the second antibody are IgG antibodies derived from the same animal species and the third antibody is an antibody that recognizes IgG antibodies from the animal species; (15) the antibody conjugate-cell complex according to any one of the aforementioned (12) to (14), wherein the first antibody and the second antibody are murine IgG antibodies and the third antibody is an antibody that recognizes murine IgG antibodies; (16) the antibody conjugate-cell complex according to any one of the aforementioned (12) to (15), wherein the effector cell is an effector cell taken from a cancer patient to be treated; and (17) a composition for treating cancer, comprising the antibody conjugate-cell complex according to any one of the aforementioned (12) to (16) as an active ingredient.

Moreover, the present invention relates to: (18) a bispecific antibody comprising any one of following regions (a) to (g) and a region that recognizes an effector cell antigen: (a) a heavy chain variable region comprising the amino acid sequence set forth in SEQ ID NO: 2; (b) a heavy chain variable region comprising the amino acid sequence set forth in SEQ ID NO: 4 or the amino acid sequence set forth in positions 3 to 111 of SEQ ID NO: 4 and a light chain variable region comprising the amino acid sequence set forth in SEQ ID NO: 6 or the amino acid sequence set forth in positions 4 to 104 of SEQ ID NO: 6 or the amino acid sequence set forth in SEQ ID NO: 8; (c) a heavy chain variable region comprising the amino acid sequence set forth in SEQ ID NO: 10 and a light chain variable region comprising the amino acid sequence set forth in SEQ ID NO: 12; (d) a heavy chain variable region comprising the amino acid sequence set forth in SEQ ID NO: 14 and a light chain variable region comprising the amino acid sequence set forth in SEQ ID NO: 16 or 18; (e) a heavy chain variable region comprising the amino acid sequence set forth in SEQ ID NO: 20 and a light chain variable region comprising the amino acid sequence set forth in SEQ ID NO: 22; (f) a heavy chain variable region comprising the amino acid sequence set forth in SEQ ID NO: 24 and a light chain variable region comprising the amino acid sequence set forth in SEQ ID NO: 26; and (g) a heavy chain variable region comprising the amino acid sequence set forth in SEQ ID NO: 28 and a light chain variable region comprising the amino acid sequence set forth in SEQ ID NO: 30; (19) the bispecific antibody according to the aforementioned (18), wherein the region that recognizes an effector cell antigen is a heavy chain variable region and a light chain variable region of an antibody that recognizes a CD3 antigen; (20) the bispecific antibody according to the aforementioned (18) or (19), wherein the bispecific antibody is single chain antibodies; (21) the bispecific antibody according to any one of the aforementioned (18) to (20), comprising the amino acid sequence set forth in SEQ ID NO: 32 or 37; (22) the bispecific antibody according to the aforementioned (18) or (19), wherein the bispecific antibody is an Fab-scFv fusion; (23) the bispecific antibody according to any one of the aforementioned (18), (19), and (22), consisting of a long chain comprising the amino acid sequence set forth in SEQ ID NO: 39 and a short chain comprising the amino acid sequence set forth in SEQ ID NO: 41; and (24) a nucleic acid encoding the bispecific antibody according to any one of the aforementioned (18) to (23).

Furthermore, the present invention relates to: (25) the nucleic acid according to the aforementioned (24), comprising any one of following nucleic acid sequences (A) to (G): (A) the nucleic acid sequence set forth in SEQ ID NO: 1; (B) the nucleic acid sequence set forth in SEQ ID NO: 3 or the nucleic acid sequence set forth in positions 64 to 390 of SEQ ID NO: 38 and the nucleic acid sequence set forth in SEQ ID NO: 5 or the nucleic acid sequence set forth in positions 76 to 378 of SEQ ID NO: 36 or the nucleic acid sequence set forth in SEQ ID NO: 7; (C) the nucleic acid sequence set forth in SEQ ID NO: 9 and the nucleic acid sequence set forth in SEQ ID NO: 11; (D) the nucleic acid sequence set forth in SEQ ID NO: 13 and the nucleic acid sequence set forth in SEQ ID NO: 15 or 17; (E) the nucleic acid sequence set forth in SEQ ID NO: 19 and the nucleic acid sequence set forth in SEQ ID NO: 21; (F) the nucleic acid sequence set forth in SEQ ID NO: 23 and the nucleic acid sequence set forth in SEQ ID NO: 25; and (G) the nucleic acid sequence set forth in SEQ ID NO: 27 and the nucleic acid sequence set forth in SEQ ID NO: 29; (26) the nucleic acid according to the aforementioned (24) or (25), comprising the nucleic acid sequence set forth in SEQ ID NO: 31 or 36; (27) the nucleic acid according to the aforementioned (24) or (25), comprising a nucleic acid comprising the nucleic acid sequence set forth in SEQ ID NO: 38 and a nucleic acid comprising the nucleic acid sequence set forth in SEQ ID NO: 40; (28) a vector comprising the nucleic acid according to any one of the aforementioned (24) to (27); (29) a transformant obtained by introducing the vector according to the aforementioned (28) into a host cell; (30) a composition for treating cancer comprising the bispecific antibody according to any one of the aforementioned (18) to (23), wherein an effector cell is delivered to a cancer cell by the bispecific antibody; (31) a bispecific antibody-cell complex in which the bispecific antibody according to any one of the aforementioned (18) to (23) and an effector cell are bound; (32) the bispecific antibody-cell complex according to the aforementioned (31), wherein the effector cell is an effector cell taken from a cancer patient to be treated; and (33) a composition for treating cancer comprising the bispecific antibody-cell complex according to the aforementioned (31) or (32) as an active ingredient.

Effect of the Invention

According to the present invention, anti-B7-H4 antibodies that make it possible to detect specifically and with high sensitivity a free form of human 97-H4 protein and/or a human B7-H4 protein present on the cell surface can be produced. Moreover, an "antibody conjugate" in which the anti-B7-H4 antibody according to the present invention and an antibody that recognizes effector cells are conjugated and an "antibody conjugate-cell complex" in which an effector cell is further conjugated to the antibody conjugate can enhance the ADCC activity of the anti-B7-H4 antibody according to the present invention and specifically kill cancer cells expressing a human B7-H4 protein. Furthermore, according to the present invention, a bispecific antibody that recognizes both a human B7-H4 protein and an effector cell antigen can be produced based on the sequence information of the heavy and the light chain variable regions of the aforementioned anti-B7-H4 antibody. Such a bispecific antibody can deliver an effector cell specifically to cancer cells and induce effective ADCC, and may be available as a pharmaceutical composition for cancer treatment.

BRIEF DESCRIPTION OF DRAWINGS

FIG. 1 depicts the results of examination of the binding capacity of anti-B7-H4 antibodies according to the present invention (H4.018, H4.025, H4.051, H4.079, H4.113, H4.140, H4.160, and H4.209) to human B7-H4, human B7-H1, and human B7-DC proteins.

FIG. 2 shows the results of examination of the binding capacity of anti-B7-H4 antibodies according to the present invention (H4.018, H4.025, H4.051, H4.113, H4.140, and H4.209) to human B7-H4 at different concentrations.

FIG. 3 shows the results of immunostaining of human B7-H4 expressing 293F cells with anti-B7-H4 antibodies according to the present invention (H4.018, H4.025, H4.051, H4.079, H4.113, H4.121, H4.140, H4.160, and H4.209) and a commercially available antibody (H74 clone).

FIG. 4 shows the results of the confirmation of expression of B7-H4 in a plurality of cancer cell lines using a commercially available anti-B7-H4 antibody (H74 clone).

FIG. 5 shows the results of examination of binding of anti-B7-H4 antibodies according to the present invention (H4.018, H4.025, H4.113, and H4.209) to MDA-MB-468 cells under 4 different conditions.

FIG. 6(a) is a schematic diagram of the antibody conjugate-cell complex according to the present invention. FIG. 6(b) shows the results of examination of indirect antibody-dependent cellular cytotoxicity by the antibody conjugate-cell complex according to the present invention. "H4.018", "H4.025", "H4.113", and "H4.209" in the figure respectively denote "H4.018-effector cell complex", "H4.025-effector cell complex", "H4.113-effector cell complex", and "H4.209-effector cell complex" according to the present invention.

FIG. 7 shows the nucleic acid sequence (SEQ ID NO: 1) and the amino acid sequence (SEQ ID NO: 2) of the heavy chain variable region of H4.018, The shaded part in the figure indicates the CDR3 region.

FIG. 8 shows the nucleic acid sequence (SEQ ID NO: 3) and the amino acid sequence (SEQ ID NO: 4) of the heavy chain variable region of H4.025, The shaded part in the figure indicates the CDR3 region.

FIG. 9 shows the nucleic acid sequence (SEQ ID NO: 5) and the amino acid sequence (SEQ ID NO: 6) of the light chain variable region (κ chain) of H4.025. The shaded part in the figure indicates the CDR3 region.

FIG. 10 shows the nucleic acid sequence (SEQ ID NO: 7) and the amino acid sequence (SEQ ID NO: 8) of the light chain variable region chain) of H4.025. The shaded part in the figure indicates the CDR3 region.

FIG. 11 shows the nucleic acid sequence (SEQ ID NO: 9) and the amino acid sequence (SEQ ID NO: 10) of the heavy chain variable region of H4.051. The shaded part in the figure indicates the CDR3 region.

FIG. 12 shows the nucleic acid sequence (SEQ ID NO: 11) and the amino acid sequence (SEQ ID NO: 12) of the light chain variable region of H4.051. The shaded part in the figure indicates the CDR3 region.

FIG. 13 shows the nucleic acid sequence (SEQ ID NO: 13) and the amino acid sequence (SEQ ID NO: 14) of the heavy chain variable region of H4.113, The shaded part in the figure indicates the CDR3 region.

FIG. 14 shows the nucleic acid sequence (SEQ ID NO: 15) and the amino acid sequence (SEQ ID NO: 16) of the light chain variable region (κ chain) of H4.113, The shaded part in the figure indicates the CDR3 region.

FIG. 15 shows the nucleic acid sequence (SEQ ID NO: 17) and the amino acid sequence (SEQ II) NO: 18) of the light chain variable region (λ chain) of H4.113.

FIG. 16 shows the nucleic acid sequence (SEQ ID NO: 19) and the amino acid sequence (SEQ ID NO: 20) of the heavy chain variable region of H4.121. The shaded part in the figure indicates the CDR3 region.

FIG. 17 shows the nucleic acid sequence (SEQ ID NO: 21) and the amino acid sequence (SEQ ID NO: 22) of the light chain variable region of H4.121, The shaded part in the figure indicates the CDR3 region.

FIG. 18 shows the nucleic acid sequence (SEQ ID NO: 23) and the amino acid sequence (SEQ ID NO: 24) of the heavy chain variable region of H4.140. The shaded part in the figure indicates the CDR3 region.

FIG. 19 shows the nucleic acid sequence (SEQ ID NO: 25) and the amino acid sequence (SEQ ID NO: 26) of the light chain variable region of H4.140. The shaded part in the figure indicates the CDR3 region.

FIG. 20 shows the nucleic acid sequence (SEQ ID NO: 27) and the amino acid sequence (SEQ ID NO: 28) of the heavy chain variable region of H4.209. The shaded part in the figure indicates the CDR3 region.

FIG. 21 shows the nucleic acid sequence (SEQ ID NO: 29) and the amino acid sequence (SEQ ID NO: 30) of the light chain variable region of H4.209. The shaded part in the figure indicates the CDR3 region.

FIG. 22 shows the structure of the bispecific antibody (BsAb) according to the present invention, FIG. 23-1 shows the nucleic acid sequence (the nucleic acid sequence at positions 1 to 495 of SEQ ID NO: 31) and the amino acid sequence (the amino acid sequence at positions 1 to 165 of SEQ ID NO: 32) of BsAb according to the present invention.

FIG. 23-2 shows the nucleic acid sequence (the nucleic acid sequence at positions 496 to 1035 of SEQ ID NO: 31) and the amino acid sequence (the amino acid sequence at positions 166 to 345 of SEQ ID NO: 32) of BsAb according to the present invention.

FIG. 23-3 shows the nucleic acid sequence (the nucleic acid sequence at positions 1036 to 1500 of SEQ ID NO: 31) and the amino acid sequence (the amino acid sequence at positions 346 to 500 of SEQ ID NO: 32) of BsAb according to the present invention.

FIG. 24 shows the structure of scFv-scFv according to the present invention.

FIG. 25-1 shows the nucleic acid sequence (the nucleic acid sequence at positions 1 to 540 of SEQ ID NO: 36) and the amino acid sequence (the amino acid sequence at positions 1 to 180 of SEQ ID NO: 37) of scFv-scFv according to the present invention.

FIG. 25-2 shows the nucleic acid sequence (the nucleic acid sequence at positions 541 to 1080 of SEQ ID NO: 36) and the amino acid sequence (the amino acid sequence at positions 181 to 360 of SEQ ID NO: 37) of scFv-scFv according to the present invention.

FIG. 25-3 shows the nucleic acid sequence (the nucleic acid sequence at positions 1081 to 1602 of SEQ ID NO: 36) and the amino acid sequence (the amino acid sequence at positions 361 to 533 of SEQ ID NO: 37) of scFv-scFv according to the present invention.

FIG. 26 shows the structure of Fab-scFv according to the present invention.

FIG. 27-1 shows the nucleic acid sequence (the nucleic acid sequence at positions 1 to 540 of SEQ ID NO: 38) and the amino acid sequence (the amino acid sequence at positions 1 to 180 of SEQ ID NO: 39) of the long chain of Fab-scFv according to the present invention.

FIG. 27-2 shows the nucleic acid sequence (the nucleic acid sequence at positions 541 to 1080 of SEQ ID NO: 38) and the amino acid sequence (the amino acid sequence at positions 181 to 360 of SEQ ID NO: 39) of the long chain of Fab-scFv according to the present invention.

FIG. 27-3 shows the nucleic acid sequence (the nucleic acid sequence at positions 1081 to 1521 of SEQ ID NO: 38) and the amino acid sequence (the amino acid sequence at positions 361 to 506 of SEQ ID NO: 39) of the long chain of Fab-scFv according to the present invention.

FIG. 28-1 shows the nucleic acid sequence (the nucleic acid sequence at positions 1 to 540 of SEQ ID NO: 40) and the amino acid sequence (the amino acid sequence at positions 1 to 180 of SEQ ID NO: 41) of the short chain of Fab-scFv according to the present invention.

FIG. 28-2 shows the nucleic acid sequence (the nucleic acid sequence at positions 541 to 726 of SEQ ID NO: 40) and the amino acid sequence (the amino acid sequence at positions 181 to 241 of SEQ ID NO: 41) of the short chain of Fab-scFv according to the present invention.

FIG. 29 shows the results of immunostaining of 4 types of breast cancer cells (MDA-MB-468 cells, MDA-MB-231 cells, SKBR3 cells, and ZR75 cells) with anti-B7-H4 antibody (H4.025) and Fab-scFv according to the present invention.

FIG. 30 shows the results of the examination of cytotoxicity of scFv-scFv and Fab-scFv according to the present invention to the breast cancer cells (MDA-MB-468 cells). In the figure, "% Lysis" denotes the ratio of the measured signal to total signal of cells solubilized by a surfactant and "ng/ml" denotes the concentration of Fab-scFv according to the present invention added.

FIG. 31 shows the results of the examination of cytotoxicity of scFv-scFv and Fab-scFv according to the present invention to 4 types of cancer cells. MDA-MB-231 cells, ZR75 cells, and SKBR3 cells are cell lines derived from breast cancer and NCI-H2170 cells are a cell line derived from pulmonary squamous cancer.

FIG. 32 shows the results of the examination of effect of Fab-scFv according to the present invention on the tumor size of tumor-bearing mice. The tumor-bearing mice were produced by transplanting human peripheral blood mononuclear cells and human cancer cells (MDA-MB-468 cells or NCI-H2170 cells) into MHC knockout NOG mice.

FIG. 33 shows the results of the examination of effect of Fab-scFv according to the present invention on tumor tissue of tumor-bearing mice by hematoxylin eosin staining. In the figure, "Control" and "antibody treated" respectively denote tumor tissue derived from untreated tumor-bearing mice and tumor tissue derived from tumor-bearing mice given Fab-scFv according to the present invention.

FIG. 34 shows the results of the examination of effect of Fab-scFv according to the present invention on tumor tissue of tumor-bearing mice by immunostaining with an anti-CD8 antibody and an anti-B7-H4 antibody (H4.025). In the figure, "Control" and "antibody treated" respectively denote tumor tissue derived from untreated tumor-bearing mice and tumor tissue derived from tumor-bearing mice given Fab-scFv according to the present invention.

FIG. 35 shows the results of the examination of localization of Fab-scFv according to the present invention in tumor-bearing mice.

MODE OF CARRYING OUT THE INVENTION

The antibody according to the present invention is not particularly limited, as long as it is an antibody that recognizes an extracellular domain of a human B7-H4 protein, the antibody comprising any one of the following regions (a) to (g): (a) a heavy chain variable region comprising the amino acid sequence set forth in SEQ ID NO: 2; (b) a heavy chain variable region comprising the amino acid sequence set forth in SEQ ID NO: 4 or the amino acid sequence set forth in positions 3 to 111 of SEQ ID NO: 4 and a light chain variable region comprising the amino acid sequence set forth in SEQ ID NO: 6 or the amino acid sequence set forth in positions 4 to 104 of SEQ ID NO: 6 or the amino acid sequence set forth in SEQ ID NO: 8; (c) a heavy chain variable region comprising the amino acid sequence set forth in SEQ ID NO: 10 and a light chain variable region comprising the amino acid sequence set forth in SEQ ID NO: 12; (d) a heavy chain variable region comprising the amino acid sequence set forth in SEQ ID NO: 14 and a light chain variable region comprising the amino acid sequence set forth in SEQ ID NO: 16 or 18; (e) a heavy chain variable region comprising the amino acid sequence set forth in SEQ ID NO: 20 and a light chain variable region comprising the amino acid sequence set forth in SEQ ID NO: 22; (1) a heavy chain variable region comprising the amino acid sequence set forth in SEQ ID NO: 24 and a light chain variable region comprising the amino acid sequence set forth in SEQ ID NO: 26; and (g) a heavy chain variable region comprising the amino acid sequence set forth in SEQ ID NO: 28 and a light chain variable region comprising the amino acid sequence set forth in SEQ ID NO: 30, but preferably, it is an antibody comprising any one of the aforementioned regions (a), (b), (d), (e), and (g), and more preferably it is an antibody comprising the aforementioned region (b). Here, the "antibody" means a full length antibody or a fragment thereof and may be any of a natural antibody from a living organism, a modified antibody, and an antibody produced by gene recombination. Preferable examples of the form of the antibody according to the present invention include a monoclonal antibody, a humanized antibody, a synthetic antibody, a chimeric antibody, a polyclonal antibody, a single chain antibody, an anti-idiotypic (anti-Id) antibody, a Fab fragment, an F(ab')$_2$ fragment, an scFv (single chain antibody), but a monoclonal antibody is particularly preferable.

Among the aforementioned antibodies according to the present invention, the antibody comprising the aforementioned region (b) or (d) may comprise, in either case, one of the 2 types of light chain variable regions (kappa (κ) and lambda (λ)) or both light chain variable regions. More specifically, examples of the antibody comprising the aforementioned region (b) include any of the following antibodies i) to iii): i) an antibody comprising a heavy chain variable region comprising the amino acid sequence set forth in SEQ ID NO: 4 and a light chain variable region comprising the amino acid sequence set forth in SEQ ID NO: 6 (κ chain); ii) an antibody comprising a heavy chain variable region comprising the amino acid sequence set forth in SEQ ID NO: 4 and a light chain variable region comprising the amino acid sequence set forth in SEQ ID NO: 8 (λ chain); iii) an antibody comprising a heavy chain variable region comprising the amino acid sequence set forth in SEQ ID NO: 4 and a light chain variable region comprising the amino acid sequence set forth in SEQ ID NO: 6 (κ chain) and a light chain variable region comprising the amino acid sequence set forth in SEQ ID NO: 8 (λ chain), and examples of the antibody comprising the aforementioned region (d) include any of the following antibodies iv) to vi): iv) an antibody comprising a heavy chain variable region comprising the amino acid sequence set forth in SEQ ID NO: 14 and a light chain variable region comprising the amino acid sequence set forth in SEQ ID NO: 16 (κ chain); v) an antibody comprising a heavy chain variable region comprising the amino acid sequence set forth in SEQ ID NO: 14 and a light chain variable region comprising the amino acid sequence set forth in SEQ ID NO: 18 (λ chain); vi) an antibody comprising a heavy chain variable region comprising the amino acid sequence set forth in SEQ ID NO: 14 and a light chain variable region comprising the amino acid sequence set forth in SEQ ID NO: 16 (κ chain) and a light chain variable region comprising the amino acid sequence set forth in SEQ ID NO: 18 (λ chain)

Moreover, the nucleic acid according to the present invention is not particularly limited, as long as it is a nucleic acid encoding an antibody that recognizes an extracellular domain of a human B7-H4 protein and comprising any one of: (A') a nucleic acid sequence encoding a heavy chain variable region comprising the amino acid sequence set forth in SEQ ID NO: 2; (B') a nucleic acid sequence encoding a heavy chain variable region comprising the amino acid sequence set forth in SEQ ID NO: 4 or the amino acid sequence set forth in positions 3 to 111 of SEQ ID NO: 4 and a light chain variable region comprising the amino acid sequence set forth in SEQ ID NO: 6 or the amino acid sequence set forth in positions 4 to 104 of SEQ ID NO: 6 or the amino acid sequence set forth in SEQ ID NO: 8; (C') a nucleic acid sequence encoding a heavy chain variable region comprising the amino acid sequence set forth in SEQ ID NO: 10 and a light chain variable region comprising the amino acid sequence set forth in SEQ ID NO: 12; (D') a nucleic acid sequence encoding a heavy chain variable region comprising the amino acid sequence set forth in SEQ ID NO: 14 and a light chain variable region comprising the amino acid sequence set forth in SEQ ID NO: 16 or 18; (E') a nucleic acid sequence encoding a heavy chain variable region comprising the amino acid sequence set forth in SEQ ID NO: 20 and a light chain variable region comprising the amino acid sequence set forth in SEQ ID NO: 22; (F') a nucleic acid sequence encoding a heavy chain variable region comprising the amino acid sequence set forth in SEQ ID NO: 24 and a light chain variable region comprising the amino acid sequence set forth in SEQ ID NO: 26; and (G') a nucleic acid sequence encoding a heavy chain variable region comprising the amino acid sequence set forth in SEQ ID NO: 28 and a light chain variable region comprising the amino acid sequence set forth in SEQ ID NO: 30, and the aforementioned nucleic acid sequences may have codon sequences optimized for host cells in which they are expressed. More specifically, preferable examples of the aforementioned nucleic acid sequences include nucleic acids comprises any nucleic acid sequences (A) the nucleic acid sequence set forth in SEQ ID NO: 1; (B) the nucleic acid sequence set forth in SEQ ID NO: 3 or the nucleic acid sequence set forth in positions 64 to 390 of SEQ ID NO: 38 and the nucleic acid sequence set forth in SEQ ID NO: 5 or the nucleic acid sequence set forth in positions 76 to 378 of SEQ ID NO: 36 or the nucleic acid sequence set forth in SEQ ID NO: 7; (C) the nucleic acid sequence set forth in SEQ ID NO: 9 and the nucleic acid sequence set forth in SEQ ID NO: 11; (D) the nucleic acid sequence set forth in SEQ ID NO: 13 and the nucleic acid sequence set forth in SEQ ID NO: 15 or 17; (E) the nucleic acid sequence set forth in SEQ ID NO: 19 and the nucleic acid sequence set forth in SEQ ID NO: 21; (F) the nucleic acid sequence set forth in SEQ ID NO: 23 and the nucleic acid sequence set forth in SEQ ID NO: 25; and (G) the nucleic acid sequence set forth in SEQ ID NO: 27 and the nucleic acid sequence set forth in SEQ ID NO: 29.

The vector according to the present invention is not particularly limited, as long as it comprises the aforementioned nucleic acid according to the present invention and can be constructed by appropriately integrating the nucleic acid according to the present invention in an expression vector. Preferable examples of the aforementioned expression vector are those autonomously replicable in host cells or those that can be integrated into chromosomes of host cells, and those containing a regulatory sequence such as a promoter, an enhancer, a terminator, and the like at a position that allows expression of a polypeptide of a heavy or light chain variable region encoded by the nucleic acid according to the present invention may be preferably used. The expression vector that may be used are an expression vector for animal cells, an expression vector for yeast, an expression vector for bacteria, or the like, but a recombinant vector based on an expression vector for animal cells is preferable.

Examples of the aforementioned expression vector for animal cells include pcDNA3 (manufactured by Stratagene), pCMV-FLAG6a (manufactured by SIGMA Corporation), pEGFP-C3 (manufactured by Clontech Laboratories, Inc.), pcDM8 (commercially available from Funakoshi Co., Ltd.), pAGE107 [Japanese unexamined Patent Application Publication No. 03-22979, Cytotechnology, 3, 133, (1990)], pAS3-3 (Japanese unexamined Patent Application Publication No. 02-227075), pCDM8 [Nature, 329, 840, (1987)], pcDNAI/Amp (manufactured by Invitrogen), pREP4 (manufactured by Invitrogen), pAGE103 [J. Blochem., 101, 1307 (1987)], pAGE210, and the like. Examples of a promoter for animal cells include the promoter of IE (immediate early) genes from cytomegalovirus (human CMV), the early promoter from SV40, a retroviral promoter, the metallothionein promoter, a heat shock promoter, the SR α promoter, and the like. Moreover, examples of the aforementioned expression vector for yeast include YEp13 (ATCC37115), YEp24 (ATCC37051), Ycp5O (ATCC37419), pHS19, pHS15, and the like. Examples of a promoter for yeast include promoters such as the PHO5 promoter, the PGK promoter, the GAP promoter, the ADH promoter, the gal1 promoter, the gal10 promoter, heat shock protein promoters, the MFα1 promoter, the CUP1 promoter, and the like. Furthermore, examples of the aforementioned expression vector for bacteria include pBTrp2, pBTac1, pBTac2 (all commercially available from Boehringer Mannheim), pGEX4T (manufactured by Amersham Biosciences Corp.), pKK233-2 (manufactured by Pharmacia), pSE280 (manufactured by Invitrogen), pGEMEX-1 (manufactured by Promega Corporation), pQE-8 (manufactured by QIA- GEN N.V.), pQE-30 (manufactured by QIAGEN N.V.), pKYP10 (Japanese unexamined Patent Application Publication No. 58-110600), pKYP200 [Agrc. Biol. Chem., 48, 669 (1984)], PLSA1 [Agrc. Blol. Chem., 53, 277 (1989)], pGEL1 [Proc. Natl. Acad. Sci. USA, 82, 4306 (1985)], pBluescript II SK (+), pBluescript II SK (−) (manufactured by Stratagene), pTrS30 (FERMBP-5407), pTrS32 (FERM BP-5408), pGEX (manufactured by Pharmacia), pET-3 (manufactured by Novagen), pTerm2 (U.S. Pat. Nos. 4,686, 191, 4,939,094, 5,160,735), pSupex, pUB110, pTP5, pC194, pUC18 [Gene, 33, 103 (1985)], pUC19 [Gene, 33, 103 (1985)], pSTV28 (manufactured by Takara Shuzo Co., Ltd.), pSTV29 (manufactured by Takara Shuzo Co., Ltd.), pUC118 (manufactured by Takara Shuzo Co., Ltd.), pQE-30 (manufactured by QIAGEN N.V.), and the like. Examples of the promoter for bacteria include promoters derived from *Escherichia coli* or bacteriophages such as the trp promoter (P trp), the lac promoter (P lac), the PL promoter, the PR promoter, and the PSE promoter, the SP01 promoter, the SP02 promoter, the penP promoter, and the like.

The transformant according to the present invention is not particularly limited, as long as it is a transformant obtained by introducing the aforementioned vector according to the present invention into a host cell. Examples of the host cell used here include animal cells such as an L cell, a CHO cell, a COS cell, a HeLa cell, a C127 cell, a BALB/c3T3 cell (including those of mutants defective in dihydrofolate reductase or thymidine kinase), a BHK21 cell, an HEK293 cell, and a Bowes malignant melanoma cell; fungal cells such as yeast and *Aspergillus*; bacterial prokaryotic cells such as *Escherichia coli, Streptomyces, Bacillus subtilis, Streptococcus,* and *Staphylococcus* insect cells such as *Drosophila* S2 and *Spodoptera* Sf9; and plant cells such as *Arabidopsis thaliana*, and the like. Moreover, the method for introducing the recombinant vector according to the present invention into a host cell may be a method appropriate for the host cell. Specific examples of the method for introduction include methods described in many standard laboratory manuals such as Davis et al. (BASIC METHODS IN MOLECULAR BIOLOGY, 1986) and Sambrook et al. (MOLECULAR CLONING: A LABORATORY MANUAL, 2nd Ed., Cold Spring Harbor Laboratory Press, Cold Spring Harbor, N.Y., 1989), for example, calcium phosphate transfection, DEAE-dextran-mediated transfection, transvection, microinjection, cationic lipid-mediated transfection, electroporation, transduction, infection, and the like.

The monoclonal antibody according to the present invention is not particularly limited, but preferable examples thereof include H4.018, H4.025, H4.051, H4.113, H4.121, H4.140, and H4.209 as described in the Examples bellow, and the like. More specifically, preferable examples of the monoclonal antibody comprising the aforementioned region (a) (a heavy chain variable region comprising the amino acid sequence set forth in SEQ ID NO: 2), the monoclonal antibody comprising the aforementioned region (b) (a heavy chain variable region comprising the amino acid sequence set forth in SEQ ID NO: 4 and a light chain variable region comprising the amino acid sequence set forth in SEQ ID NO: 6 or 8), the monoclonal antibody comprising the aforementioned region (c) (a heavy chain variable region comprising the amino acid sequence set forth in SEQ ID NO: 10 and a light chain variable region comprising the amino acid sequence set forth in SEQ ID NO: 12), the monoclonal antibody comprising the aforementioned region (d) (a heavy chain variable region comprising the amino acid sequence set forth in SEQ ID NO: 14 and a light chain variable region comprising the amino acid sequence set forth in SEQ ID NO: 16 or 18), the monoclonal antibody comprising the aforementioned region (e) (a heavy chain variable region comprising the amino acid sequence set forth in SEQ ID NO: 20 and a light chain variable region comprising the amino acid sequence set forth in SEQ ID NO: 22), the monoclonal antibody comprising the aforementioned region (f) (a heavy chain variable region comprising the amino acid sequence set forth in SEQ ID NO: 24 and a light chain variable region comprising the amino acid sequence set forth in SEQ ID NO: 26), and the monoclonal antibody comprising the aforementioned region (g) (a heavy chain variable region comprising the amino acid sequence set forth in SEQ ID NO: 28 and a light chain variable region comprising the amino acid sequence set forth in SEQ ID NO: 30) respectively include H4.018, H4.025, H4.051, H4.113, H4.121, H4.140, and H4.209. Preferable examples of the monoclonal antibody according to the present invention are H4.018, H4.025, H4.113, H4.121, and H4.209 in that they can recognize both a free form of human B7-H4 protein and human B7-H4 protein present on the cell surface and among them H4.025 is particularly preferable.

Among the aforementioned monoclonal antibodies according to the present invention, the monoclonal antibody comprising the aforementioned region (b) or (d) may comprise one of the 2 types of light chain variable regions (kappa (κ) and lambda (λ)) or both light chain variable regions. More specifically, the monoclonal antibody comprising the aforementioned region (b) may be any one of the monoclonal antibodies I) to III): I) a monoclonal antibody comprising a heavy chain variable region comprising the amino acid sequence set forth in SEQ ID NO: 4 and a light chain variable region comprising the amino acid sequence set forth in SEQ ID NO: 6 (κ chain); II) a monoclonal antibody comprising a heavy chain variable region comprising the amino acid sequence set forth in SEQ ID NO: 4 and a light chain variable region comprising the amino acid sequence set forth in SEQ ID NO: 8 (λ chain); III) a monoclonal antibody comprising a heavy chain variable region comprising the amino acid sequence set forth in SEQ ID NO: 4 and a light chain variable region comprising the amino acid sequence set forth in SEQ ID NO: 6 (K chain) and a light chain variable region comprising the amino acid sequence set forth in SEQ ID NO: 8 (λ chain); or an antibody mix of the aforementioned monoclonal antibodies I) and II); and the monoclonal antibody comprising the aforementioned region (d) may be any one of the monoclonal antibodies IV) to VI): IV) a monoclonal antibody comprising a heavy chain variable region comprising the amino acid sequence set forth in SEQ ID NO: 14 and a light chain variable region comprising the amino acid sequence set forth in SEQ ID NO: 16 (K chain); V) a monoclonal antibody comprising a heavy chain variable region comprising the amino acid sequence set forth in SEQ ID NO: 14 and a light chain variable region comprising the amino acid sequence set forth in SEQ ID NO: 18 (λ chain); VI) a monoclonal antibody comprising a heavy chain variable region comprising the amino acid sequence set forth in SEQ ID NO: 14 and a light chain variable region comprising the amino acid sequence set forth in SEQ ID NO: 16 (κ chain) and a light chain variable region comprising the amino acid sequence set forth in SEQ ID NO: 18 chain); or an antibody mix of the aforementioned monoclonal antibodies IV) and V).

The monoclonal antibody according to the present invention can be produced by any method, for example, the hybridoma method (Nature 256, 495-497, 1975), the trioma technique, the human B-cell hybridoma method (Immunology Today 4, 72, 1983) and the EBV-hybridoma method (MONOCLONAL ANTIBODIES AND CANCER THERAPY, pp. 77-96, Alan R. Liss, Inc., 1985), or the like, but it is particular preferred to be produced by the hybridoma method. Moreover, the hybridoma according to the present invention is not particularly limited, as long as it is a hybridoma that produces the aforementioned monoclonal antibody according to the present invention, but, more specifically, preferable examples include the hybridoma clones #18, #25, #51, #113, #121, #140, and #209 (the hybridoma clones that respectively produce the monoclonal antibodies H4.018, H4.025, H4.051, H4.113, H4.121, H4.140, and H4.209 according to the present invention) described in Examples below, and among them preferable examples are the hybridoma clones #18, #25, #113, #121, and #209, and a particularly preferable example is the hybridoma clone #25.

The kit for detecting cancer cells according to the present invention is not particularly limited, as long as it comprises the aforementioned antibody according to the present invention, but, particularly, preferable examples include those comprising the aforementioned monoclonal antibody according to the present invention. The antibody contained in the kit for detecting cancer cells according to the present invention may, depending on the method of detection, be labelled with a fluorescent substance such as fluorescein isocyanate, tetramethylrhodamine isocyanate, or the like; a radioisotope such as $^{125}$I, $^{32}$P, $^{14}$C, $^{35}$S, $^{3}$H, or the like; or an enzyme such as alkaline phosphatase, peroxidase, β-galactosidase, phycoerythrin, or the like or be a fusion protein with a fluorescent proteins such as Green Fluorescent Protein (GFP) or the like. Moreover, the kit for detecting cancer cells according to the present invention may further comprise, in addition to the aforementioned antibody according to the present invention, reagents, solutions, diluents, washing buffer solutions, and standard substances for a known protein detection and/or measurement method for such as ELISA, sandwich ELISA, immunostaining, RIA, or the like, a labelled antibody (secondary antibody) that immunologically react specifically with the aforementioned antibody according to the present invention, a substrate reagent that generates color, photoluminescence, or fluorescence, a protocol describing a procedure and a method for evaluation, and/or the like, and is preferably configured to allow an easy examination. The target of the aforementioned kit for detecting cancer cells according to the present invention may be any type of cancer, as long as it is cancer cells or a cancer tissue expressing human B7-H4 protein, but preferably the kit may be used particularly for detection of ovarian cancer, uterine cancer, endometrial cancer, lung cancer, breast cancer, or the like, known to express B7-H4 protein at a high level.

The present invention also relates to an "antibody conjugate" in which the aforementioned antibody according to the present invention and the antibody that recognizes an effector cell antigen are bound and an "antibody conjugate-cell complex" in which the antibody conjugate and an effector cell are bound. The aforementioned antibody conjugate according to the present invention is not particularly limited, as long as it is an antibody conjugate in which a first antibody consisting of the aforementioned antibody according to the present invention is bound to a second antibody that recognizes an effector cell antigen, but the second antibody is preferably an antibody that recognizes a CD3 antigen. Moreover, the aforementioned antibody conjugate-cell complex according to the present invention is not particularly limited, as long as it is an antibody conjugate-cell complex in which an effector cell is bound to an antibody conjugate in which a first antibody consisting of the aforementioned antibody according to the present invention is bound to a second antibody that recognizes an effector cell antigen, but preferably the first antibody and the second antibody are bound via a third antibody that recognizes both the first antibody and the second antibody, more preferably the first antibody and the second antibody are IgG antibodies derived from the same animal species and the third antibody is an antibody that recognizes IgG antibodies from the aforementioned animal species, and particularly preferably the first antibody and the second antibody are murine IgG antibodies and the third antibody is an antibody that recognizes murine IgG antibodies. Here, the "effector cell" means a cell that is in an immune system expressing an Fc receptor and has activity to bind to the Fc region of the antibody bound on the cell surface of the target cell and kill the target cell. Specifically, preferable examples thereof include a T cell, a monocyte, a macrophage, a neutrophile, a dendritic cell, an acidophile, a mast cell, a platelet, a B cell, a large granular lymphocyte, a Langerhans cell, a natural killer (NK) cell, and the like, but, in particular, it is preferred to be a T cell. Moreover, the aforementioned effector cell may be derived from any animal species. Preferable examples thereof include effector cells derived from a human, a mouse, a rat, a rabbit, a monkey, and the like, but it is preferred to be an effector cell derived from a human and it is particularly preferred to be an effector cell taken from a cancer patient to be treated, The aforementioned "antibody conjugate" and "antibody conjugate-cell complex" according to the present invention increase the ADCC activity while maintaining the binding capacity to human B7-H4 protein (as used herein, ADCC induced by the "antibody conjugate" and the "antibody conjugate-cell complex" may be referred to as "indirect ADCC" (iADCC)). More specifically, even when administration of the antibody according to the present invention alone in the presence of effector cells exhibits insufficient or no ADCC activity on target cells (cancer cells expressing human B7-H4 protein), production of the aforementioned "antibody conjugate" or "antibody conjugate-cell complex" using such antibody according to the present invention makes it possible to deliver the effector cells to the target cells efficiently to cause lysis of the target cells. Therefore, the aforementioned "antibody conjugate" and the "antibody conjugate-cell complex" according to the present invention are available as an ingredient of a composition for treating cancer. The "composition for treating cancer, comprising the antibody conjugate" according to the present invention is not particularly limited, as long as it is a composition comprising the antibody conjugate according to the present invention and the antibody conjugate delivers effector cells to cancer cells. Moreover, the "composition for treating cancer, comprising the antibody conjugate-cell complex" according to the present invention is not particularly limited, as long as it is a composition comprising the antibody conjugate-cell complex according to the present invention as an active ingredient. Here, "cancer" to be treated may be any type of cancer, as long as it is cancer expressing human B7-H4 protein, but particularly preferable examples thereof include ovarian cancer, uterine cancer, endometrial cancer, lung cancer, breast cancer expressing B7-H4 protein at a high level, and the like.

Moreover, the present invention relates to a bispecific antibody that recognizes human B7-H4 protein and an effector cell antigen. The aforementioned bispecific antibody according to the present invention is not particularly limited, as long as it comprises any one of the following regions (a) to (g): (a) a heavy chain variable region comprising the amino acid sequence set forth in SEQ ID NO: 2; (b) a heavy chain variable region comprising the amino acid sequence set forth in SEQ ID NO: 4 or the amino acid sequence set forth in positions 3 to 111 of SEQ ID NO: 4 and a light chain variable region comprising the amino acid sequence set forth in SEQ ID NO: 6 or the amino acid sequence set forth in positions 4 to 104 of SEQ ID NO: 6 or the amino acid sequence set forth in SEQ ID NO: 8; (c) a heavy chain variable region comprising the amino acid sequence set forth in SEQ ID NO: 10 and a light chain variable region comprising the amino acid sequence set forth in SEQ ID NO: 12; (d) a heavy chain variable region comprising the amino acid sequence set forth in SEQ ID NO: 14 and a light chain variable region comprising the amino acid sequence set forth in SEQ ID NO: 16 or 18; (e) a heavy chain variable region comprising the amino acid sequence set forth in SEQ ID NO: 20 and a light chain variable region comprising the amino acid sequence set forth in SEQ ID NO: 22; (f) a heavy chain variable region comprising the amino acid sequence set forth in SEQ ID NO: 24 and a light chain variable region comprising the amino acid sequence set forth in SEQ ID NO: 26; and (g) a heavy chain variable region comprising the amino acid sequence set forth in SEQ ID NO: 28 and a light chain variable region comprising the amino acid sequence set forth in SEQ ID NO: 30, and a region that recognizes an effector cell antigen. The aforementioned "effector cell antigen" may be any antigen, as long as it is an antigen present specifically or at a high level on the cell surface of an effector cell such as a T cell, a monocyte, a macrophage, a neutrophile, a dendritic cell, an acidophile, a mast cell, a platelet, a B cell, a large granular lymphocyte, a Langerhans cell, or a natural killer (NK) cell. Specifically, preferable examples thereof include T cell antigens such as CD3, CD2, CD28, CD44, C69, A13, G1, and the like and natural killer (NK) cell antigens such as 3G8, B73.1, LEUL1, VEP13, and AT10, and the like, but a particularly preferable example thereof is the T cell antigen CD3.

The aforementioned bispecific antibody according to the present invention may be produced by any of various known methods in the art. Specific examples thereof include a method involving fusing an antigen binding region in the aforementioned antibody according to the present invention and a region that recognizes an effector cell antigen by genetic engineering to produce a single chain antibody, a method of production using a hybrid hybridoma, that is, a fusion of 2 different monoclonal antibody-producing cells called quadroma (U.S. Pat. No. 4,474,893), a method of production involving chemically coupling Fab fragments or Fab' fragments of 2 monoclonal antibodies (M. Brennan et al., Science 1985, 9(1708):81-3), and a method of production by covalently binding 2 complete monoclonal antibodies (B. Karpovsky et al., J. Exp. Med. 1984, 160(6): 1686-701), and the like. Among them, the bispecific antibody according to the present invention is preferably a single chain antibody (scFv-scFv) produced by fusing an scFv comprising the antigen binding region in the antibody according to the present invention and scFv comprising a region that recognizes an effector cell antigen by genetic engineering or Fab-scFv in which an Fab comprising the antigen binding region in the antibody according to the present invention and an scFv comprising a region that recognizes an effector cell antigen are fused. The single chain antibody (scFv-scFv) according to the present invention is not particularly limited, as long as it is a bivalent antibody in which heavy and light chain variable regions derived from anti-B7-H4 according to the present invention and heavy and light chain variable regions derived from an antibody that recognizes an effector cell antigen are combined via a synthetic linker that makes it possible to produce the antibody in a single protein chain, but specifically preferable examples include a single chain antibody comprising the amino acid sequence set forth in SEQ ID NO: 32 or 37. Moreover, the Fab-scFv according to the present invention is not particularly limited, as long as it is Fab-scFv in which an Fab comprising heavy and light chain variable regions derived from the anti-B7-H4 according to the present invention and an scFv comprising heavy and light chain variable regions derived from an antibody that recognizes an effector cell antigen are combined or Fab-scFv in which an scFv comprising heavy and light chain variable regions derived from anti-B7-H4 according to the present invention and an Fab comprising heavy and light chain variable regions derived from an antibody that recognizes an effector cell antigen are combined, but specifically preferable examples include Fab-scFv consisting of a long chain comprising the amino acid sequence set forth in SEQ ID NO: 39 and a short chain comprising the amino acid sequence set forth in SEQ ID NO: 11.

Moreover, the present invention relates to a nucleic acid encoding the aforementioned bispecific antibody according to the present invention. The aforementioned "nucleic acid encoding the bispecific antibody according to the present invention" is not particularly limited, as long as it comprises any one of the following sequences (A) to (G): (A) the nucleic acid sequence set forth in SEQ ID NO: 1; (B) the nucleic acid sequence set forth in SEQ ID NO: 3 or the nucleic acid sequence set forth in positions 64 to 390 of SEQ ID NO: 38 and the nucleic acid sequence set forth in SEQ ID NO: 5 or the nucleic acid sequence set forth in positions 76 to 378 of SEQ ID NO: 36 or the nucleic acid sequence set forth in SEQ ID NO: 7; (C) the nucleic acid sequence set forth in SEQ ID NO: 9 and the nucleic acid sequence set forth in SEQ ID NO: 11; (D) the nucleic acid sequence set forth in SEQ ID NO: 13 and the nucleic acid sequence set forth in SEQ ID NO: 15 or 17; (E) the nucleic acid sequence set forth in SEQ ID NO: 19 and the nucleic acid sequence set forth in SEQ ID NO: 21; (F) the nucleic acid sequence set forth in SEQ ID NO: 23 and the nucleic acid sequence set forth in SEQ ID NO: 25; and (G) the nucleic acid sequence set forth in SEQ ID NO: 27 and the nucleic acid sequence set forth in SEQ ID NO: 29, but particularly preferable examples thereof include a nucleic acid comprising the nucleic acid sequence set forth in SEQ ID NO: 31 or 36 or a nucleic acid comprising the nucleic acid sequence set forth in SEQ ID NO: 38 and a nucleic acid comprising the nucleic acid sequence set forth in SEQ ID NO: 40. The vector containing the aforementioned "nucleic acid encoding the bispecific antibody according to the present invention" and a transformant obtained by introducing the vector may be produced appropriately by the method described above.

The aforementioned bispecific antibody according to the present invention and the bispecific antibody-cell complex produced by binding the bispecific antibody and an effector cell is considered to exhibit iADCC activity to cancer cells expressing human B7-H4 protein like the aforementioned "antibody conjugate" and "antibody conjugate-cell complex" according to the present invention and therefore are available as an ingredient of a composition for treating cancer. The composition for treating cancer is not particularly limited, as long as it is a composition for treating cancer comprising the bispecific antibody according to the present invention and an effector cell is delivered to a cancer cell by the bispecific antibody or a composition for treating cancer comprising the bispecific antibody-cell complex according to the present invention. Here, the "cancer" to be treated may be any type of cancer, as long as it is a cancer expressing the B7-H4 protein, but particularly preferable examples thereof include ovarian cancer, uterine cancer, endometrial cancer, lung cancer, breast cancer expressing B7-H4 protein at a high level, and the like.

Herein below, the present invention will be described more specifically by Examples, but the technical scope of the present invention is not limited to these examples.

EXAMPLES

Example 1

[Production of Human B7-H4 Antigen Protein and Expressing Cell Thereof]

To be used in production and evaluation of monoclonal antibodies, (1) a soluble B7-H4 recombinant protein and (2) B7-H4 membrane expressing transfected cells are produced.

(1) Soluble B7-H4 Recombinant Protein (Free Form of Antigen)

The extracellular domain of human B7-H4 isoform 1 protein (NCBI accession number; NP_078902, SEQ ID NO: 33) is composed of a region from leucine at position 25 (Leu25) to serine at position 259 (Ser259). In this study, a nucleic acid fragment with a nucleic acid sequence encoding a signal peptide derived from an immunoglobulin and a nucleic acid sequence encoding a 6 histidine tag and a stop codon added respectively to the side corresponding to the N-terminal and to the side corresponding to the C-terminal of a nucleic acid sequence encoding the amino acid sequence of this extracellular domain (a region from Leu25 to Ser259) was produced and the nucleic acid fragment was incorporated into the pcDNA3.3 expression vector to produce a soluble B7-H4 protein expression vector. 293F cells (Life Technology Inc.) were transfected with the expression vector and cultured, and culture supernatant was collected. Soluble human B7-H4 recombinant protein was purified from the obtained culture supernatant by a general method using a histidine tag affinity column.

To be used as negative control, proteins corresponding to the extracellular domains of human B7-H1 protein (NCBI accession number; AAF25807, SEQ ID NO: 34) and human B7-DC protein (NCBI accession number; NP_079515, SEQ ID NO: 35) were produced and purified by a method similar to that described above (the extracellular domains are the region from phenylalanine at position 19 to arginine at position 238 of human B7-H1 and the region from leucine at position 20 to threonine at position 220 of human B7-DC).

Hereinafter, the recombinant proteins containing the extracellular domain regions of human B7-H4, human B7-H1, and human B7-DC protein produced here may respectively be referred to as "a free form of B7-H4", "a free form of B7-H1", and "a free form of B7-DC".

(2) Membrane B7-H4 Expressing Transfected Cell

A nucleic acid sequence encoding the full length of human B7-H4 isoform 1 protein (Met1 to Lys282; SEQ ID NO: 33) was incorporated in the pcDNA3.3 expression vector to produce full length B7-H4 protein expression vector. 293E cells were transfected with the expression vector and cultured for 48 hours to produce membrane human B7-H4 expressing transfected cells transiently expressing human B7-H4 on the cell membrane (hereinafter, such cells may be referred to as "B7-H4 expressing 293F cells"). Moreover, 293F cells were transfected with the pcDNA3.3 vector with no B7-H4 gene and cultured for 48 hours to produce "control 293F cells" which is not expressing human B7-H4.

Example 2

[Production of Hybridoma]

The free form of B7-H4 produced in Example 1 and the Freund's adjuvant were mixed and the mixture was used to inoculate BALB/cA mice at the back to induce B7-H4 specific antibody-producing cells. Splenocyte taken from the mice after the antigen (B7-H4) sensitization and the myeloma cell line P3X63ag8.653 (obtained from ATCC; American Type Culture Collection) were fused using a conventional method to produce and isolate hybridoma.

Example 3

[Screening for Anti-B7-H4 Antibody-Producing Hybridoma]

A plurality of hybridoma lines obtained in Example 2 were examined for antibody-producing capacity by ELISA.

Specifically, the free form of B7-H4 was added to a 96 well IMMOBILIZER™ Amino Plate (Thermo Fisher Scientific) and incubated at room temperature for 2 hours to immobilize the free form of B7-H4 on the plate surface. Simultaneously, wells with no immobilization of the free form of B7-H4 were prepared as negative control. After incubation, the antigen that was not immobilized was removed and the wells were filled with PBS containing 3% BSA and incubated at 4° C. overnight. In this step, nonspecific binding capacity to the plate surface was blocked to produce a plate for ELISA.

The culture supernatant of each of the plurality of hybridoma lines obtained in Example 2 was 2-times diluted with PBS containing 0.05% TWEEN® 20 to prepare a supernatant sample. The buffer was removed from the wells of the aforementioned plate for ELISA and then the supernatant sample was added and incubated at room temperature for 2 hours. The plate was washed to remove the unbound antibody and then a horseradish peroxidase (HRP) labeled anti-mouse immunoglobulin antibody (GE Healthcare) was added and incubated for 1 hour. The wells were washed, then a peroxidase substrate (BD Biosciences) was added and incubated for 30 minutes, and a sulfuric acid solution at a concentration of 0.1 M or higher was added to stop the color development. Whether an antibody that recognizes B7-H4 in a supernatant sample was contained was examined by measuring the absorption of the solution in each well at a wavelength of 450 nm.

The results of the aforementioned ELISA are shown in Table 1. In this study, a criterion for judging the presence of an anti-B7-H4 antibody in a supernatant sample was whether the absorbance in a B7-H4 immobilized well is 1.0 or more and the absorbance in a negative control well is 0.1 or less. The experimental results are shown in Table 1. Since the supernatant samples derived from the hybridoma clones #18, #21, #25, #51, #77, #79, #113, #121, #140, #160, #167, and #209 meet the above criterion, they were judged to contain an anti-B7-H4 antibody. Thus, the foregoing results have revealed that 12 hybridoma lines having the anti-B7-H4 antibody-producing capacity were obtained (Table 1). These hybridoma clones were subsequently subjected to the secondary isolation to confirm their antibody-producing capacity by a similar method (ELISA) again and then stored under an environment at −150° C.

The present inventors named the anti-B7-H4 monoclonal antibodies produced from the hybridoma clones #18, #21, #25, #51, #77, #79, #113, #121, #140, #160, #167, and #209 respectively H4.018, H4.021, H4.025, H4.051, H4.077, H4.079, H4.113, H4.121, H4.140, H4.160, H4.167, and H4.209. Moreover, hereinafter, these antibodies are referred to as the "anti-B7-H4 antibody according to the present invention".

TABLE 1

| Clone# | Primary screening .1 OD.450 nm | |
|---|---|---|
| (Total 252) | No antigen | B7H4 |
| #18 | 0.003 | 1.963 |
| #21 | 0.001 | 1.963 |
| #25 | 0.008 | 2.004 |
| #51 | 0.007 | 1.963 |
| #77 | 0.002 | 1.974 |
| #79 | 0.003 | 2.003 |
| #113 | 0.005 | 2.013 |
| #121 | 0.002 | 2.024 |
| #140 | 0.004 | 1.062 |
| #160 | 0.004 | 1.938 |
| #167 | 0.006 | 1.775 |
| #209 | 0.008 | 1.926 |
| #251 | N.D. | 1.995 |
| #59 | 0.005 | 0.288 |
| #68 | 0.005 | 0.110 |
| #91 | 0.008 | 0.191 |
| #111 | 0.001 | 0.485 |
| #141 | 0.011 | 0.094 |
| #240 | 0.002 | 0.710 |
| #90 | 0.420 | 0.087 |
| #126 | 1.386 | 0.260 |
| #156 | 1.332 | 0.565 |
| #192 | 0.356 | 0.156 |

Example 4

[Primary: Screening for Binding Capacity of the Antibody]

Specificity and binding capacity were examined by sandwich ELISA for 8 antibodies (H4.018, H4.025, H4.051, H4.079, H4.113, H4.140, H4.160, and H4.209) that were purified at a sufficient amount among the aforementioned anti-B7-H4 antibodies according to the present invention.

Specifically, H4.018, H4.025, H4.051, H4.079, H4.113, H4.140, H4.160, and H4.209 were each diluted with PBS to a concentration of 5 µg/ml, added to wells of a 96 well IMMOBILIZER™ Amino Plate (Thermo Fisher Scientific), and immobilized by incubation at room temperature for 1 hour. Non-immobilized antibodies were removed and then wells were filled with PBS containing 3% BSA to block nonspecific binding capacity of the plate surface by incubation at room temperature for 2 hours to produce a plate for sandwich ELISA.

Next, free forms of antigen proteins (a free form of B7-H4, a free form of B7-H1, or a free form of B7-DC) produced in Example 1 were diluted with PBS containing 0.05% TWEEN® 20 to produce diluted solutions containing each antigen protein at concentrations of 0.01 to 10 µg/ml. After removing the buffer from the plate for sandwich ELISA, the diluted solutions of each antigen protein were added to wells and incubated for 1 hour at room temperature. Unbound antigen was removed and then biotinylated H4.025 (2 µg/ml) was added to all wells and incubated at room temperature for 30 minutes. Unbound biotinylated H4.025 was removed and then diluted streptavidin binding HRP (Thermo Fisher Scientific) was added to wells and allowed to bind to the biotinylated antibody. The wells were washed and then a peroxidase substrate (BD Biosciences) was added to the wells and incubated for 30 minutes. A sulfuric acid solution of 0.1 M or more was added to stop the color development and then the absorption at a wavelength of 450 nm was measured.

The results of the aforementioned sandwich ELISA are shown in FIGS. 1 and 2. The results of examination of the binding capacity of the antibody according to the present invention to B7-H4, B7-H1, and B7-DC revealed that all of the 8 antibodies (H4.018, H4.025, H4.051, H4.079, H4.113, H4.140, H4.160, and H4.209) used in the experiment binds specifically to B7-H4, but not to B7-H1 or B7-DC (FIG. 1). Moreover, the results of examination of the binding capacity of the antibodies according to the present invention to B7-H4 at different concentrations have revealed that all of the 6 antibodies (H4.018, H4.025, H4.051, H4.113, H4.140, and H4.209) used in the experiment increased binding in a B7-H4 concentration-dependent manner (FIG. 2).

Example 5

[Secondary Screening for Binding Capacity of the Antibody]

Example 4 has revealed that the anti-B7-H4 antibodies according to the present invention can specifically recognize the free form of B7-H4. Therefore, the binding capacity of the anti-B7-H4 antibodies according to the present invention to B7-H4 expressed on the cell surface was examined by immunostaining in the next experiment.

Specifically, primary antibody solutions of 9 antibodies (H4.018, H4.025, H4.051, H4.079, H4.113, H4.121, H4.140, H4.160, and H4.209) among the anti-B7-H4 antibodies according to the present invention were produced by preparing at a concentration of 8 µg/ml and mixed with the "B7-H4 expressing 293F cells" or "control 293F cells" produced in Example 1. Moreover, a commercially available anti-B7-H4 antibody (H74 clone, LifeSpan BioSciences, Inc.) was similarly mixed with the "B7-H4 expressing 293F cells" or "control 293F cells" as positive control. After incubation at 4° C. for 30 minutes, an R-phycoerythrin (PE) labelled polyclonal anti-mouse immunoglobulin antibody (4 µg/ml) was added and further incubated at 4° C. for 30 minutes and staining intensity of each cell was measured with the flow cytometer FACS™Canto (BD Biosciences).

As shown in FIG. 3, it was revealed that B7-H4 expressing 293F cells were stained with H4.018, H4.025, H4.113, H4.121, and H4.209. In particular, it was revealed that use of H4.018 and H4.025 gives a strong signal.

Example 6

[Binding Capacity of the Antibody to Cancer Cells]

Next, it was examined whether the anti-B7-H4 antibodies according to the present invention have the binding capacity to cancer cells expressing B7-H4.

Expression of B7-H4 in a plurality of cancer cell lines was confirmed using a commercially available anti-B7-H4 antibody (H74 clone) (all cancer cell lines used in this experiment were purchased from American Type Culture Collection (ATCC) or National Institutes of Biomedical Innovation, Health and Nutrition JCRB cell bank). Specifically, MDA-MB-468 cells (a breast cancer cell line), NCI-H2170 cells (a pulmonary squamous cancer cell line), CAL27 cells (a head and neck cancer cell line), MKN74 cells (a stomach cancer cell line), and COLO201 cells (a colon cancer cell line) were cultured for 36 hours or more using a RPMI1640 culture medium containing 10% FBS and then a commercially available phycoerythrin (PE) labelled anti-B7-H4 antibody (H74 clone, eBioscience Inc.) was added and incubated at 4° C. for 30 minutes. The staining intensity of cells was measured using the flow cytometer FACSCanto™ (BD Biosciences).

As the results shown in FIG. 4, the MDA-MB-468 cells were stained with an anti-B7-H4 antibody (H74 clone), but NCI-H2170 cells, CAL27 cells, MKN74 cells, and COLO201 cells were not stained by the anti-B7-H4 antibody (H74 clone). Based on the foregoing results, it has been revealed that the MDA-MB-468 cells express B7-H4 on the cell surface. Moreover, these results are consistent with the results of quantitative PCR.

Next, binding MDA-MB-468 cells and the anti-B7-H4 antibodies according to the present invention was examined. Specifically, 4 antibodies (H4.018, H4.025, H4.113, and H4.209) among the anti-B7-H4 antibodies according to the present invention were added at a concentration of 10 μg/ml to MDA-MB-468 cells and incubated under the following conditions to iv):

i) conditions in which 0.1% sodium azide was added at 4° C. for 30 minutes;
ii) conditions in which 0.1% sodium azide was added at room temperature for 30 minutes;
iii) conditions in which no sodium azide was added at room temperature for 30 minutes;
iv) culture conditions for 18 hours at 37 degrees and 5% $CO_2$.

After incubation, a PE-labeled polyclonal anti-mouse immunoglobulin antibody at a concentration of 4 μg/ml was added as a secondary antibody and incubated at 4° C. for 30 minutes and the staining intensity of the cells was measured with the flow cytometer FACS™Canto (RD Biosciences).

The results are shown in FIG. 5. When H4.113 and H4.209 were used, no staining signal was obtained under any of the aforementioned incubation conditions i) to iv). On the other hand, when H4.018 and H4.025 were used, staining signals were observed under the aforementioned incubation conditions i) and ii), but staining signals were hardly observed under the aforementioned incubation conditions iii) and iv). Based on the foregoing results, it was suggested that the anti-B7-H4 antibodies according to the present invention (H4.018 and H4.025) bind to B7-H4 expressed on the membrane surface of cancer cells, but the binding is unstable. In particular, in the incubation conditions iv), which are close to conditions in the living body, no binding of either of the antibodies H4.018 and H4.025 was observed.

Based on the foregoing results of Examples 3 to 6, it has been suggested the possibility that H4.025 in particular among the anti-B7-H4 antibodies according to the present invention exhibits excellent binding capacity to a free form of B7-H4, but it is difficult to maintain stable binding to B7-H4 expressed on the membrane surface of cancer cells. From these results, the possibility that the anti-B7-1-14 antibodies according to the present invention do not exhibit sufficient antibody-dependent cellular cytotoxicity (ADCC) alone was considered.

Example 7

[Production of Complex of Anti-B7-H4 Antibody and Effector Cell]

Therefore, the present inventors thought that the antibody-dependent cell cytotoxicity (ADCC) may be induced by binding effector cells and the anti-B7-H4 antibodies according to the present invention beforehand and produced effector cells coated with an anti-B7-H4 antibody (hereinafter, such cells may be referred to as the "anti-B7-H4 antibody-effector cell complex").

Specifically, a mononuclear cell fraction was separated by relative density from human peripheral blood using FICOLL-PAQUE® PLUS (GE Healthcare UK Ltd) by a conventional method. Next, the negative selection was performed using anti-CD14 microbeads and anti-CD19 microbeads (Miltenyi Biotec K.K.) and T cells were concentrated from the aforementioned mononuclear cell fraction to prepare effector cells. The aforementioned negative selection was conducted in accordance with the procedure described in an attached manual to the beads used.

The obtained effector cells were reacted with an anti-CD3 antibody (OKT3 clone, purchased from ATCC) at a high concentration (0.2 mg/ml) in iced water for 10 minutes and the unbound antibody was washed away. 0.5 mg/ml of a rabbit anti-mouse immunoglobulin polyclonal antibody (DakoCytomation) was further added and reacted in iced water for 10 minutes. After the reaction, the unbound antibody was washed away. 0.5 mg/ml of an anti-B7-H4 antibody (H4.018, H4.025, H4.113, or H4.209) was added and reacted in iced water for 10 minutes. Finally, effector cells coated with an anti-B7-H4 antibody were produced by washing the unbound antibody away. More specifically, the "anti-B7-H4 antibody-effector cell complex" produced here is cells with effector cells and an anti-B7-H4 antibody indirectly bound via an anti-CD3 antibody and an anti-mouse IgG antibody, as illustrate in FIG. 6(a).

Hereinafter, the "anti-B7-H4 antibody-effector cell complex" produced using H4.018, H4.025, H4.113, or H4.209 may respectively referred to as the "H4.018-effector cell complex", "H4.025-effector cell complex", "H4.113-effector cell complex", and "H4.209-effector cell complex".

Example 8

[Cytotoxicity Assay]

Indirect antibody-dependent cell cytotoxicity (indirect ADCC: iADCC) of the "anti-B7-H4 antibody-effector cell complex" produced by Example 7 was examined.

Specifically, MDA-MB-468 cells (cancer cells expressing B7-H4) were labelled with a fluorescent chelating agent (TDA) using the DELFIA® EuTDA non-radioactive cytotoxicity detection kit (manufactured by PerkinElmer Inc., the manufacturer's serial number: AD0116) (hereinafter, such cells may be referred to as the "TDA labelled cancer cells"). TDA present within cells of the TDA labelled cancer cells is released into supernatant by cell lysis. Since a stable chelate (EuTDA) that exhibits strong fluorescence is formed when an europium (Eu) solution was reacted with this supernatant, the degree of cytotoxicity can be evaluated by measuring the fluorescence intensity, The TDA labelled cancer cells were seeded to a 96 well U bottom plate (10000 cells/well) wider 4° C. condition and the anti-B7-H4 antibody-effector cell complex produced in Example 7 was further added and mixed. Cells were precipitated by centrifuging the plate at 4° C., and 200 G for 1 minute and then reacted under a 37° C. and 5% $CO_2$ environment for 3 hours. The supernatant after the reaction was collected and the fluorescence intensity was measured using a plate reader (Wallac 1420 ARVOsx multi-label counter, manufactured by PerkinElmer). The measurement was conducted by a usual technique according to an instruction attached to the plate reader. From the obtained signal, the degree of cytotoxicity (the ratio of lysed cells) of the TDA labelled cancer cells was calculated.

The results are shown in FIG. 6(b). It was revealed that the H4.025-effector cell complex among the anti-B7-H4 antibody-effector cell complex used in the assay significantly increases fluorescence from the supernatant depending on the increase in the ratio of the complex to the target cells (TDA labelled cancer cells). On the other hand, no significant increase in fluorescence by the H4.018-effector cell complex, the H4.113-effector cell complex, and the H4.209-effector cell complex was not observed even when the ratio of the complex to the target cells was increased. Based on the following results, it was revealed that at least the H4.025-effector cell complex has cytotoxicity to target cancer cells.

Example 9

[Amino Acid Sequence and Nucleic Acid Sequence of Antibodies]

For 7 antibodies (H4.018, H4.025, H4.051, H4.113, H4.121, H4.140, and H4.209) found to have excellent affinity and specificity from the results of Examples 3 to 5, among the anti-B7-H4 antibodies according to the present invention, the nucleic acid and amino acid sequences of the heavy chain and light chain variable regions were analyzed.

(1) H4.018

The nucleic acid sequence (SEQ ID NO: 1) and the amino acid sequence (SEQ NO: 2) of the heavy chain variable region of H4.018 are shown in FIG. 7. The shaded part in the figure indicates the CDR3 region.

(2) H4.025

The nucleic acid sequence (SEQ ID NO: 3) and the amino acid sequence (SEQ ID NO: 4) of the heavy chain variable region of H4.025 are shown in FIG. 8. Moreover, there were 2 kinds of light chain in H4.025: κ and λ chains. The nucleic acid sequence (SEQ ID NO: 5) and the amino acid sequence (SEQ ID NO: 6) of a light chain variable region (κ chain) of H4.025 are shown in FIG. 9 and the nucleic acid sequence (SEQ ID NO: 7) and the amino acid sequence (SEQ ID NO: 8) of a light chain variable region (λ chain) of H4.025 are shown in FIG. 10. The shaded part in the figure indicates the CDR3 region.

(3) H4.051

The nucleic acid sequence (SEQ ID NO: 9) and the amino acid sequence (SEQ ID NO: 10) of the heavy chain variable region of H4.051 are shown in FIG. 11. The nucleic acid sequence (SEQ ID NO: 11) and the amino acid sequence (SEQ ID NO: 12) of the light chain variable region of H4.051 are shown in FIG. 12. The shaded part in the figure indicates the CDR3 region.

(4) H4.113

The nucleic acid sequence (SEQ ID NO: 13) and the amino acid sequence (SEQ ID NO: 14) of the heavy chain variable region of H4.113 are shown in FIG. 13. Moreover, there were 2 kinds of light chain in H4.113: κ and λ chains. The nucleic acid sequence (SEQ ID NO: 15) and the amino acid sequence (SEQ ID NO: 16) of a light chain variable region (κ chain) of H4.113 are shown in FIG. 14 and the nucleic acid sequence (SEQ ID NO: 17) and the amino acid sequence (SEQ ID NO: 18) of a light chain variable region (λ chain) of H4.113 are shown in FIG. 15. The shaded part in the figure indicates the CDR3 region.

(5) H4.121

The nucleic acid sequence (SEQ ID NO: 19) and the amino acid sequence (SEQ ID NO: 20) of the heavy chain variable region of H4.121 are set forth in FIG. 16. The nucleic acid sequence (SEQ ID NO: 21) and the amino acid sequence (SEQ ID NO: 22) of the light chain variable region of H4.121 are shown in FIG. 17. The shaded part in the figure indicates the CDR3 region.

(6) H4.140

The nucleic acid sequence (SEQ ID NO: 23) and the amino acid sequence (SEQ ID NO: 24) of the heavy chain variable region of H4.140 are shown in FIG. 18. The nucleic acid sequence (SEQ ID NO: 25) and the amino acid sequence (SEQ ID NO: 26) of the light chain variable region of H4.140 are shown in FIG. 19. The shaded part in the figure indicates the CDR3 region.

(7) H4.209

The nucleic acid sequence (SEQ ID NO: 27) and the amino acid sequence (SEQ ID NO: 28) of the heavy chain variable region of H4.209 are shown in FIG. 20. Moreover, the nucleic acid sequence (SEQ ID NO: 29) and the amino acid sequence (SEQ ID NO: 30) of the light chain variable region of H4.209 are shown in FIG. 21. The shaded part in the figure indicates the CDR3 region.

Example 10

[Production of Bispecific Antibody]

Based on the amino acid sequence information of the anti-B7-H4 antibodies according to the present invention, a bispecific antibody (BsAb) that binds to both a B7-H4 antigen and a CD3 antigen of T cells can be produced (hereinafter, such an antibody may be referred to as the "BsAb according to the present invention").

The BsAb according to the present invention may be produced by linking via linkers flanking or directly linking, for example, the amino acid sequence of the light chain variable region of an anti-B7-H4 antibody according to the present invention, the amino acid sequence of the heavy chain variable region of an anti-B7-H4 antibody according to the present invention, the amino acid sequence of the light chain variable region of an anti-CD3 antibody, and the amino acid sequence of the heavy chain variable region of an anti-CD3 antibody. The structure of the BsAb using the light chain κ chain variable region of H4.025 and the heavy chain variable region of H4.025 are shown in FIG. 22. Moreover, the nucleic acid sequence (SEQ ID NO: 31) and the amino acid sequence (SEQ ID NO: 32) of such BsAb are shown in FIG. 23-1 to FIG. 23-3. The 2 BsAbs according to the present invention produced by the present inventors are described in detail in Examples 12 and 13 below.

Example 11

[Cytotoxicity Assay with BsAb-Effector Cell Complex]

The BsAb according to the present invention and an effector cell are bound to produce a BsAb-effector cell complex. Specifically, effector cells were prepared by a method similar to that in Example 7 and the BsAb according to the present invention was bound under a 4° C. or room temperature, or 37° C. environment to form a BsAb-effector cell complex. The induction of ADCC will further be attempted using the BsAb-effector cell complex.

Example 12

[Production of BsAb: scFv-scFv]

The present inventors have produced a BsAb (single chain fragment variable-single chain fragment variable antibody, scFv-scFv) in which a single chain antibody comprising the amino acid sequence of the anti-B7-H4 antibody according to the present invention and a single chain antibody comprising the amino acid sequence of the anti-CD3 antibody are conjugated (hereinafter, such an antibody may be referred to as the "scFv-scFv according to the present invention").

Specifically, the scFv-scFv according to the present invention is produced by linking via linkers flanking the amino acid sequence of the light chain variable region of an anti-B7-H4 antibody according to the present invention, the amino acid sequence of the heavy chain variable region of an anti-B7-H4 antibody according to the present invention, the amino acid sequence of the heavy chain variable region of an anti-CD3 antibody, and the amino acid sequence of the light chain variable region of an anti-CD3 antibody. The structure of scFv-scFv according to the present invention using the light chain variable region of H4.025 and the heavy chain variable region of H4.025 are shown in FIG. 24. Moreover, the nucleic acid sequence (SEQ ID NO: 36) and the amino acid sequence (SEQ ID NO: 37) of such scFv-scFv are shown in FIG. 25. SEQ ID NO: 36 comprises the nucleotide sequence encoding a light chain and a heavy chain variable region of H4.025, but they are different from SEQ ID NOs: 3, 5, and 7 since such a nucleotide sequence is codon-optimized in the assumption of using an *Escherichia coli* expression system. In SEQ ID NOs: 36 and 37, the regions corresponding to the light chain and heavy chain variable regions of H4.025 are as follows (Table 2).

<Light Chain Variable Region>

The region from position 76 (a) to position 378 (t) of SEQ ID NO: 36 corresponds to the region from position 10 (a) to position 312 (t) of SEQ ID NO: 5.

The region from position 26 (Met) to position 126 (Gly) of SEQ ID NO: 37 corresponds to the region from position 4 (Met) to position 104 (Gly) of SEQ ID NO: 6.

<Heavy Chain Variable Region>

The region from position 448 (g) to position 780 (t) of SEQ ID NO: 36 corresponds to the full length of SEQ ID NO: 3.

The region from position 150 (Glu) to position 260 (Gly) of SEQ ID NO: 37 corresponds to the full length of SEQ ID NO: 4.

TABLE 2

|  | Light chain variable region | | Heavy chain variable region | |
| --- | --- | --- | --- | --- |
|  | Nucleotide sequence | Amino acid sequence | Nucleotide sequence | Amino acid sequence |
| H4.025 | Positions 10-312 of SEQ ID No: 5 | Positions 4-104 of SEQ ID No: 6 | Full length of SEQ ID No: 3 | Full length of SEQ ID No: 4 |
| scFv-scFv | Positions 76-378 of SEQ ID No: 36 | Positions 26-126 of SEQ ID No: 37 | Positions 448-780 of SEQ ID No: 36 | Positions 150-260 of SEQ ID No: 37 |

Example 13

[Production of BsAb: Fab-scFv]

Furthermore, the inventors have produced a BsAb (fraction antigen binding-single chain fragment variable, Fab-scFv) in which an Fab antibody comprising the amino acid sequence of an anti-B7-H4 antibody according to the present invention and a single chain antibody comprising the amino acid sequence of an anti-CD3 antibody are combined (hereinafter, such an antibody may be referred to as the "Fab-scFv according to the present invention").

Specifically, the Fab-scFv according to the present invention was produced by binding by a disulfide bond a short chain comprising the amino acid sequence of the light chain variable region of an anti-B7-H4 antibody according to the present invention and the amino acid sequence of a constant region (CL) of the human immunoglobulin and a long chain comprising the amino acid sequence of the heavy chain variable region of an anti-B7-H4 antibody, the amino acid sequence of a constant region (CH1) of the human immunoglobulin, the amino acid sequence of the heavy chain variable region of an anti-CD3 antibody, and the amino acid sequence of the light chain variable region of an anti-CD3 antibody. The structure of Fab-scFv using the light chain variable region of H4.025 and the heavy chain variable region of H4.025 are shown in FIG. 26. Moreover, the nucleic acid sequence and the amino acid sequence (respectively SEQ ID NOs: 38 and 39) of a long chain and the nucleic acid sequence and the amino acid sequence (respectively SEQ ID NOs: 40 and 41) of a short chain of such an Fab-scFv are shown in FIGS. 27 to 28, SEQ ID NOs: 38 and 40 comprise the nucleotide sequences encoding a light chain and a heavy chain variable region of H4.025, but they are different from SEQ ID NOs: 3, 5, and 7 since such a nucleotide sequence is codon-optimized in the assumption of using an *Escherichia coli* expression system. In SEQ ID NOs: 38 to 41, the regions corresponding to the light chain and heavy chain variable region of H4.025 are as follows (Table 3).

<Light Chain Variable Region>

The region from position 76 (a) to position 378 (t) of SEQ ID NO: 40 corresponds to the region from position 10 (a) to position 312 (t) of SEQ ID NO: 5.

The region from position 26 (Met) to position 126 (Gly) of SEQ ID NO: 41 corresponds to the region from position 4 (Met) to position 104 (Gly) of SEQ ID NO: 6.

<Heavy Chain Variable Region>

The region from position 64 (c) to position 390 (t) of SEQ ID NO: 38 corresponds to the region from position 7 (c) to position 333 (t) of SEQ ID NO: 3.

The region from position 22 (Gln) to position 130 (Gly) of SEQ ID NO: 39 corresponds to the region from position 3 (Gln) to position 111 (Gly) of SEQ ID NO: 4.

TABLE 3

|  | Light chain variable region | | Heavy chain variable region | |
| --- | --- | --- | --- | --- |
|  | Nucleotide sequence | Amino acid sequence | Nucleotide sequence | Amino acid sequence |
| H4.025 | Positions 10-312 of SEQ ID No: 5 | Positions 4-104 of SEQ ID No: 6 | Positions 7-333 of SEQ ID No: 3 | Positions 3-111 of SEQ ID No: 4 |
| Fab-scFv | Positions 76-378 of SEQ ID No: 40 | Positions 26-126 of SEQ ID No: 41 | Positions 64-390 of SEQ ID No: 38 | Positions 22-130 of SEQ ID No: 39 |

Example 14

[Binding Capacity of Bispecific Antibody to Cancer Cells]

Next, whether the Fab-scFv according to the present invention has the binding capacity to cancer cells expressing B7-H4 was examined in a method similar to that in Example 6.

Specifically, 4 breast cancer cell lines (MDA-MB-468 cells, MDA-MB-231 cells, SKBR3 cells, and ZR75 cells) were cultured with the RPM11640 culture medium containing 10% FBS for 36 hours or more. Subsequently, the Fab-scFv according to the present invention labelled with the fluorescent dye Cy5.5 or an anti-B7-H4 antibody (H4.025) with no label was added to the aforementioned cultured cells and incubated at 4° C. for 30 minutes. After the incubation, the cells to which the anti-B7-H4 antibody (H4.025) was added were washed and an anti-R-phycoerythrin (PE) labelled polyclonal anti-mouse immunoglobulin antibody (4 µg/ml) was added to the cells and further incubated at 4° C. for 30 minutes. The staining intensity of the cells was measured with the flow cytometer FACSCanto™ (BD Biosciences). As shown in FIG. 29, MDA-MB-468 cells and ZR75 cells were stained with an anti-B7-H4 antibody (H4.025) and the Fab-scFv according to the present invention, but MDA-MB-231 cells and SKBR3 cells were not stained with either antibody. Based on the above results, it was revealed that MDA-MB-468 cells and ZR75 cells express B7-H4, but MDA-MB-231 cells do not express B7-H4.

Example 15

[Cytotoxicity Assay by BsAb According to Present Invention]

The antibody-dependent cell cytotoxicity (ADCC) of the BsAb according to the present invention (scFv-scFv and Fab-scFv according to the present invention) to cancer cell lines was examined.

Specifically, cancer cells (MDA-MB-468 cells) and the BsAb according to the present invention were added to human peripheral blood mononuclear cell fraction prepared by the method described in Example 7 and reacted under an environment at 37° C. and 5% $CO_2$ for 16 hours. The culture supernatant was collected and the number of dead cells was measured using TAKARA LDH Cytotoxicity Detection Kit (Takara Bio Inc.) to calculate cytotoxicity (% Lysis) to cancer cells and 50% maximum effective concentration ($EC_{50}$). As shown in FIG. 30, the 50% maximum effective concentration ($EC_{50}$) for MDA-MB-468 cells was 68 ng/ml for the scFv-scFv according to the present invention and 13 ng/ml for the Fab-scFv according to the present invention. Moreover, as shown in FIG. 31, the BsAb according to the present invention-dependent cell cytotoxicity was found to ZR-75 cells (positive for B7-H4 expression; see FIG. 29), but the BsAb according to the present invention-dependent cytotoxicity was not found to MDA-MB-231 cells (negative for B7-H4 expression; see FIG. 29), to SKBR3 cells (negative for B7-H4 expression; see FIG. 29), and to NCI-H2170 cells (pulmonary squamous cancer cells).

Example 16

[Effect of Fab-scFv According to Present Invention on Tumor-Bearing Mice]

Next, whether the Fab-scFv according to the present invention can exhibit antitumor effect to human tumor transplanted in mouse was reviewed.

Specifically, human peripheral blood mononuclear cells were transplanted into MHC knockout NOG mice (NOD/Shi-scid, IL-2RγKO, IaβKO, β2mKO, Central Institute for Experimental Animals) and a breast cancer cell line MDA-MB-468 cell line) or a lung cancer cell line (NCI-H2170 cell line) were transplanted on the next day. After 2 weeks or more from the transplantation of cancer cell lines, the Fab-scFv according to the present invention was administered in a range of 0.2 µg to 200 µg per mouse. Specifically, the Fab-scFv according to the present invention was administered at 5 µg/20 g body weight per dose to mice (FIG. 32) used in the experiment for confirming tumor size and 0.2 µg, 2 µg, 20 µg, and 200 µg of the Fab-scFv according to the present invention were administered to mice used in the staining experiment (FIGS. 33 and 34) 4 times at 3 to 4 day intervals with gradually increasing doses.

As shown in FIG. 32, it was revealed that the size of tumor formed by the transplantation of MDA-MB-468 cells was decreased by administration of the Fab-scFv according to the present invention. On the other hand, the size of tumor formed by the transplantation of NCI-H2170 cells exhibited no response to the administration of the Fab-scFv according to the present invention. Moreover, as shown in FIG. 33, the results of hematoxylin eosin staining of tumor tissue sections revealed that cancer cells in tumor were eliminated in the tumor-bearing mice administrated the Fab-scFv according to the present invention. Furthermore, as shown in FIG. 34, the results of immunohistological staining of tumor tissue sections confirmed infiltration of CD8-positive killer T cells in tumor as well as the elimination of the B7-H4-positive cancer cells in the tumor-hearing mice administrated the Fab-scFv according to the present invention.

Example 17

[Localization of Fab-scFv According to Present Invention in Tumor-Bearing Mice]

It was confirmed whether the Fab-scFv according to the present invention administered in mice accumulated in the murine heteroplastic transplanted tumor.

Specifically, a cancer cell line (MDA-MB-468) was transplanted into MHC knockout NOG mice (Central institute for Experimental Animals), and after 2 weeks or later the Fab-scFv according to the present invention labelled with the fluorescent dye Cy5.5 was administered in a range of 0.5 micrograms to 200 micrograms per mouse. As shown in FIG. 35, the Fab-scFv according to the present invention was confirmed to accumulate in the transplanted tumor tissue till Day 28 post-administration.

The invention claimed is:

1. An antibody that specifically binds to an extracellular domain of a human B7-H4 protein comprising amino acid residues Leu25 to Ser259 of SEQ ID NO: 33, and comprises the following:
   (a) a heavy chain variable region comprising the amino acid sequence of SEQ ID NO: 4 and a light chain variable region comprising the amino acid sequence of SEQ ID NO: 6.

2. The antibody according to claim 1, wherein the antibody is a monoclonal antibody.

3. A hybridoma that produces the antibody according to claim 2.

4. An antibody conjugate-effector cell complex in which an effector cell is bound to an antibody conjugate, wherein the antibody conjugate comprises a first antibody consisting of the antibody according to claim 1 conjugated to a second antibody that recognizes the effector cell antigen.

5. The antibody conjugate-effector cell complex according to claim 4, wherein the first antibody is conjugated to the second antibody via a third antibody that recognizes both the first antibody and the second antibody.

6. The antibody conjugate-effector cell complex according to claim 4, wherein the effector cell is an effector cell taken from a cancer patient to be treated.

7. A bispecific antibody comprising any one of following regions (a) to (c) that specifically bind to an extracellular domain of a human B7-H4 protein composed of a region from Leu25 to Ser259 of SEQ ID NO: 33, and a heavy chain variable region and a light chain variable region that specifically bind to an effector cell antigen:
   (a) a heavy chain variable region comprising the amino acid sequence of SEQ ID NO: 4 and a light chain variable region comprising the amino acid sequence of SEQ ID NO: 6;
   (b) a heavy chain variable region comprising the amino acid sequence of SEQ ID NO: 4 and a light chain variable region comprising the amino acid sequence of positions 4 to 104 of SEQ ID NO: 6; and
   (c) a heavy chain variable region comprising the amino acid sequence of positions 3 to 111 of SEQ ID NO: 4 and a light chain variable region comprising the amino acid sequence of positions 4 to 104 of SEQ ID NO: 6.

8. The bispecific antibody according to claim 7, wherein the effector cell antigen is a CD3 antigen.

9. The bispecific antibody according to claim 7, wherein the bispecific antibody is a single chain antibody or a Fab-scFv fusion.

10. The bispecific antibody according to claim 7, comprising:
    (a') the amino acid sequence of SEQ ID NO: 32;
    (b') the amino acid sequence of SEQ ID NO: 37; or
    (c') the amino acid sequence of SEQ ID NO: 39 and the amino acid sequence of SEQ ID NO: 41.

11. A nucleic acid comprising a sequence encoding the antibody according to claim 1.

12. The nucleic acid according to claim 11, comprising the following:
    (A) the nucleic acid sequence of SEQ ID NO: 3 and the nucleic acid sequence of SEQ ID NO: 5.

13. A vector comprising the nucleic acid according to claim 11.

14. A transformant obtained by introducing the vector according to claim 13 into a host cell.

15. A bispecific antibody-effector cell complex in which the bispecific antibody according to claim 7 and an effector cell are bound.

16. A nucleic acid comprising a sequence encoding the bispecific antibody according to claim 7.

17. The nucleic acid according to claim 16, comprising any one of following sequences (A) to (C):
  (A) the nucleic acid sequence of SEQ ID NO: 3 and the nucleic acid sequence of SEQ ID NO:5;
  (B) the nucleic acid sequence of positions 448 to 780 of SEQ ID NO: 36 and the nucleic acid sequence of positions 76 to 378 of SEQ ID NO: 36; or
  (C) the nucleic acid sequence of positions 64 to 390 of SEQ ID NO: 38 and the nucleic acid sequence of positions 76 to 378 of SEQ ID NO: 40.

18. The nucleic acid according to claim 16, comprising
  (A') the nucleic acid sequence of SEQ ID NO: 31;
  (B') the nucleic acid sequence of SEQ ID NO: 36; or
  (C') the nucleic acid sequence of SEQ ID NO: 38 and the nucleic acid sequence of SEQ ID NO: 40.

19. A vector comprising the nucleic acid according to claim 16.

20. A transformant obtained by introducing the vector according to claim 19 into a host cell.

\* \* \* \* \*